US011610660B1

(12) United States Patent
Devlin et al.

(10) Patent No.: US 11,610,660 B1
(45) Date of Patent: Mar. 21, 2023

(54) ANTIARRHYTHMIC DRUG DOSING METHODS, MEDICAL DEVICES, AND SYSTEMS

(71) Applicant: AltaThera Pharmaceuticals LLC, Chicago, IL (US)

(72) Inventors: Jodi Devlin, Chicago, IL (US); Brandon Ira Kashfian, Chicago, IL (US)

(73) Assignee: AltaThera Pharmaceuticals LLC, Chicago, IL (US)

(*) Notice: Subject to any disclaimer, the term of this patent is extended or adjusted under 35 U.S.C. 154(b) by 0 days.

(21) Appl. No.: 17/566,840

(22) Filed: Dec. 31, 2021

Related U.S. Application Data

(60) Provisional application No. 63/276,947, filed on Nov. 8, 2021, provisional application No. 63/235,500, filed on Aug. 20, 2021.

(51) Int. Cl.
*G16H 20/17* (2018.01)
*A61M 5/172* (2006.01)
*A61K 31/18* (2006.01)

(52) U.S. Cl.
CPC ............ *G16H 20/17* (2018.01); *A61K 31/18* (2013.01); *A61M 5/172* (2013.01)

(58) Field of Classification Search
CPC ........ G16H 20/17; A61M 5/172; A61K 31/18
See application file for complete search history.

(56) References Cited

U.S. PATENT DOCUMENTS

| 6,043,273 | A | 3/2000 | Duhaylongsod |
| 6,060,454 | A | 5/2000 | Duhaylongsod |
| 6,101,412 | A | 8/2000 | Duhaylongsod |
| 6,124,363 | A | 9/2000 | Appleby et al. |

(Continued)

FOREIGN PATENT DOCUMENTS

| AU | 737668 B2 | 8/2001 |
| AU | 765269 B2 | 9/2003 |

(Continued)

OTHER PUBLICATIONS

Co-Pending U.S. Appl. No. 16/863,567, Response to Jun. 4, 2020 Non-Final Office Action dated Dec. 1, 2020, 10 pages.

(Continued)

*Primary Examiner* — Manuel A Mendez
(74) *Attorney, Agent, or Firm* — New River Valley IP Law, P.C.; Michele L. Mayberry

(57) ABSTRACT

The disclosure relates to a method which includes i) prompting input of: a creatinine clearance (CrCl) of a subject; whether the subject is being initiated or escalated on sotalol hydrochloride; an amount of an oral target dosage of sotalol hydrochloride for the subject; and optionally a projected start time for sotalol hydrochloride infusion; and ii) executing computer executable instructions to derive from a set of rules a sotalol hydrochloride dosing protocol for the subject based on the inputs. The disclosure also relates to systems and medical devices configured to perform one or more steps of the method, as well as a non-transitory computer-readable storage medium comprising computer-executable instructions or software stored thereon capable of performing one or more steps of the method.

20 Claims, 12 Drawing Sheets

(56) References Cited

U.S. PATENT DOCUMENTS

| | | | |
|---|---|---|---|
| 6,136,327 A | 10/2000 | Gupta et al. |
| 6,281,246 B2 | 8/2001 | Sankaranarayanan |
| 6,369,114 B1 | 4/2002 | Weil et al. |
| 6,482,811 B1 | 11/2002 | Bacaner et al. |
| 6,491,039 B1 | 12/2002 | Dobak, III |
| 6,500,459 B1 | 12/2002 | Chhabra et al. |
| 6,544,981 B2 | 4/2003 | Stein et al. |
| 6,627,223 B2 | 9/2003 | Percel et al. |
| 6,632,217 B2 | 10/2003 | Harper et al. |
| 6,645,524 B2 | 11/2003 | Midha et al. |
| 6,720,001 B2 | 4/2004 | Chen et al. |
| 6,800,668 B1 | 10/2004 | Odidi et al. |
| 6,899,700 B2 | 5/2005 | Gehling et al. |
| 6,916,813 B2 | 7/2005 | Atwal et al. |
| 7,004,171 B2 | 2/2006 | Benita et al. |
| 7,005,425 B2 | 2/2006 | Belardinelli et al. |
| 7,005,436 B2 | 2/2006 | Lloyd et al. |
| 7,022,343 B2 | 4/2006 | Philbrook et al. |
| 7,048,945 B2 | 5/2006 | Percel et al. |
| 7,090,830 B2 | 8/2006 | Hale et al. |
| 7,179,597 B2 | 2/2007 | Woosley |
| 7,289,847 B1 | 10/2007 | Gill et al. |
| 7,341,737 B2 | 3/2008 | Gehling et al. |
| 7,371,254 B2 | 5/2008 | Dobak, III |
| 7,396,524 B2 | 7/2008 | Yan |
| 7,417,038 B1 | 8/2008 | Anker et al. |
| 7,526,335 B2 | 4/2009 | Ferek-Petric |
| 7,538,092 B2 | 5/2009 | Orlando et al. |
| 7,572,776 B2 | 8/2009 | Yu et al. |
| 7,674,820 B2 | 3/2010 | Fedida et al. |
| 7,745,665 B2 | 6/2010 | Gant et al. |
| 7,765,110 B1 | 7/2010 | Koneru |
| 7,776,844 B2 | 8/2010 | Yu et al. |
| 7,815,936 B2 | 10/2010 | Hasenzahl et al. |
| 7,829,573 B2 | 11/2010 | Curwen et al. |
| 7,846,968 B2 | 12/2010 | Chien et al. |
| 7,885,824 B1 | 2/2011 | Koneru |
| 7,885,827 B1 | 2/2011 | Koneru |
| 7,951,183 B2 | 5/2011 | Dobak, III |
| 8,106,099 B2 | 1/2012 | Brendel et al. |
| 8,236,782 B2 | 8/2012 | Mosher et al. |
| 8,263,125 B2 | 9/2012 | Vaya et al. |
| 8,268,352 B2 | 9/2012 | Vaya et al. |
| 8,313,757 B2 | 11/2012 | Lengerich |
| 8,377,994 B2 | 2/2013 | Gray et al. |
| 8,399,018 B2 | 3/2013 | Lichter et al. |
| 8,440,168 B2 | 5/2013 | Yang et al. |
| 8,465,769 B2 | 6/2013 | Petereit et al. |
| 8,466,277 B2 | 6/2013 | Orlando et al. |
| 8,575,348 B2 | 11/2013 | Rao et al. |
| 8,696,696 B2 | 4/2014 | Solem |
| 8,709,076 B1 | 4/2014 | Matheny et al. |
| 8,753,674 B2 | 6/2014 | Helson |
| 8,828,432 B2 | 9/2014 | Lengerich |
| 8,865,213 B2 | 10/2014 | Sheth et al. |
| 8,871,452 B2 | 10/2014 | Lee |
| 8,906,847 B2 | 12/2014 | Cleemann et al. |
| 8,962,574 B2 | 2/2015 | Reilly |
| 8,987,262 B2 | 3/2015 | Leaute-Labreze et al. |
| 9,011,526 B2 | 4/2015 | Matheny |
| 9,016,221 B2 | 4/2015 | Brennan et al. |
| 9,044,319 B2 | 6/2015 | Matheny |
| 9,060,969 B2 | 6/2015 | Matheny |
| 9,078,929 B2 | 7/2015 | Kuebelbeck et al. |
| 9,161,952 B2 | 10/2015 | Matheny et al. |
| 9,239,333 B2 | 1/2016 | Snider |
| 9,255,104 B2 | 2/2016 | Rao et al. |
| 9,308,084 B2 | 4/2016 | Matheny |
| 9,399,067 B2 | 7/2016 | Mosher et al. |
| 9,474,719 B2 | 10/2016 | Mullen et al. |
| 9,498,481 B2 | 11/2016 | Rao et al. |
| 9,549,912 B2 | 1/2017 | Milner et al. |
| 9,554,989 B2 | 1/2017 | Kaplan et al. |
| 9,585,851 B2 | 3/2017 | Yun et al. |
| 9,585,884 B2 | 3/2017 | Rao et al. |
| 9,597,302 B1 | 3/2017 | Yan et al. |
| 9,616,026 B2 | 4/2017 | Singh |
| 9,682,041 B2 | 6/2017 | Helson |
| 9,724,297 B2 | 8/2017 | Thomas et al. |
| 9,770,514 B2 | 9/2017 | Ghebre-Sellassie et al. |
| 9,889,148 B2 | 2/2018 | Daemmgen et al. |
| 9,995,756 B2 | 6/2018 | Saffitz et al. |
| 10,117,881 B2 | 11/2018 | Helson |
| 10,238,602 B2 | 3/2019 | Helson et al. |
| 10,258,691 B2 | 4/2019 | Helson et al. |
| 10,349,884 B2 | 7/2019 | Helson et al. |
| 10,357,458 B2 | 7/2019 | Helson |
| 10,449,193 B2 | 10/2019 | Helson et al. |
| 10,450,267 B2 | 10/2019 | Stancl |
| 10,512,620 B1 | 12/2019 | Somberg et al. |
| 10,537,588 B2 | 1/2020 | Daemmgen et al. |
| 10,603,316 B2 | 3/2020 | Xiong et al. |
| 10,617,639 B2 | 4/2020 | Helson |
| 10,793,519 B2 | 10/2020 | Somberg et al. |
| 10,799,138 B2 | 10/2020 | Ivaturi et al. |
| 10,888,524 B2 | 1/2021 | Yenkar et al. |
| 10,888,552 B2 | 1/2021 | Rothman |
| 11,286,235 B2 | 3/2022 | Somberg et al. |
| 11,344,518 B2 | 5/2022 | Somberg |
| 2007/0009564 A1 | 1/2007 | McClain et al. |
| 2012/0003318 A1 | 1/2012 | Schuler et al. |
| 2014/0235631 A1 | 8/2014 | Bunt et al. |
| 2014/0276404 A1 | 9/2014 | Orlowski |
| 2015/0081010 A1 | 3/2015 | Matheny |
| 2015/0210712 A1 | 7/2015 | Blumberg et al. |
| 2016/0082159 A1 | 3/2016 | Orlowski |
| 2016/0128944 A1 | 5/2016 | Chawrai et al. |
| 2016/0228379 A1 | 8/2016 | Kumar et al. |
| 2016/0271070 A1 | 9/2016 | Singh et al. |
| 2016/0271157 A1 | 9/2016 | Ahmed et al. |
| 2016/0303133 A1 | 10/2016 | Dudley et al. |
| 2016/0317388 A1 | 11/2016 | Bhargava et al. |
| 2017/0049705 A1 | 2/2017 | Mateescu et al. |
| 2017/0087105 A1 | 3/2017 | Yan et al. |
| 2017/0100387 A1 | 4/2017 | Arora et al. |
| 2017/0119627 A1 | 5/2017 | Bhargava et al. |
| 2017/0157076 A1 | 6/2017 | Yacoby-Zeevi et al. |
| 2017/0231885 A1 | 8/2017 | Cremers et al. |
| 2017/0258781 A1 | 9/2017 | Noujaim et al. |
| 2017/0296493 A1 | 10/2017 | Thomas et al. |
| 2017/0348303 A1 | 12/2017 | Bosse et al. |
| 2018/0071390 A1 | 3/2018 | Patel et al. |
| 2019/0307343 A1 | 10/2019 | Ivaturi et al. |
| 2019/0352257 A1 | 11/2019 | Somberg et al. |
| 2019/0380605 A1 | 12/2019 | Ivaturi et al. |
| 2019/0388371 A1 | 12/2019 | Somberg |
| 2019/0389888 A1 | 12/2019 | McChesney et al. |
| 2020/0085771 A1 | 3/2020 | Somberg et al. |
| 2020/0093759 A1 | 3/2020 | Somberg et al. |
| 2020/0226481 A1* | 7/2020 | Sim ............... H04L 51/046 |
| 2020/0253903 A1* | 8/2020 | Somberg ............... A61K 9/0019 |
| 2020/0338027 A1 | 10/2020 | Somberg |
| 2020/0383941 A1 | 12/2020 | Brelidze et al. |
| 2021/0076959 A1 | 3/2021 | Ivaturi et al. |
| 2021/0107867 A1 | 4/2021 | Somberg et al. |
| 2021/0283049 A1 | 9/2021 | Somberg |
| 2021/0346325 A1 | 11/2021 | Somberg |
| 2022/0142954 A1 | 5/2022 | Somberg |
| 2022/0241225 A1 | 8/2022 | Somberg |

FOREIGN PATENT DOCUMENTS

| | | |
|---|---|---|
| AU | 2003233653 A1 | 12/2003 |
| AU | 2005299693 A1 | 5/2006 |
| AU | 2010231494 A1 | 11/2011 |
| AU | 2013203252 A1 | 8/2013 |
| AU | 2013381856 A1 | 7/2015 |
| AU | 2011289176 B2 | 9/2015 |
| AU | 2016266020 B2 | 10/2018 |
| AU | 2017357916 A1 | 5/2019 |
| AU | 2016313439 B2 | 10/2019 |
| AU | 2015269699 B2 | 8/2020 |
| EP | 0898964 A1 | 3/1999 |
| EP | 1027329 B1 | 2/2003 |

(56) References Cited

FOREIGN PATENT DOCUMENTS

| | | |
|---|---|---|
| EP | 1467705 A2 | 10/2004 |
| EP | 1474105 A2 | 11/2004 |
| EP | 1605976 A1 | 12/2005 |
| EP | 2429291 A1 | 3/2012 |
| EP | 1501467 B1 | 5/2012 |
| EP | 2238127 B1 | 8/2012 |
| EP | 2238128 B1 | 8/2012 |
| EP | 2228065 B1 | 12/2012 |
| EP | 2797556 A1 | 11/2014 |
| EP | 2861254 A2 | 4/2015 |
| EP | 3100728 A1 | 12/2016 |
| EP | 2999461 A4 | 2/2017 |
| EP | 2714011 B1 | 1/2018 |
| EP | 1951210 B1 | 12/2018 |
| WO | 9921829 A1 | 5/1999 |
| WO | 03020240 A2 | 3/2003 |
| WO | 03059318 A2 | 7/2003 |
| WO | 2004082716 A1 | 9/2004 |
| WO | 2007053393 A2 | 5/2007 |
| WO | 2010132711 A1 | 11/2010 |
| WO | 2012167212 A3 | 2/2013 |
| WO | 2013185764 A2 | 12/2013 |
| WO | 2014133539 A1 | 9/2014 |
| WO | 2014143108 A1 | 9/2014 |
| WO | 2014186843 A1 | 11/2014 |

OTHER PUBLICATIONS

Co-Pending U.S. Appl. No. 16/863,567, Response to Jun. 9, 2021 Non-Final Office Action dated Oct. 12, 2021, 8 pages.

Co-Pending U.S. Appl. No. 16/863,567, Response to May 13, 2020 Restriction Requirement, filed May 26, 2020, 44 pages.

Co-Pending U.S. Appl. No. 16/863,567, Response to Oct. 26, 2021 Final Office Action, dated Dec. 10, 2021, 8 pages.

Co-Pending U.S. Appl. No. 16/863,567, Restriction Requirement dated May 13, 2020, 5 pages.

Co-Pending U.S. Appl. No. 16/946,941, Non-Final Office Action dated Feb. 7, 2022, 15 pages.

Co-Pending U.S. Appl. No. 16/946,941, Preliminary Amendment filed Jan. 20, 2021, 3 pages.

Co-Pending U.S. Appl. No. 16/946,941, Response to Feb. 7, 2022 Non-Final Office Action, dated Mar. 8, 2022, 6 pages.

Co-Pending U.S. Appl. No. 17/585,190, Preliminary Amendment dated Mar. 4, 2022, 4 pages.

Cordarone® (amiodarone HCl) Tablets [package insert], Philadelphia, PA: Wyeth Pharmaceuticals Inc.; 2004, 29 pages.

Dahmane, E., "Clinical Pharmacology-Driven Research to Optimize Bedside Therapeutics of Sotalol Therapy," Clin Transl Sci (2019) 12:648-656.

Dumas, M. et al., "Variations of sotalol kinetics in renal insufficiency", International Journal of Clinical Pharmacology, Therapy, and Toxicology, Oct. 1, 1989, 27(10), Abstract only.

El-Assaad, I, "Lone Pediatric Atrial Fibrillation in the United States: Analysis of Over 1500 Cases," Pediatr. Cardiol. 38:1004-1009, Springer Publishing, United States (2017).

FDA Highlights of Prescribing Information sotalol hydrochloride injection (2009), https://www.accessdata.fda.gov/drugsatfda_docs/label/2009/022306s000lbl.pdf.

FDA Highlights of Prescribing Information Sotylize (sotalol hydrochloride (2014), https://www.accessdata.fda.gov/drugsatfda_docs/label/2014/205108s000lbl.pdf.

Flecainide Acetate Tablets, USP [package insert], Jacksonville, FL: Ranbaxy Pharmaceuticals Inc.; 2003, 17 pages.

Galloway, C.D., "Development and Validation of a Deep-Learning Model to Screen for Hyperkalemia From the Electrocardiogram," JAMA Cardiol.: E1-E9, Amer. Med Assoc., United States (Apr. 3, 2019).

Gomes, J.A., "Oral d,l Sotalol reduces the incidence of postoperative atrial fibrillation in coronary artery bypass surgery patients: a randomized, double-blind, placebo-controlled study," J. Am. Coll. Cardio. 34(2):334-9 (1999).

Hannun, A.Y., "Cardiologist-level arrhythmia detection and classification in ambulatory electrocardiograms using a jeep neural network," Nature Medicine 25:65-69, Nature Publishing (Jan. 2019).

Ho, D.S.W, et al., "Rapid intravenous infusion of d-l sotalol: time to onset of effects on ventricular refractoriness, and safety," European Heart J. 16:81-86, European Soc. of Cardiology, UK (1995).

Hoffman et al. "Renal Insufficiency and Medication in Nursing Homes" Medicine Deutsches Arzteblatt International 2016; 113:92-98.

Ibutilide Fumarate Injection [package insert], Morgantown, WV: Mylan Institutional LLC; 2020, 14 pages.

Kerin, Nicholas A., "Intravenous Sotalol: an under used treatment strategy," Cardiology (2018) 140:143-145.

Laer, S., et al., "Development of a safe and effective pediatric dosing regimen for sotalol based population pharmacokinetics and pharmacodynamics in children with supraventricular tachycardia . . . " Pediatric Cardiology vol. 46(7) (2005) 1322-30.

Li, X, "Efficacy of intravenous sotalol for treatment of incessant tachyarrhythmias in children," Amer. J. of Cardiology (2017) 119:1366-1370.

Li, X., "Pediatric dosing of intravenous sotalol based on body surface area in patients with arrhythmia," Pediatr Cardiol (2017)38:1450-1455.

Lynch, J.J., et al., "Prevention of ventricular fibrillation by dextrorotatory sotalol in conscious canine model of sudden coronary death," Amer. Heart J. vol. 109(5) Part 1, (1985) 949-958.

Marill, K.A., "Meta-analysis of the risk of torsades de pointes in patients treated with intravenous racemic sotalol," Academic Emergency Medicine 8(2):117-124, Wiley, United States (2001).

MULTAQ (dronedarone) tablets, for oral use [package insert], Bridgewater, NJ: Sanofi-Aventis U.S. LLC; 2020, 24 pages.

Neumar, R.W., et al., "Part 8: Adult advanced cardiovascular life support," Circulation (2010) 122, suppl. 3, S729-S767.

Patel, A., "Is Sotalol more effective than standard beta-blockers for prophylaxis of atrial fibrillation during cardiac surgery?" Interactive CardioVascular and Thoracic Surgery 4 (2005) 147-50.

Peters, F.P.J., "Treatment of recent onset atrial fibrillation with intravenous sotalol and/or flecainide," Netherlands J. of Medicine 53:93-96, Elsevier Science B.B., Netherlands (1998).

Peters, N.S., "Post-cardioversion atrial fibrillation: the synthesis of modern concepts?" european Heart J. (2000) 21, 1119-1121.

Procainamide Hydrochloride Injection, USP [package insert], Lake Forest, IL: Hospira, Inc.; 2021, 12 pages.

Radford, D.J., "Atrial Fibrillation in Children," Pediatrics 59(2):250-256, Amer. Acad, of Pediatrics, US (1977).

Rythmol (propafenone hydrochloride tablets), for oral use [package insert], Research Triangle Park, NC: GlaxoSmithKline; 2018, 24 pages.

Sanjuan, R., "Preoperative use of sotalol versus atenolol for atrial fibrillation after cardiac surgery," Ann Thorac Surg (2004) 77:838-43.

Saul, J.P., "Pharmacokinetics and pharmacodynamics of sotalol in a pediatric population with supraventricular and ventricular tachyarrhythmia," Clinical Pharma & Therapeutics 69(3): 145-157 (2001).

Snider, M., et al., "Initial experience with antiarrhythmic medication monitoring by clinical pharmacists in an outpatient setting: a retrospective review," Clinical Therapeutics vol. 31(36) (2009) 1209-1218.

Somberg, J.C., "Gender differences in cardiac repolarization following intravenous sotalol administration," J. Cardiovascular Pharmacology and Therapeutics (2012) 17(1) 86-92.

Somberg, J.C., "QT prolongation and serum sotalol concentration are highly correlated following intravenous and oral sotalol," Cardiology (2010) 116(3):219-25.

Somberg, J.C., et al., "Developing a safe intravenous sotalol dosing regimen," Amer. J. of Therapeutics 17(2010) 365-372.

Somberg, John et al. Model-Informed Development of Sotalol Loading and Dose Escalation Employing an Intravenous Infusion Cardiol Res 2020;11(5):294-304.

Sundquist, H.K. et al., "Serum levels and half-life of sotalol in chronic renal failure", Annals of Clinical Research, Dec. 1, 1975, 7(6), Abstract Only.

(56) References Cited

OTHER PUBLICATIONS

Thomas, S.P., "Rapid loading of sotalol or amiodarone for management of recent onset symptomatic atrial fibrillation: A randomized, digoxin-controlled trial," Am. Heart J., 147(1) (6 pages) (2004).
Tikosyn® (dofetilide) Capsules [package insert], NY, NY: Pfizer Inc.; 2014, 30 pages.
Tse, H.F., "Atrial pacing for suppression of early reinitiation of atrial fibrillation after successful internal cardioversion," european Heart J. (2000) 21, 1167-1176.
U.S. Appl. No. 16/376,706 (U.S. Pat. No. 10,799,138), file history Dec. 2020, 151 pages.
Valdes, S.O., "early experience with intravenous sotalol in children with and without congenital heart disease," Heart Rhythm 15(12): 1862-1869, Elsevier Inc., (Jul. 9, 2018).
Yarlagadda, B, et al., "Safety and efficacy of inpatient initiation of dofetilide versus sotalol for atrial fibrillation," J. Atrial Fibrillation vol. 101(4) (2017) 1-5.
(Ivaturi, Vijay et al.) U.S. Appl. No. 16/376,706, filed Apr. 5, 2019, Specification, Claims, Figures.
(Ivaturi, Vijay et al.) U.S. Appl. No. 16/549,620, filed Aug. 23, 2019, Specification, Claims, Figures and File History as of Dec. 2020, 77 pages (abandoned).
(Ivaturi, Vijay et al.) U.S. Appl. No. 17/003,297, filed Aug. 26, 2020, Specification, Claims, Figures.
(Somberg, John C. et al.) Co-Pending U.S. Appl. No. 16/103,815, filed Aug. 14, 2018, Specification, Claims, Figures.
(Somberg, John C. et al.) Co-Pending U.S. Appl. No. 16/693,310, filed Nov. 24, 2019, Specification, Claims, Figures.
(Somberg, John C. et al.) Co-Pending U.S. Appl. No. 16/693,312, filed Nov. 24, 2019, Specification, Claims, Figures.
(Somberg, John C. et al.) Co-Pending U.S. Appl. No. 16/726,361, filed Dec. 24, 2019, Specification, Claims, Figures.
(Somberg, John) Co-Pending U.S. Appl. No. 16/849,099, filed Apr. 15, 2020, Specification and Claims.
(Somberg, John) Co-Pending U.S. Appl. No. 16/863,567, filed Apr. 30, 2020, Specification and Claims.
(Somberg, John) Co-Pending U.S. Appl. No. 16/946,941, filed Jul. 13, 2020, Specification and Claims.
(Somberg, John) Co-Pending U.S. Appl. No. 17/306,490, filed May 3, 2021, Specification and Claims.
(Somberg, John) Co-Pending U.S. Appl. No. 17/585,190, filed Jan. 26, 2022, Specification and Claims.
Amiodarone HCl injection for intravenous use [package insert], Lake Forest, IL: Hospira, Inc.; Initial U.S. Approval: 1995, 4 pages.
U.S. Appl. No. 17/003,297, Preliminary Amendment filed Dec. 8, 2020, 9 pages.
Barbey, J.T. "Pharmacokinetic, pharmacodynamic, and safety evaluation of an accelerated dose titration regimen of sotalol in healthy middle-aged subjects," Clinical Pharmacology and Therapeutics vol. 66(1) (1999) 91-99.
Bashir, Y. et al., "Electrophysiologic profile and efficacy of intravenous dofetilide (UK-68,798), a new class III antiarrhythmic drug, in patients with sustained monomorphic ventricular tachycardia" The American Journal of Cardiology, vol. 76, Issue 14, Nov. 15, 1995, pp. 1040-1044, abstract.
Batul, S.A., "Intravenous sotalol: Reintroducing a forgotten agent to the electrophysiology therapeutic arsenal," J. Atrial Fibrillation vol. 9(3) (Feb.-Mar. 2017) 1-5.
Blair, Andrew D., et al., Sotalol kinetics in renal insufficiency, Clin. Pharmacol. Ther., 457-463 (Apr. 1981) (7 pages).
Campbell, T.J., "Intravenous sotalol for the treatment of atrial fibrillation and flutter after cardiopulmonary bipass comparison with disopyramide and digoxin in a randomised trial," BR Heart J. (1985) 54:86-90.
Co-Pending U.S. Appl. No. 16/103,815, Final Office Action dated Aug. 13, 2019, 13 pages.
Co-Pending U.S. Appl. No. 16/103,815, Non-Final Office Action dated Feb. 6, 2019, 9 pages.
Co-Pending U.S. Appl. No. 16/103,815, Notice of Allowance dated Oct. 30, 2019, 12 pages.
Co-Pending U.S. Appl. No. 16/103,815, Response to Aug. 13, 2019 Final Office Action, filed Oct. 17, 2019, 10 pages.
Co-Pending U.S. Appl. No. 16/103,815, Response to Dec. 13, 2018 Restriction Requirement, filed Dec. 31, 2018, 3 pages.
Co-Pending U.S. Appl. No. 16/103,815, Response to Feb. 6, 2019 Non-Final Office Action, filed May 6, 2019, 17 pages.
Co-Pending U.S. Appl. No. 16/103,815, Restriction Requirement dated Dec. 13, 2018, 6 pages.
Co-Pending U.S. Appl. No. 16/376,706, Final Office Action dated Mar. 27, 2020, 12 pages.
Co-Pending U.S. Appl. No. 16/376,706, Non-final Office Action dated Nov. 12, 2019, 12 pages.
Co-Pending U.S. Appl. No. 16/376,706, Notice of Allowance and Examiner Initiated Interview Summary dated Jun. 10, 2020, 8 pages.
Co-Pending U.S. Appl. No. 16/376,706, Response to Mar. 27, 2020 Final Office Action dated May 27, 2020, 11 pages.
Co-Pending U.S. Appl. No. 16/376,706, Response to Nov. 12, 2019 Non-Final Office Action filed Feb. 12, 2020, 10 pages.
Co-Pending U.S. Appl. No. 16/693,310, Final Office Action dated Sep. 3, 2021, 20 pages.
Co-Pending U.S. Appl. No. 16/693,310, Non-Final Office Action dated Feb. 7, 2020, 12 pages.
Co-Pending U.S. Appl. No. 16/693,310, Petition Decision dated Mar. 29, 2021, 2 pages.
Co-Pending U.S. Appl. No. 16/693,310, Response to Feb. 7, 2020 Non-Final Office Action, filed May 5, 2020, 20 pages.
Co-Pending U.S. Appl. No. 16/693,310, Response to Sep. 3, 2021 Final Office Action, dated Feb. 3, 2022, 7 pages.
Co-Pending U.S. Appl. No. 16/693,312, Final Office Action dated Mar. 29, 2021, 14 pages.
Co-Pending U.S. Appl. No. 16/693,312, Non-Final Office Action dated Jan. 7, 2022, 15 pages.
Co-Pending U.S. Appl. No. 16/693,312, Non-Final Office Action dated Oct. 20, 2020, 17 pages.
Co-Pending U.S. Appl. No. 16/693,312, Response to Mar. 29, 2021 Final Office Action, filed Sep. 29, 2021, 13 pages.
Co-Pending U.S. Appl. No. 16/693,312, Response to Oct. 20, 2020 Non-Final Office Action, filed Feb. 22, 2021, 11 pages.
Co-Pending U.S. Appl. No. 16/849,099, Final Office Action dated Feb. 3, 2021, 24 pages.
Co-Pending U.S. Appl. No. 16/849,099, Non-Final Office Action dated Jul. 9, 2020, 19 pages.
Co-Pending U.S. Appl. No. 16/849,099, Notice of Abandonment, Aug. 20, 2021, 2 pages.
Co-Pending U.S. Appl. No. 16/849,099, Response to Jul. 9, 2020 Non-Final Office Action, dated Dec. 9, 2020, 10 pages.
Co-Pending U.S. Appl. No. 16/863,567, Advisory Action dated Dec. 30, 2021, 11 pages.
Co-Pending U.S. Appl. No. 16/863,567, Final Office Action dated Dec. 28, 2020, 17 pages.
Co-Pending U.S. Appl. No. 16/863,567, Final Office Action dated Oct. 26, 2021, 11 pages.
Co-Pending U.S. Appl. No. 16/863,567, Non-Final Office Action and Examiner Initiated Interview Summary dated Jun. 9, 2021, 14 pages.
Co-Pending U.S. Appl. No. 16/863,567, Non-Final Office Action dated Jun. 4, 2020, 18 pages.
(Somberg, John) Co-Pending U.S. Appl. No. 17/725,189, filed Apr. 20, 2022, Specification and Claims.
U.S. Appl. No. 17/003,297, Non-Final Office Action dated Mar. 14, 2022, 14 pages.
U.S. Appl. No. 17/003,297, Response to Mar. 14, 2022 Non-Final Office Action, dated Jun. 15, 2022, 12 pages.
Batra, Anjan S., et al., "Junctional ectopic tachycardia: Current strategies for diagnosis and management," Progress in Pediatric Cardiology, 35 (2013) 49-54.
Borquez, Alejandro A., et al., "Intravenous Sotalol in the Young, Safe and Effective Treatment With Standardized Protocols," JACC: Clinical Elecrophysiology, vol. 6, No. 4, Apr. 2020:425-32 (2020).

(56) References Cited

OTHER PUBLICATIONS

CHOC Children's, "Junctional Ectopic Tachycardia (JET) Care Guideline for Cardiovascular Intensive Care Unit (CVICU)," Sep. 18, 2019.
Cilliers, Antionette M., et al., "Junctional ectopic tachycardia in six paediatric patients," Heart; 78:413-415 (1997).
Co-Pending U.S. Appl. No. 16/693,312, Response to Jan. 7, 2022 Non-Final Office Action, dated Jul. 6, 2022, 8 pages.
Co-Pending U.S. Appl. No. 16/946,941, Notice of Allowance dated Apr. 4, 2022, 9 pages.
Learn the Heart, "Antiarrhythmic Drug Review," https://www.healio.com/cardiology/learn-the-heart/cardiology-review/topic-reviews/antiarrhythmic-drugs (Year: 2022).
Maragnes, P., et al., "Usefulness of oral sotalol for the treatment of junctional ectopic tachycardia," Int'l J. of Cardiology, 35 (1995) 165-167.
(Kashfian, Brandon Ira et al.) Co-Pending U.S. Appl. No. 17/892,301, filed Aug. 22, 2022, Specification and Claims.
(Somberg, John C. et al.) Co-Pending U.S. Appl. No. 17/861,226, filed Jul. 10, 2022, Specification, Claims, Figures.
U.S. Appl. No. 17/003,297, Final Office Action dated Jul. 27, 2022, 16 pages.
U.S. Appl. No. 17/003,297, Notice of Allowance dated Oct. 18, 2022, 7 pages.
U.S. Appl. No. 17/003,297, Response to Final Office Action dated Sep. 27, 2022, 12 pages.
Cantillon, D. J. and Amuthan, R. "Atrial Fibrillation", Cleveland Clinic: Center for Continuing Education, Disease Management: https://www.clevelandclinicmeded.com/medicalpubs/diseasemanagement/cardiology/atrial-fibrillation/, Aug. 2018, 18 pages.
Co-Pending U.S. Appl. No. 16/693,310, Non-Final Office Action dated Jul. 21, 2022, 16 pages.
Co-Pending U.S. Appl. No. 16/693,312, Final Office Action dated Oct. 14, 2022, 16 pages.
Co-Pending U.S. Appl. No. 17/861,226, Preliminary Amendment dated Jul. 10, 2022, 4 pages.
Le Coz, F. et al. Pharmacokinetic and pharmacodynamic modeling of the effects of oral and intravenous administrations of dofetilide on ventricular repolarization. Clin Pharmacol Ther 1995; 57:533.
Rasmussen, H.S. et al., Dofetilide, A Novel Class III Antiarrhythmic Agent, J Cardiovasc Pharmacol. 1992;20 Suppl 2:S96-105.
Rosseau, M. F., Cardiac and Hemodynamic Effects of Intravenous Dofetilide in Patients With Heart Failure, Am J Cardiol 2001;87:1250-1254.
Sedgwick, M. et al., Pharmacokinetic and pharmacodynamic effects of UK-68,798, a new potential class III antiarrhythmic drug, Br. J. Clin. Pharmac. (1991), 31, 515-519.
Somberg, et al., "Sotalol versus Amiodarone in Treatment of Atrial Fibrillation," J. Atrial Fibrillation, Feb.-Mar. 2016, vol., Issue 5.

\* cited by examiner

ANTIARRHYTHMIC DRUG DOSING METHODS, MEDICAL DEVICES, AND SYSTEMS

CROSS-REFERENCE TO RELATED APPLICATIONS

The present application relies on the disclosure of and claims priority to and the benefit of the filing date of U.S. Provisional Application No. 63/235,500, filed Aug. 20, 2021, and U.S. Provisional Application No. 63/276,947, filed Nov. 8, 2021, the disclosures of which are hereby incorporated by reference herein in their entireties.

FIELD OF THE INVENTION

The present disclosure is directed to the field of cardiovascular pharmaceutics, and more particularly to computer-implemented methods of determining antiarrhythmic drug dosing and administering antiarrhythmic drugs for the treatment of cardiovascular conditions such as arrhythmias, and medical devices and systems capable of performing the methods.

BACKGROUND

Determining the appropriate dosing of antiarrhythmic drugs can be complex, difficult to understand or apply, and/or time consuming. In situations where a patient is having a cardiovascular crisis, practitioners need to act quickly and, thus, make decisions quickly. Dosing an antiarrhythmic drug, however, often involves simultaneous and careful consideration of a plethora of parameters. Typical dosing parameters can include whether to administer the drug to a patient based on the patient's QT interval or QTc and/or the patient's capability of clearing the drug from their body (such as renal clearance as measured by creatinine clearance rate), how much drug to administer intravenously (loading dose) and for what amount of time, whether to administer multiple IV doses or a single IV dose, when to start oral and/or IV maintenance dosing of the drug relative to the start or completion of the IV loading dose, the amount of the target oral or IV maintenance dose for the patient, whether the patient is being initiated on the drug or whether the patient's current oral or IV maintenance drug therapy is being escalated to a higher oral or IV maintenance drug therapy, and the timing interval between subsequent doses (IV or oral maintenance doses). In some cases, one or more or all of these factors are considered in determining the dosing protocol for a patient that will be used for administering the antiarrhythmic drug to the patient. Software, such as a mobile application or app, appropriately programmed, can be used to determine and/or confirm a practitioner's determination of the dosing protocol appropriate for a particular patient based on one or more or all of the above parameters, or other relevant parameters. The systematic application of known dosing criteria by a software app, when applied to the circumstances of a particular patient, can increase the safety of dosing/administering antiarrhythmic drugs, such as sotalol, dofetilide, amiodarone, ibutilide, dronedarone, procainamide, flecainide, or propafenone.

Sotalol is an antiarrhythmic drug with Class II (beta-adrenoreceptor blocking) and Class III (cardiac action potential duration prolongation) properties. Sotalol is indicated for the maintenance of normal sinus rhythm (delay in time to recurrence of atrial fibrillation/atrial flutter (AFIB/AFL)) in patients with symptomatic AFIB/AFL who are currently in sinus rhythm, and indicated for the treatment of life-threatening ventricular tachycardia.

Typical adult dosages for oral sotalol are 80 mg, 120 mg, and 160 mg, while intravenous doses of sotalol range from 60-112.5 mg.

Sotalol hydrochloride is a white, crystalline solid with a molecular weight of 308.8. It is hydrophilic, soluble in water, propylene glycol and ethanol, but is only slightly soluble in chloroform. Chemically, sotalol hydrochloride is d,l-N-[4-[1-hydroxy-2-[(1-methylethyl) amino]ethyl]phenyl]methane-sulfonamide monohydrochloride. The molecular formula is $C_{12}H_{20}N_2O_3S \cdot HCl$. Sotalol is represented by the following structural formula:

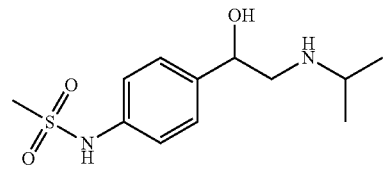 [SMILES: CC(C)NCC(O)c1ccc(NS(C)(=O)=O)cc1]

Sotalol can cause serious ventricular arrhythmias, primarily Torsade de Pointes (TdP) type ventricular tachycardia, a polymorphic ventricular tachycardia associated with QTc prolongation. QTc prolongation is directly related to the concentration of sotalol in the patient. As a result, the US FDA has mandated in-hospital QTc monitoring for at least three days upon initial sotalol hydrochloride loading and for dose escalation. Sotalol is currently approved in the US for oral administration (for example, under the brand name BETAPACE AF®, Bayer HealthCare Pharmaceuticals Inc.) and is approved for IV administration (AltaThera Pharmaceuticals LLC).

Ibutilide as an antiarrhythmic drug is characterized by predominantly Class III properties and is represented by the following structural formula:

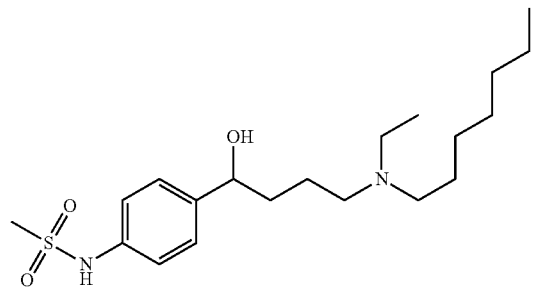 [SMILES: CCCCCCCN(CC)CCCC(O)c1ccc(NS(C)(=O)=O)cc1]

Ibutilide (a methanesulfonanilide derivative) is currently approved in the United States for intravenous administration (under the brand name CORVERT®, Pfizer Inc.) for the treatment of atrial fibrillation or atrial flutter. Patients with atrial arrhythmias of recent onset are more likely to respond to ibutilide. Typical adult IV doses of ibutilide are in the range of about 1-2 mg.

Another antiarrhythmic, dofetilide, is a Class III antiarrhythmic agent represented by the following structural formula:

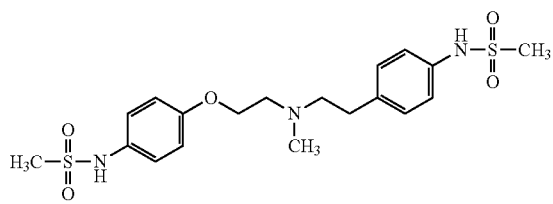

The mechanism of action for dofetilide is through blocking cardiac ion channels of the rapid component of the delayed rectifier potassium current Ikr. The agent, a sulfonamide, is approved to treat atrial fibrillation and atrial flutter. Dofetilide may additionally be useful for hospitalized people with atrial fibrillation cardioverted to normal sinus rhythm, without ventricular arrhythmias or various forms of blocks, in patients with normal kidney function. Dofetilide normalizes sinus rhythm by prolonging cardiac action potential duration and effective refractory period due to delayed repolarization without affecting conduction velocity. Dofetilide is currently approved in the United States for oral administration (under the brand name TIKOSYN®, Pfizer Inc.). Typical oral doses of dofetilide are in the range of 125-500 mcg (twice daily), while intravenous doses can be in the range of about 0.1 mcg/kg to 3 mcg/kg or more.

Amiodarone (for example, amiodarone hydrochloride: 2-butyl-3-benzafuranyl)[4-[2-(diethylamino)ethoxy]-3,5-diiodophenyl]-methanone hydrochloride) is also a Class III antiarrhythmic drug and is represented by the following structural formula:

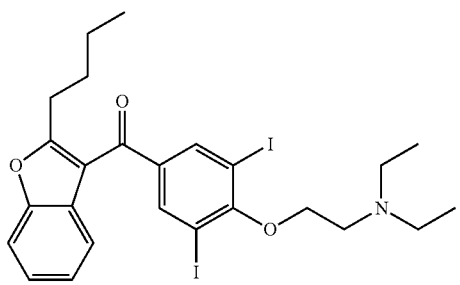 [SMILES: CCCCc1oc2ccccc2c1C(=O)c1cc(I)c(OCCN(CC)CC)c(I)c1]

Amiodarone is used for the treatment of life-threatening recurrent VF or life-threatening recurrent hemodynamically unstable VT and is usually used for patients who are intolerant to or who may not respond adequately to other antiarrhythmic drugs. It is currently approved in the United States for both oral and intravenous administration and is marketed under brand names including CORDARONE®, PACERONE®, and NEXTERONE®. Typical doses for oral amiodarone are in the range of 100-400 mg, with a loading dose of 800-1600 mg/day and a maintenance dose of 600-800 mg/day tapering off to 400 mg/day, while intravenous dosing of amiodarone is in the range of 150-540 mg.

Dronedarone (400 mg tablets, typically administered twice daily) is used for the treatment of paroxysmal or persistent atrial fibrillation or atrial flutter and can be used with patients who have experienced a recent AF/AFL episode who are in sinus rhythm or who will be cardioverted. Dronedarone is marketed under the brand name MULTAQ® (Sanofi Aventis) and has the following structural formula:

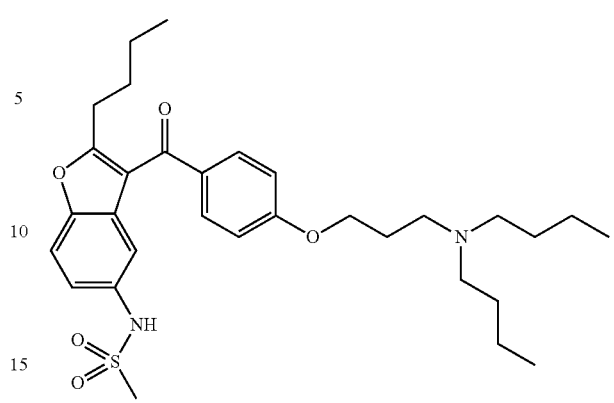

Flecainide is a Class IC drug used for the treatment of ventricular tachycardia, atrial fibrillation, atrial flutter, Wolff-Parkinson-White syndrome and paroxysmal supraventricular tachycardia and is represented by the following structural formula:

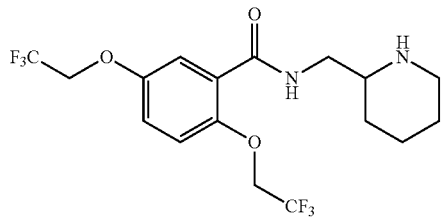 [SMILES: O=C(NCC1CCCCN1)c1cc(OCC(F)(F)F)ccc1OCC(F)(F)F]

Flecainide is typically administered to adults starting with 50-100 mg (twice a day) with the maximum recommended dose being 400 mg/day and is sold under the brand name TAMBOCOR® (3M Pharmaceuticals). Renal and liver adjustments may be needed in some cases.

Procainamide is typically administered in oral doses of 1500-2500 mg (twice daily) to adults and for intravenous doses in the range of 15-18 mg/kg or 100 mg, and up to a total of 1 gram/day. For patients with low renal or liver clearance abilities, adjustments are recommended. Procainamide is marketed under the brand names including PRONESTYL®, PRONESTYL-SR®, PROCAN SR®, and PROCANBID®.

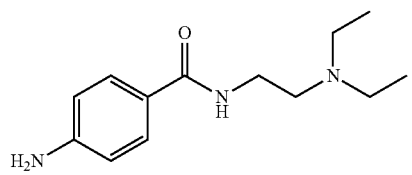 [SMILES: CCN(CC)CCNC(=O)c1ccc(N)cc1]

Propafenone (RHTHMOL®, RYTHMOL SR®) is used for the treatment of atrial fibrillation, atrial flutter, ventricular tachycardia and paroxysmal supraventricular tachycardia. A typical adult oral dose is in the range of about 150-425 mg, such as 150 mg at 8 hour intervals with a maximum dose of 800 mg/day. Adjustments, such as dose reduction, may be needed for patients with renal or liver clearance difficulty.

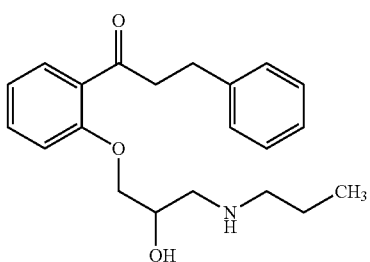 [SMILES: CCCNCC(O)COc1ccccc1C(=O)CCc1ccccc1]

More specific dosing information, mechanisms of action, contraindications, adverse effects, drug interactions, if any, renal and/or liver clearance thresholds, if applicable, etc. for various antiarrhythmic drugs can be found in the following product labels: (1) Amiodarone HCl injection for intravenous use [package insert], Lake Forest, IL: Hospira, Inc.; Initial U.S. Approval: 1995; (2) Cordarone® (amiodarone HCl) Tablets [package insert], Philadelphia, PA: Wyeth Pharmaceuticals Inc.; 2004; (3) TIKOSYN® (dofetilide) Capsules [package insert], NY, NY: Pfizer Inc.; 2014; (4) MULTAQ (dronedarone) tablets, for oral use [package insert], Bridgewater, NJ: Sanofi-Aventis U.S. LLC; 2020; (5) FLECAINIDE ACETATE TABLETS, USP [package insert], Jacksonville, FL: Ranbaxy Pharmaceuticals Inc.; 2003; (6) IBUTILIDE FUMARATE INJECTION [package insert], Morgantown, WV: Mylan Institutional LLC; 2020; (7) PROCAINAMIDE HYDROCHLORIDE Injection, USP [package insert], Lake Forest, IL: Hospira, Inc.; 2021; (8) RYTHMOL (propafenone hydrochloride tablets), for oral use [package insert], Research Triangle Park, NC: GlaxoSmithKline; 2018. Each of these product labels is hereby incorporated by reference herein in its entirety.

SUMMARY

Described herein are methods of administering one or more antiarrhythmic drug, such as a Class I, Class II or Class III antiarrhythmic drug, such as sotalol, dofetilide, amiodarone, ibutilide, dronedarone, procainamide, flecainide, or propafenone, to a patient in need thereof in an amount effective for treating a cardiovascular condition of the patient, such as atrial fibrillation (AFIB); atrial flutter (AF or AFL); ventricular tachycardia; hemodynamically stable or unstable ventricular tachycardia (VT); ventricular fibrillation (VF); paroxysmal supraventricular tachycardia; paroxysmal atrial fibrillation; heart failure; coronary artery disease; pulmonary artery hypertension; maintenance of normal sinus rhythm (delay in time to recurrence of atrial fibrillation/atrial flutter (AFIB/AFL)) for example in patients with symptomatic AFIB/AFL and/or who are currently in sinus rhythm, and/or indicated for the treatment of life-threatening ventricular tachycardia; and/or treating people, such as hospitalized people, with atrial fibrillation cardioverted to normal sinus rhythm, without ventricular arrhythmias or various forms of blocks, in patients with normal kidney function; treating life-threatening recurrent VF or life-threatening recurrent hemodynamically unstable VT; treating paroxysmal or persistent atrial fibrillation or atrial flutter, such as with patients who have experienced a recent AF/AFL episode who are in sinus rhythm or who will be cardioverted; and/or treating Wolff-Parkinson-White syndrome and/or paroxysmal supraventricular tachycardia.

In one implementation, a method of administering an antiarrhythmic drug includes i) prompting input relating to one or more health characteristics of a patient and relating to one or more antiarrhythmic drug (oral and/or IV) dosing characteristics/history of the patient, including one or more or any combination of patient's age, patient's weight, sex of patient, patient's heart rate, patient's blood pressure, patient's temperature, patient's creatinine clearance, patient's renal or liver function, patient's cardiovascular condition, patient's medications, amount of current and/or previous and/or target oral or IV maintenance dose, time from or time of last oral or IV maintenance dose, current or previous antiarrhythmic drug administered, and/or desired/target antiarrhythmic drug to be administered or switched to;

ii) determining drug appropriateness for the patient, an amount of an IV loading dose, a time for administering of (or any minimum delay from completion of the IV loading dose to) a first oral or IV maintenance dose, and/or an oral or IV maintenance dosing interval based on the input, a target oral maintenance dose, whether the patient is being initiated or escalated on the drug, and outputting a drug dosing protocol for the patient based on the drug appropriateness for the patient, the patient's creatinine clearance, the patient's renal or liver function, the patient's cardiovascular condition, the patient's medications, the amount of the IV loading dose, a time for administering of (or any minimum delay to) the first oral dose, the oral dosing interval, and the target amount of the maintenance oral dose based on the determining.

Embodiments include a method of administering sotalol, such as sotalol hydrochloride, the method comprising: i) prompting input relating to one or more health characteristics of a patient and sotalol oral and/or IV dosing characteristics/history of the patient, including one or more or any combination of patient's QT interval or QTc, patient's creatinine clearance, amount of current and/or previous and/or target oral or IV sotalol maintenance dose, projected start time for infusion, whether the patient is being initiated on or escalated to a higher oral dose of sotalol hydrochloride, time from or time of last oral sotalol maintenance dose, current or previous antiarrhythmic drug administered;

ii) determining sotalol appropriateness for the patient, an amount of an IV sotalol loading dose, a time for administering of (or any minimum delay from completion of the IV loading dose to) a first sotalol oral or IV maintenance dose, and/or oral or IV dosing interval between sotalol maintenance doses based on the input, a target oral or IV sotalol maintenance dose, and outputting a sotalol dosing protocol for the patient based on any one or more or all of the sotalol appropriateness for the patient, the patient's creatinine clearance, the patient's renal function, the patient's cardiovascular condition, the IV sotalol loading dose, a time for administering of a first oral sotalol maintenance dose (or any minimum delay to the first sotalol oral or IV maintenance dose from completion of the IV loading dose), the sotalol oral or IV maintenance dosing interval, and the target amount of the maintenance sotalol oral or IV dose based on the determining.

Embodiments include a method of administering dofetilide, the method comprising: i) prompting input relating to one or more health characteristics of a patient and dofetilide oral and/or IV dosing characteristics/history of the patient, including one or more or any combination of patient's age, patient's weight, sex of patient, patient's heart rate, patient's blood pressure, patient's temperature, patient's creatinine clearance, patient's renal function, patient's cardiovascular condition, patient's medications, amount of current and/or previous and/or target oral or IV dofetilide maintenance dose, a projected start time for infusion, whether the patient is being initiated on or escalated to a higher oral dofetilide dose, time from or time of last oral or IV dofetilide maintenance dose, current or previous antiarrhythmic drug administered;

ii) determining any one or more of or all of dofetilide appropriateness for the patient, an amount of an IV dofetilide loading dose, a time for administering of (or any minimum delay to) a first dofetilide oral or IV maintenance dose, and/or oral or IV dosing interval between maintenance dofetilide doses based on the input, an amount of a target oral or IV dofetilide maintenance dose, and outputting a dofetilide dosing protocol for the patient based on any one or more of or all of the dofetilide appropriateness for the patient, the patient's creatinine clearance, the patient's renal function, the patient's cardiovascular condition, the patient's medications, the amount of the IV dofetilide loading dose or start time for infusion, a time for administering of (or any minimum delay to) the first dofetilide oral or IV maintenance dose, the dofetilide oral or IV maintenance dosing interval, and the target amount of the maintenance dofetilide oral or IV dose based on the determining.

The methods can be effectuated through software steps performed by a computer processor and other computer components. Additional implementations include as components of the system one or more of a computer, computing device, or medical device, such as an EKG measuring device, and/or combinations thereof forming a system, designed or configured and connected together in a manner to communicate with and/or control components of the system to perform one or more steps of the method implementations. Additional implementations include a non-transitory computer-readable storage medium comprising computer-readable code, computer-readable instructions, computer-executable instructions, or "software" stored thereon capable of performing one or more steps of the method implementations. More specific implementations of the preceding and their features are provided in the Drawings and the Detailed Description.

According to some advantages, the implementations provide an intravenous loading dose for sotalol, dofetilide, amiodarone, ibutilide, dronedarone, procainamide, flecainide, and/or propafenone that is expected to achieve steady state concentration faster compared to conventional oral dosing for these antiarrhythmics. As such, the implementations can reduce the length of hospitalization and QTc monitoring required in comparison to conventional oral dosing, and allow a health care provider to safely and efficaciously administer one or more antiarrhythmic drug, or switch from one antiarrhythmic drug to another, in a manner which minimizes the potential for concentration-dependent adverse effects such as ventricular arrhythmias (e.g. Torsade de Pointes).

More specific aspects of embodiments of the invention include:

Aspect A, which is a treatment management application configured to perform a set of operations comprising: (i) reading, prompting input of and/or accepting the following as inputs: a projected start time for sotalol hydrochloride infusion; a creatinine clearance (CrCl) rate or creatinine level of a subject; whether the subject is being initiated or escalated on the sotalol hydrochloride; and an amount of an oral target dosage of sotalol hydrochloride for the subject; and (ii) executing computer executable instructions to derive from a set of rules a sotalol hydrochloride dosing protocol for the subject based on the inputs, the dosing protocol comprising: an amount of the sotalol hydrochloride for infusion as a loading dose; optionally a time for administering a first oral dose of sotalol hydrochloride; optionally a time for administering a second oral dose of sotalol hydrochloride or an oral maintenance dosing interval; and (iii) outputting the sotalol hydrochloride dosing protocol. In any of the embodiments described herein, the accepting of any one or more of the inputs, such as creatinine clearance, QT interval or QTc, can be provided automatically by a monitoring and/or measuring device or system for collecting such patient information from the patient/subject.

Aspect B is the treatment management application of Aspect A, wherein the set of rules is based on criteria set forth in Table 1 (below).

Aspect C is the treatment management application of Aspect A or B, wherein: for the subject who has a CrCl of >90 mL/min and is being initiated on an 80 mg target oral sotalol hydrochloride dose, the dosing protocol comprises: 60 mg as the amount for infusion as the IV loading dose; a time of at least 4 hours after completion of the loading dose as the time for administering the first oral dose; and a time of 12 hours after the first oral dose as the time for administering the second or subsequent oral dose(s).

Aspect D is the treatment management application of any of Aspects A-C, wherein: for the subject who has a CrCl of 60-90 mL/min and is being initiated on an 80 mg target oral sotalol hydrochloride dose, the dosing protocol comprises: 82.5 mg as the amount for infusion as the IV loading dose; a time of at least 4 hours after completion of the loading dose as the time for the first oral dose; and a time of 12 hours after the first oral dose as the time for the second oral dose.

Aspect E is the treatment management application of any of Aspects A-D, wherein: for the subject who has a CrCl of 30-60 mL/min and is being initiated on an 80 mg target oral sotalol hydrochloride dose, the dosing protocol comprises: 75 mg as the amount for infusion as the loading dose; a time of at least 6 hours after completion of the loading dose as the time for the first oral dose; and a time of 24 hours after the first oral dose as the time for the second oral dose.

Aspect F is the treatment management application of any of Aspects A-E, wherein: for the subject who has a CrCl of 10-30 mL/min and is being initiated on an 80 mg target oral sotalol hydrochloride dose, the dosing protocol comprises: 75 mg as the amount for infusion as the loading dose; a time of at least 12 hours after completion of the loading dose as the time for the first oral dose; and a time of 48 hours after the first oral dose as the time for the second oral dose.

Aspect G is the treatment management application of any of Aspects A-F, wherein: for the subject who has a CrCl of >90 mL/min and is being initiated on an 120 mg target oral sotalol hydrochloride dose, the dosing protocol comprises: 75 mg as the amount for infusion as the loading dose; a time of at least 4 hours after completion of the loading dose as the time for the first oral dose; and a time of 12 hours after the first oral dose as the time for the second oral dose.

Aspect H is the treatment management application of any of Aspects A-G, wherein: for the subject who has a CrCl of 60-90 mL/min and is being initiated on an 120 mg target oral sotalol hydrochloride dose, the dosing protocol comprises: 82.5 mg as the amount for infusion as the loading dose; a time of at least 4 hours after completion of the loading dose as the time for the first oral dose; and a time of 12 hours after the first oral dose as the time for the second oral dose.

Aspect I is the treatment management application of any of Aspects A-H, wherein: for the subject who has a CrCl of 30-60 mL/min and is being initiated on an 120 mg target oral sotalol hydrochloride dose, the dosing protocol comprises: 82.5 mg as the amount for infusion as the loading dose; a time of at least 6 hours after completion of the loading dose as the time for the first oral dose; and a time of 24 hours after the first oral dose as the time for the second oral dose.

Aspect J is the treatment management application of any of Aspects A-I, wherein: for the subject who has a CrCl of 10-30 mL/min and is being initiated on an 120 mg target oral sotalol hydrochloride dose, the dosing protocol comprises: 82.5 mg as the amount for infusion as the loading dose; a time of at least 12 hours after completion of the loading dose as the time for the first oral dose; and a time of 48 hours after the first oral dose as the time for the second oral dose.

Aspect K is the treatment management application of any of Aspects A-J, wherein: for the subject who has a CrCl of >90 mL/min and is being escalated from an oral dose of 80 mg to a target oral sotalol hydrochloride dose of 120 mg, the dosing protocol comprises: 90 mg as the amount for infusion as the loading dose; a time of at least 4 hours after completion of the loading dose as the time for the first oral dose; and a time of 12 hours after the first oral dose as the time for the second oral dose.

Aspect L is the treatment management application of any of Aspects A-K, wherein: for the subject who has a CrCl of 60-90 mL/min and is being escalated from an oral dose of 80 mg to a target oral sotalol hydrochloride dose of 120 mg, the dosing protocol comprises: 125 mg as the amount for infusion as the loading dose; a time of at least 4 hours after completion of the loading dose as the time for the first oral dose; and a time of 12 hours after the first oral dose as the time for the second oral dose.

Aspect M is the treatment management application of any of Aspects A-L, wherein: for the subject who has a CrCl of 30-60 mL/min and is being escalated from an oral dose of 80 mg to a target oral sotalol hydrochloride dose of 120 mg, the dosing protocol comprises: 112.5 mg as the amount for infusion as the loading dose; a time of at least 6 hours after completion of the loading dose as the time for the first oral dose; and a time of 24 hours after the first oral dose as the time for the second oral dose.

Aspect N is the treatment management application of any of Aspects A-M, wherein: for the subject who has a CrCl of 10-30 mL/min and is being escalated from an oral dose of 80 mg to a target oral sotalol hydrochloride dose of 120 mg, the dosing protocol comprises: 112.5 mg as the amount for infusion as the loading dose; a time of at least 12 hours after completion of the loading dose as the time for the first oral dose; and a time of 48 hours after the first oral dose as the time for the second oral dose.

Aspect O is the treatment management application of any of Aspects A-N, wherein: for the subject who has a CrCl of >90 mL/min and is being escalated from an oral dose of 120 mg to a target oral sotalol hydrochloride dose of 160 mg, the dosing protocol comprises: 90 mg as the amount for infusion as the loading dose; a time of at least 4 hours after completion of the loading dose as the time for the first oral dose; and a time of 12 hours after the first oral dose as the time for the second oral dose.

Aspect P is the treatment management application of any of Aspects A-0, wherein: for the subject who has a CrCl of 60-90 mL/min and is being escalated from an oral dose of 120 mg to a target oral sotalol hydrochloride dose of 160 mg, the dosing protocol comprises: 105 mg as the amount for infusion as the loading dose; a time of at least 4 hours after completion of the loading dose as the time for the first oral dose; and a time of 12 hours after the first oral dose as the time for the second oral dose.

Aspect Q is the treatment management application of any of Aspects A-P, wherein: for the subject who has a CrCl of 30-60 mL/min and is being escalated from an oral dose of 120 mg to a target oral sotalol hydrochloride dose of 160 mg, the dosing protocol comprises: 105 mg as the amount for infusion as the loading dose; a time of at least 6 hours after completion of the loading dose as the time for the first oral dose; and a time of 24 hours after the first oral dose as the time for the second oral dose.

Aspect R is the treatment management application of any of Aspects A-Q, wherein: for the subject who has a CrCl of 10-30 mL/min and is being escalated from an oral dose of 120 mg to a target oral sotalol hydrochloride dose of 160 mg, the dosing protocol comprises: 105 mg as the amount for infusion as the loading dose; a time of at least 12 hours after completion of the loading dose as the time for the first oral dose; and a time of 48 hours after the first oral dose as the time for the second oral dose.

Aspect S is a system for administering intravenous sotalol hydrochloride into a body of a subject, the system comprising: a control module and/or an infusion pump; the treatment management application of any of any of Aspects A-R; wherein the control module and/or the infusion pump are in operable communication with the treatment management application in a manner configured for receiving the amount of the loading dose and the start time for the infusion for administering the sotalol hydrochloride intravenously to the subject.

Aspect T is a method of treating a subject comprising: administering sotalol hydrochloride to a subject based on outputs from the treatment management application of any of any of Aspects A-R and/or using the system of Aspect S; and optionally administering sotalol hydrochloride in a manner for providing for maintenance of normal sinus rhythm (delay in time to recurrence of atrial fibrillation/atrial flutter (AFIB/AFL)) for example in patients with symptomatic AFIB/AFL and/or who are currently in sinus rhythm.

Aspect U is a medical device comprising software stored on or otherwise accessible to (such as through networking and/or cloud computing) an electronic device, such as a laptop or desktop computer or a handheld or wearable electronic device, configured to host any of the treatment management applications of Aspects A-R, including configured to (i) read, prompt input of and/or accept as inputs: a creatinine clearance (CrCl) rate of a subject; whether the subject is being initiated on or escalated to a higher oral dose of sotalol hydrochloride; an amount of an oral target dosage of sotalol hydrochloride for the subject; and optionally a projected start time for sotalol hydrochloride infusion; and (ii) execute computer executable instructions to derive from a set of rules (e.g., rules based on criteria set forth in Table 1) a sotalol hydrochloride dosing protocol for the subject based on the inputs, the dosing protocol comprising: at least an amount of the sotalol hydrochloride for infusion as a loading dose; and optionally a time for administration of a first oral dose of sotalol hydrochloride, optionally relative to the infusion start time; and optionally a time for administration of a second or subsequent oral dose(s) of sotalol hydrochloride, optionally relative to the time of the first oral dose; and (iii) output the sotalol hydrochloride dosing protocol, optionally displayed to a user of the medical device.

Aspect 1: A method comprising: i) prompting input of a baseline QTc value and optionally one or more additional health characteristics of a patient; ii) determining whether the inputted baseline QTc value exceeds a threshold QTc value, and, based on the determining: a) if the inputted baseline QTc value exceeds the threshold QTc value, then outputting a message that one or more antiarrhythmic drug is not recommended for the patient, or b) if the inputted baseline QTc value does not exceed the threshold QTc value, then: iii) prompting input of a creatinine clearance, any current antiarrhythmic drug oral or IV maintenance dose, and target antiarrhythmic drug oral or IV maintenance dose of a patient, including whether the patient is being initiated on the drug or escalated to a higher oral dose; iv) determining an IV loading dose, a time for administering of or any minimum delay to a first oral or IV maintenance dose, and/or an oral or IV maintenance dosing interval based on the inputted creatinine clearance, current oral or IV dose, whether the patient is being initiated or escalated, and the target oral or IV dose; and v) outputting the determined IV loading dose, a time for administering or any minimum delay to first oral or IV maintenance dose, and/or oral or IV dosing interval.

Aspect 2: A method comprising: i) prompting input of one or more health characteristics of a patient and one or more current or previous antiarrhythmic oral or IV dosing characteristics of the patient; ii) determining appropriateness of the antiarrhythmic drug for the patient, an IV loading dose, any minimum delay to first oral or IV maintenance dose, and/or oral or IV maintenance dosing interval based on the input; iii) outputting a message regarding the drug appropriateness for the patient, IV loading dose, any minimum delay to first oral or IV maintenance dose, and/or oral or IV maintenance dosing interval based on the determining.

Aspect 3: The method of Aspect 1 or 2, wherein the health characteristics of the patient comprise information that can affect one or more pharmacokinetic characteristics or behaviors of the antiarrhythmic drug in the patient.

Aspect 4: The method of any Aspects 1-3, wherein the one or more pharmacokinetic characteristics or behaviors of the antiarrhythmic drug in the patient comprise one or more of clearance, half-life, bioavailability, absorption, $C_{max}$, $T_{max}$, and/or Area under the Curve (AUC).

Aspect 5: The method of any of the above Aspects, wherein the health characteristics comprise any one or more of age, weight, sex or renal function of the patient.

Aspect 6: The method of Aspect 5, wherein the patient renal function is measured by patient creatinine clearance.

Aspect 7: The method of any of the above Aspects, wherein the health characteristics comprise concomitant medications.

Aspect 8: The method of any of the above Aspects, wherein the health characteristics comprise information indicating a potential risk of an adverse effect of the antiarrhythmic drug.

Aspect 9: The method of any of the above Aspects, wherein the adverse effect comprises one or more of proarrhythmia (e.g. Torsade de Pointes (TdP)), bradycardia, sinus pauses or sinus arrest, hypotension, heart failure, negative inotropy, dyspnea, and/or fatigue, or any other adverse effect.

Aspect 10: The method of any of the above Aspects, wherein the information indicating the potential risk of the antiarrhythmic drug adverse effect comprises patient QT interval or QTc.

Aspect 11: The method of any of the above Aspects, wherein the information indicating the potential risk of the antiarrhythmic drug adverse effect comprises concomitant medications.

Aspect 12: The method of any of the above Aspects, wherein the health characteristics comprise information relating to appropriateness of initiation or continuation of the antiarrhythmic drug for that patient.

Aspect 13: The method of any of the above Aspects, wherein the one or more antiarrhythmic drug oral or IV maintenance dosing characteristics comprise a current, previous and/or target patient oral or IV maintenance dose of the antiarrhythmic drug.

Aspect 14: The method of any of the above Aspects, wherein the prompting input step is performed through one or more input-output (I/O) interface on a computer, computing device, or medical device.

Aspect 15: The method of any of the above Aspects, wherein the calculating and determining steps are performed by way of a processor coupled with a memory on a computer, computing device, or medical device which has various IV loading doses, minimum delays to first oral or IV maintenance dose, and/or oral or IV maintenance dosing intervals of the antiarrhythmic drug stored within.

Aspect 16: The method of any of the above Aspects, wherein the IV loading doses, minimum delays to first oral or IV maintenance dose, and/or oral or IV maintenance dosing intervals are stored in a relational database in the memory.

Aspect 17: The method of any of the above Aspects, wherein the IV loading dose(s), minimum delay(s) to first oral or IV maintenance dose, and/or oral or IV maintenance dosing interval(s) are represented in Table 1.

Aspect 18: The method of any of the above Aspects, wherein the IV loading dose(s), minimum delay(s) to first oral dose, and/or oral or IV maintenance dosing interval(s) are stratified according to tiers of creatinine clearance ranges or values and/or or drug initiation or escalation values, such as those represented in Table 1.

Aspect 19: The method of any of the above Aspects, further comprising: i) determining one or more IV loading dose, any minimum delay to first oral or IV maintenance dose, and/or oral or IV maintenance dosing intervals from computer-based simulations incorporating dose-exposure-QTc relationships for the antiarrhythmic drug; ii) storing the determined IV loading dose, any minimum delay to first oral or IV maintenance dose, and/or oral or IV maintenance dosing intervals in a memory on a computer, computing device, or medical device, such as in a relational database; and iii) retrieving one or more stored drug IV loading dose, any minimum delay to first oral or IV maintenance dose, and/or oral or IV maintenance dosing interval values based on one or more of the inputted patient health characteristics and/or drug dosing characteristics.

Aspect 20: The method of any of the above Aspects, wherein the calculating steps are performed by way of one or more mathematical operations programmed on the computer, computing device, or medical device such as multiplication, addition, subtraction, division, logarithmic functions, exponential functions, and/or algorithmic functions.

Aspect 21: The method of any of the above Aspects, wherein the determining steps are performed by retrieving a corresponding IV loading dose, any minimum delay to first oral or IV maintenance dose, and/or oral or IV maintenance dosing interval stored in a database within the memory of the computer, computing device, or medical device based on one or more of the patient health characteristics or drug dosing characteristics inputted.

Aspect 22: The method of any of the above Aspects, wherein the retrieving comprises matching one or more inputted characteristics with values or ranges used to stratify drug IV loading dose, any minimum delay to first oral or IV maintenance dose, and/or oral or IV maintenance dosing interval values.

Aspect 23: The method of any of the above Aspects, wherein the outputting step is performed by way of a visual output device or an auditory output device on a computer, computing device, or medical device.

Aspect 24: The method of any of the above Aspects, wherein the steps of the method are performed on a single computer, computing device, or medical device.

Aspect 25: The method of any of the above Aspects, wherein the steps of the method are performed on a computer system or network comprising multiple computers, computing devices, or medical devices.

Aspect 26: The method of any of the above Aspects, wherein the medical device is capable of measuring patient EKG, such as a 12-lead EKG or a Holter monitor, and one or more steps of the method are performed on the EKG measuring device.

Aspect 27: The method of any of the above Aspects, wherein some steps of the method are performed on the EKG measuring device, and some steps of the method are performed on a computer or computing device.

Aspect 28: The method of any of the above Aspects, wherein all steps of the method are performed on the EKG measuring device.

Aspect 29: A computer, computing device, or medical device, such as an EKG measuring device, designed or configured to perform one or more steps of the method of any of the above Aspects.

Aspect 30: A non-transitory computer-readable storage medium comprising computer-readable code, computer-readable instructions, computer-executable instructions, or software stored thereon capable of performing one or more steps of the method of any of the above Aspects.

Aspect 31: The non-transitory computer-readable storage medium of any of the above Aspects, further comprising data comprising drug IV loading dose, minimum delay to first oral or IV maintenance dose, and/or oral or IV maintenance dosing interval stratified according to tiers of creatinine clearance ranges and/or or initiation or escalation values.

Aspect 32: The non-transitory computer-readable storage medium of any of the above Aspects, wherein the data is represented in Table 1.

Aspect 33: The non-transitory computer-readable storage medium of any of the above Aspects, wherein the data is stored in a relational database.

Aspect 34: A method comprising: i) determining one or more antiarrhythmic drug IV loading dose, minimum delay (if any) to first oral or IV maintenance dose, and/or oral or IV maintenance dosing intervals from computer-based simulations incorporating antiarrhythmic drug dose-exposure-QTc relationships; and ii) storing the determined IV loading dose, minimum delay (if any) to first oral or IV maintenance dose, and/or oral or IV maintenance dosing intervals on a non-transitory computer readable storage medium, such as the non-transitory computer-readable storage medium of any of the above Aspects.

Aspect 35: The method, computer, computing device, medical device, or non-transitory computer-readable storage medium of any preceding Aspect, wherein the drug dose-exposure-QTc relationships are represented within the computer-based simulations by one or more mathematical functions, equations, or algorithms.

Aspect 36: A system for controlling administration of one or more antiarrhythmic drug to a patient, comprising: i) an input/output interface configured to accept and display patient data obtained from user input and/or one or more monitoring device configured to monitor one or more physiological measurement of a patient; ii) a data storage module configured to store the patient data, the one or more physiological measurement of the patient and one or more dosing criteria for administering one or more antiarrhythmic drug to the patient; and iii) one or more control module comprising one or more processor for executing computer-readable instructions for: a) determining an intravenous dose of the antiarrhythmic drug based on one or more of the patient data, one or more of the physiological measurement of the patient, and the dosing criteria; and b) providing instructions for controlling and/or controlling an infusion pump to administer the intravenous dose to the patient. In embodiments, the dosing criteria can be provided from labeling instructions for any antiarrhythmic drug, including those provided in any of the product labels referenced herein.

Aspect 37: A system comprising: i) an input/output interface; ii) a memory configured to store dosing criteria for one or more antiarrhythmic drug and store data relating to a patient; iii) a computer processor operatively connected to the memory configured to analyze the data relating to the patient and identify one or more acceptable IV dose of the antiarrhythmic drug.

Aspect 38: A system comprising: i) an input/output interface; ii) a medical monitoring device configured to monitor one or more physiological measurement of a patient; iii) an infusion pump for administering one or more antiarrhythmic drug to a patient; iv) one or more control module in communication with the medical device and the infusion pump and comprising computer-executable instructions capable of performing the method of any of the above Aspects by receiving data relating to the patient from the medical device, determining a dosing protocol for the patient based on the data relating to the patient and dosing criteria for the antiarrhythmic drug, and instructing the infusion pump to deliver antiarrhythmic drug to the patient according to the dosing protocol.

Aspect 39: A treatment management application configured to run on a mobile device, the treatment management application comprising: i) a first interface configured to accept patient data, optionally from a patient monitor; ii) a second interface invoked in response to submission of the patient data and configured to provide instructions (e.g., computer-executable instructions) for performing a treatment protocol; wherein the treatment management application is configured to perform operations comprising: a) retrieving the patient data; b) accessing drug dosing criteria from the application, a database, a server, the internet or a computer network; c) deriving the treatment protocol based on the patient data and the drug dosing criteria; and d) reporting, displaying or causing execution of the instructions for performing the treatment protocol, optionally causing execution of the instructions by a control module and/or an infusion pump for administering drugs intravenously.

Aspect 40: A system for administering a drug into a body of a patient with the aid of a computer-controlled dosage device, the system comprising: i) one or more patient monitor configured to obtain one or more physiological measurement of the patient; ii) an input/output interface; iii) a processing module configured to perform the following: a) retrieve patient data and the physiological measurements of the patient; b) access stored drug dosing criteria; c) report or display a treatment plan based on the patient data, the physiological measurements of the patient, and the drug dosage criteria; and iii) a control module configured to accept the treatment plan from the processing module and transmit the treatment plan to a computer-controlled dosage device; wherein the computer-controlled dosage device is capable of administering the drug into the body of the patient using an infusion pump according to the treatment plan.

Aspect 41: The system any of the above Aspects, wherein the one or more physiological measurement is chosen from QT interval, QTc, blood pressure, heart rate, or combinations thereof.

Aspect 42: The method of any of the above Aspects, wherein the antiarrhythmic drug is one or more of sotalol, dofetilide, amiodarone, ibutilide, dronedarone, procainamide, flecainide, or propafenone.

Aspect 43: A treatment management application configured to manage treatment of a patient according to the method of any of the Aspects disclosed herein.

Aspect 44: A system for administering a drug into a body of a patient according to any of the methods of any of the Aspects disclosed herein.

Aspect 45: The system or application of any of the Aspects disclosed herein, wherein the patient data comprises one or more of patient age, patient weight, patient sex, patient renal function, such as creatinine clearance (CrCl), patient medication(s), patient heart rate, patient blood pressure, patient temperature, and/or patient cardiovascular condition.

Aspect 46: The system or application of any of the Aspects disclosed herein, wherein the monitoring device, the medical monitoring device, or the patient monitor is capable of measuring patient EKG, such as a 12-lead EKG or a Holter monitor.

Aspect 47: The system or software or mobile application of any of the Aspects disclosed herein, wherein the control module controls the administering by controlling or instructing the infusion pump concerning one or more of a rate of one or more infusion, a time of infusion, or any interval between one or more infusions.

Aspect 48: The system or application of any of the Aspects disclosed herein, wherein the dosing criteria and/or the IV dosing comprise IV loading dose, any minimum delay to first oral or IV maintenance dose, and/or oral or IV maintenance dosing interval.

Aspect 49: The system or application of any of the Aspects disclosed herein, wherein the antiarrhythmic drug is one or more of sotalol, dofetilide, amiodarone, ibutilide, dronedarone, procainamide, flecainide, or propafenone.

Aspect 50, which is the system of Aspect 36, wherein the dosing criteria are selected from one or more criteria from labeling instructions for the antiarrhythmic drug, including labeling instructions for any one or more of sotalol, dofetilide, amiodarone, ibutilide, dronedarone, procainamide, flecainide, or propafenone, such as provided in the product labels referenced herein. For example, dosing criteria for any antiarrhythmic drug can follow any of the flowcharts provided in FIGS. 1-10, modified according to the label for a particular desired drug being administered.

Aspect 51, which is any of the methods, systems or treatment management applications of Aspects 1-50, adapted for treatment of any one or more of atrial fibrillation (AFL); atrial flutter (AF); ventricular tachycardia; hemodynamically stable or unstable ventricular tachycardia (VT); ventricular fibrillation (VF); paroxysmal supraventricular tachycardia; paroxysmal atrial fibrillation; heart failure; coronary artery disease; pulmonary artery hypertension; maintenance of normal sinus rhythm (delay in time to recurrence of atrial fibrillation/atrial flutter (AFIB/AFL)) for example in patients with symptomatic AFIB/AFL and/or who are currently in sinus rhythm, and/or indicated for the treatment of life-threatening ventricular tachycardia; and/or treating people, such as hospitalized people, with atrial fibrillation cardioverted to normal sinus rhythm, without ventricular arrhythmias or various forms of blocks, in patients with normal kidney function; treating life-threatening recurrent VF or life-threatening recurrent hemodynamically unstable VT; treating paroxysmal or persistent atrial fibrillation or atrial flutter, such as with patients who have experienced a recent AF/AFL episode who are in sinus rhythm or who will be cardioverted; and/or treating Wolff-Parkinson-White syndrome and/or paroxysmal supraventricular tachycardia.

BRIEF DESCRIPTION OF THE DRAWINGS

The accompanying drawings illustrate certain aspects and principles of the implementations set forth, and should not be construed as limiting.

DETAILED DESCRIPTION

Reference will now be made in detail to various illustrative implementations. It is to be understood that the following discussion of the implementations is not intended to be limiting.

The following figures depict implementations of various methods represented by flowchart diagrams. To the extent the figures or examples herein may refer to administering sotalol in particular, any antiarrhythmic drug, including additionally dofetilide, amiodarone, ibutilide, dronedarone, procainamide, flecainide, and/or propafenone, can be used instead or in combination with sotalol and the amounts of the IV and/or oral dosages can be adjusted appropriately, for example, adjusted according to the labeling instructions for the particular antiarrhythmic being administered instead of or in addition to sotalol. As can be appreciated, the implementations depicted herein can be combined to be performed serially, and/or in parallel. The implementations can be modified from those depicted in the figures to remove or add one or more steps, change the order of steps, or substitute or exchange one or more steps in a manner that achieves the same effective result. It will be understood that each block of the flowchart diagrams, and combinations of blocks in the flowchart diagrams, can be implemented or supported by computer program instructions. These computer program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart blocks. The method implementations depicted herein can be performed as a series of steps which are implemented as computer-readable code, computer-readable instructions, computer-executable instructions, or "software" performed by one or more processor. Such software can be loaded onto a memory of computer, computing device, medical device, or system thereof, as an application or program capable of performing the steps of the method or otherwise made accessible to such devices through computer networking or cloud computing. Any of the methods can be used with any of the systems described herein and vice versa.

Figure 1:
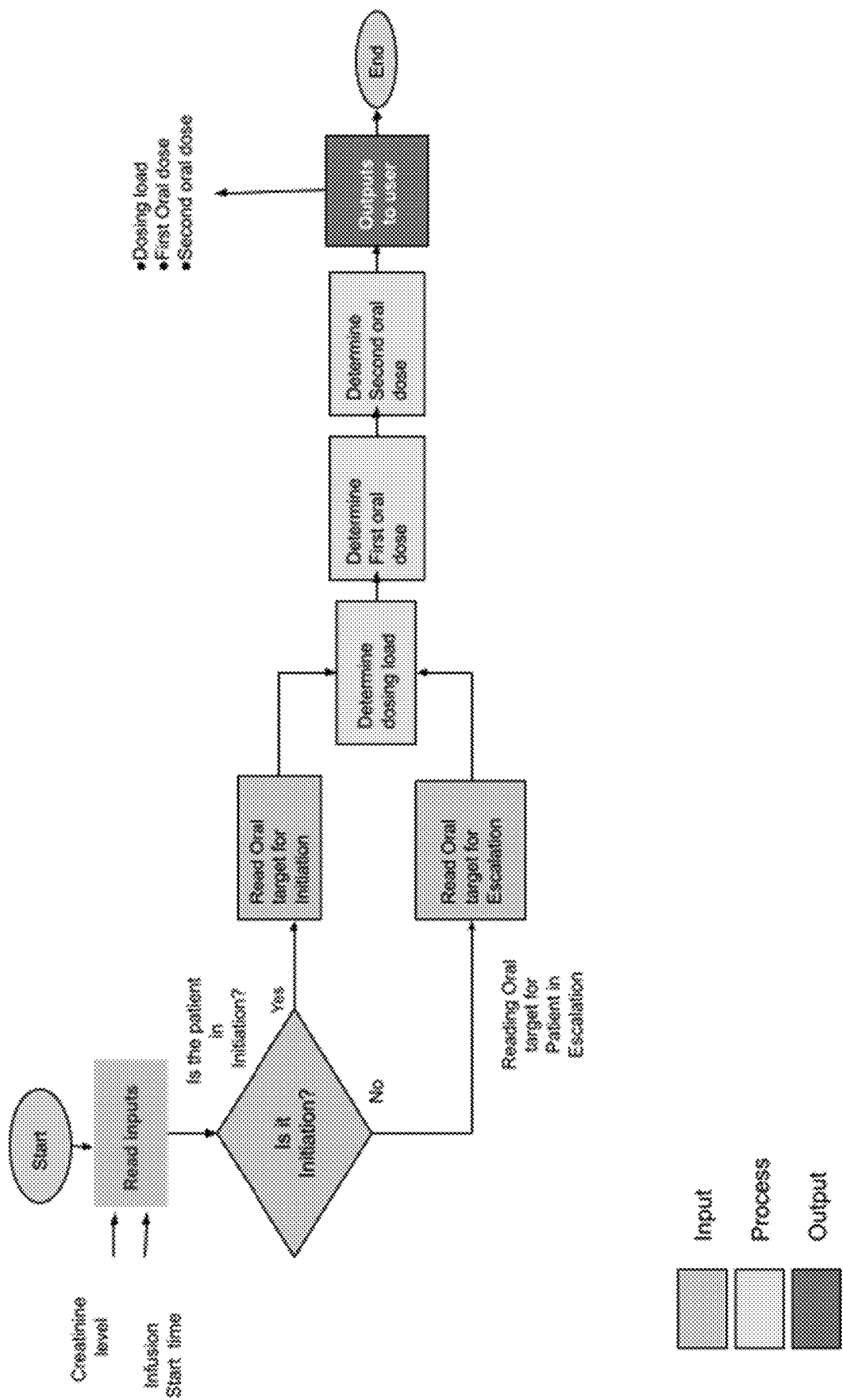
FIG. 1 is a flowchart depicting a method for determining dosing of an antiarrhythmic drug, such as sotalol hydrochloride, e.g., for implementation by a software app.

Embodiments of the invention include software for implementing any of the methods described herein, in whole or part. As shown in FIG. 1, the software application can be configured to receive input regarding a subject's creatinine clearance (CrCl) or creatinine level (which can be used to determine a CrCl) and optionally an estimated start time for dosing to begin, such as a start time for sotalol hydrochloride infusion. In any of the figures or embodiments herein, when referring to CrCl, it is also understood that a creatinine level or serum creatinine of a subject/patient can be used as the input instead or in addition to CrCl. The app is additionally configured to receive input regarding whether the subject is being initiated on the drug or whether the subject's dose is being escalated from one oral dose to a higher target oral dose, and the desired oral target dose, such as for sotalol hydrochloride a target oral dose of 80 mg (initiation), 120 mg (initiation or escalation) or 160 mg (escalation). From the inputs, the software application is configured to determine the amount of an IV loading dose expected to initiate or escalate the subject to the desired target oral dose based on the subject's creatinine clearance (which can be determined by the software application using for example the Cockcroft-Gault formulas for creatine clearance from a serum creatinine level of the patient if used as an input). The software application is further configured to determine when a first oral dose should be administered to the subject, optionally relative to the start time of the IV loading dose (e.g., the estimated start time) based on the subject's creatinine clearance, target oral dose and whether the subject is being initiated or escalated on the drug. The software application is further configured to determine a maintenance dosing interval for the oral dosing based on the target oral dose, the subject's creatinine clearance and whether the subject is being initiated or escalated on the drug. Outputs from the software app can include one or more or all of: (a) a start time for drug infusion to begin and/or end; (b) an amount of drug for administration by way of the IV loading dose or a choice of amounts for the IV infusion, if more than one; (c) an amount of drug for administration by way of oral dosing (e.g., target oral dose); (d) a start time for oral dosing to begin (whether a specific time, such as 9:00 a.m., or an amount of time from completion of the IV dosing, such as at least 4 hours after completion of the infusion); (e) a start time for second and/or subsequent oral doses to begin (whether a specific time or an amount of time following the time of the first oral dose, such as at 12 hour intervals). Optionally, the start time for infusion to begin can be reset and one or more determinations recalculated accordingly. For example, administration of the infusion might actually begin at 9:30 a.m. instead of an expected start time of 9:00 a.m., and the time for the first and/or subsequent oral doses can be redetermined/recalculated (or confirmed, if no change) by the software app accordingly.

FIGS. 2-10 illustrate specific implementations of methods disclosed herein. The implementations exemplified are not limited to sotalol and can be used to determine dosing and administration of any one or more antiarrhythmic drug, including but not limited to sotalol, dofetilide, amiodarone, ibutilide, dronedarone, procainamide, flecainide, or propafenone.

Figure 2:
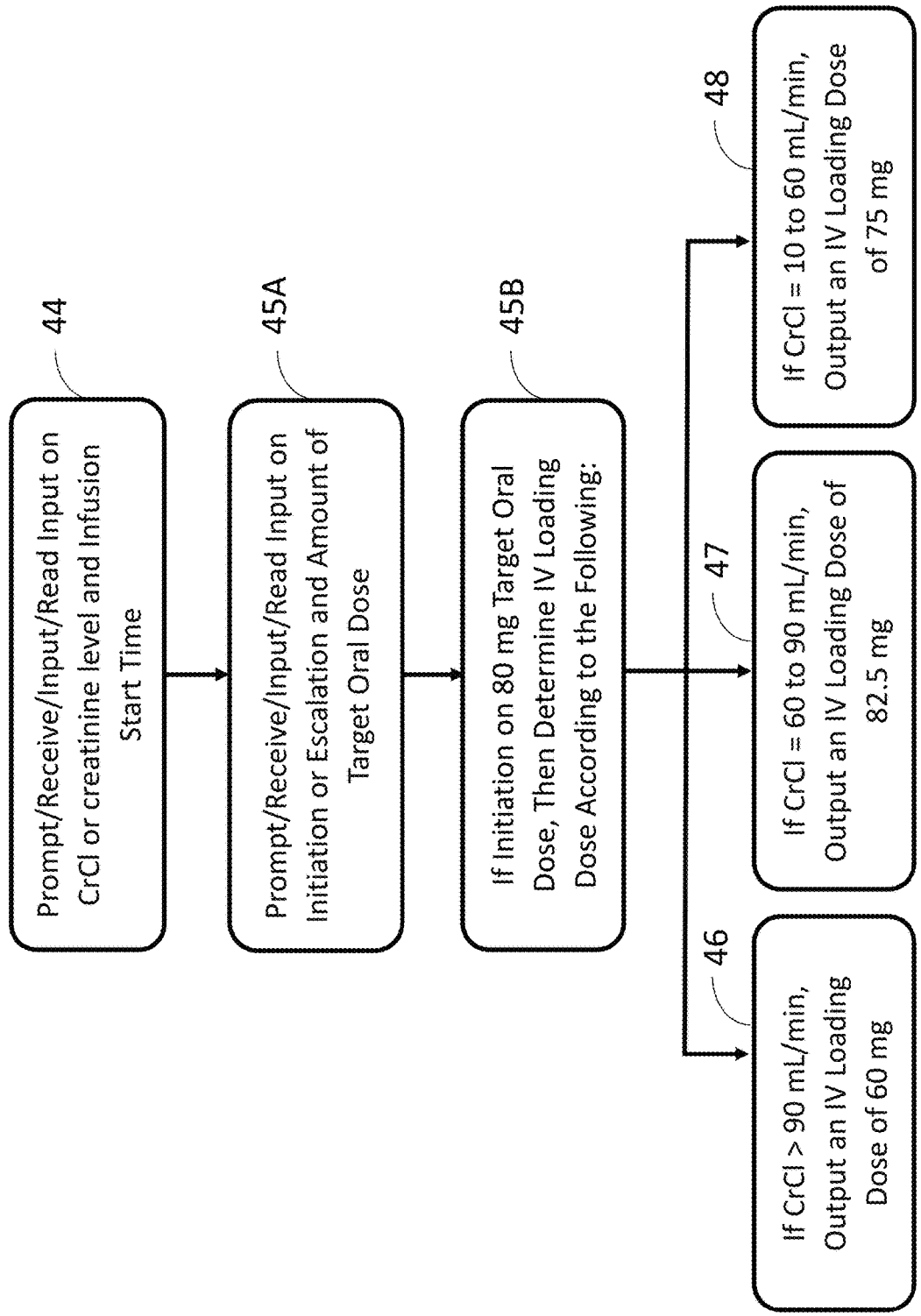
FIG. 2 is a flowchart depicting an exemplary method for determining an IV loading dose for initiation of a subject on a target oral dose of 80 mg sotalol hydrochloride.

One implementation of a method of the invention is shown in FIG. 2, which exemplifies a method relating to initiation of a patient on sotalol hydrochloride of a target oral dose of 80 mg. As shown in FIG. 2, a subject's creatinine clearance and start time for infusion can be input or prompted to be input, read and/or received 44. Inputs also include whether the subject is being initiated on or escalated to a higher target oral dose of the drug and the amount of the target oral dose 45A. For initiation of a subject on an 80 mg target oral dose, the amount of the IV loading dose is determined based on the subject's creatinine clearance and is outputted 45B. For sotalol hydrochloride, for example, if the inputted creatinine clearance exceeds 90 mL/min, then an IV loading dose of 60 mg is outputted 46. If the inputted creatinine clearance is within the range of 60 to 90 mL/min, then an IV loading dose of 82.5 mg is outputted 47. If the inputted creatinine clearance is within the range of 10 to 60 mL/min, then an IV loading dose of 75 mg is outputted 48 or a choice is outputted, such as an IV loading dose of 75 mg or 82.5 mg. IV loading doses for other antiarrhythmics is found in the product labels referenced herein and in some cases may be based on either or both of creatinine clearance and/or liver clearance of the patient.

Figure 3:
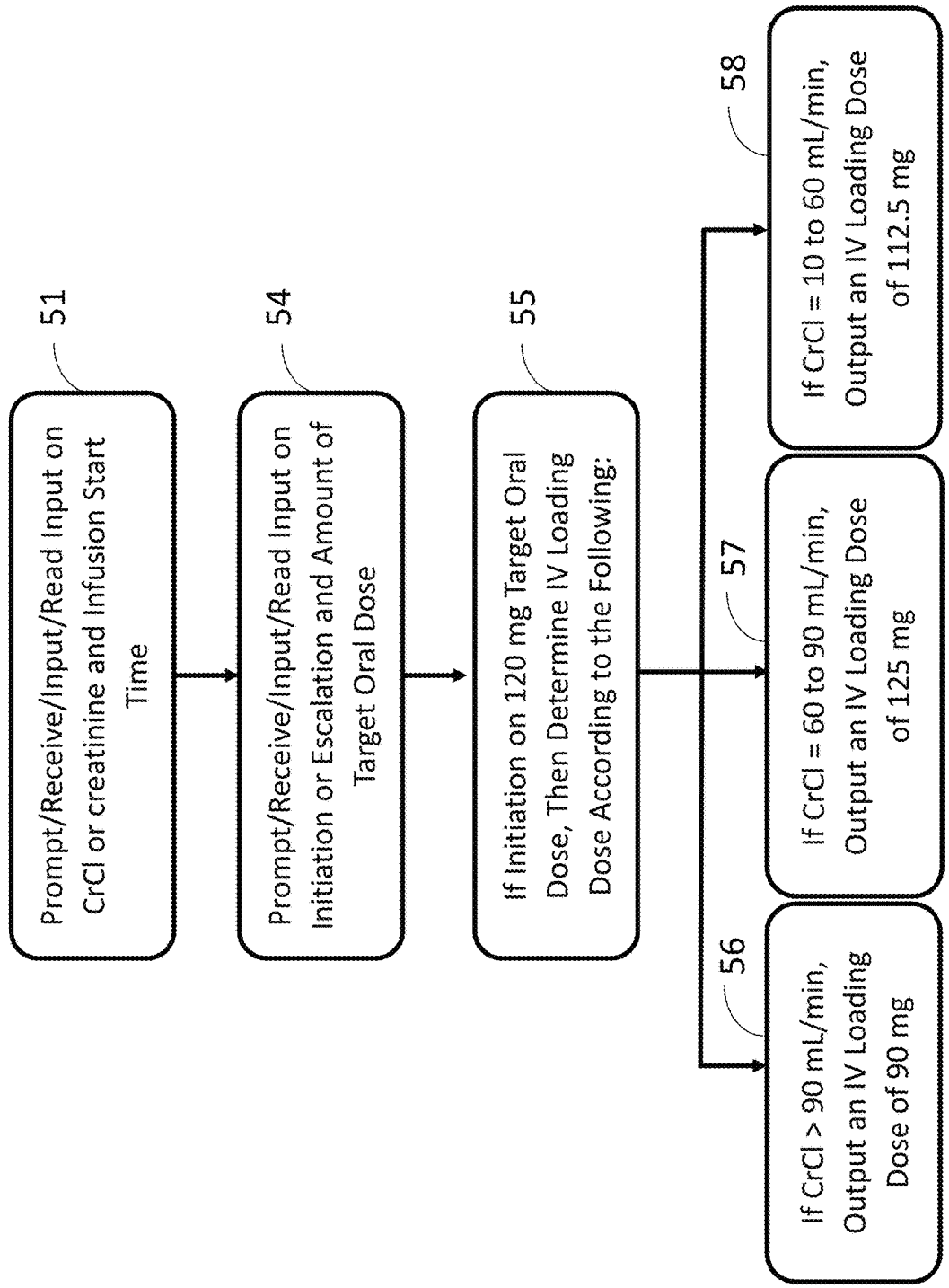
FIG. 3 is a flowchart depicting an exemplary method for determining an IV loading dose for initiation of a subject on a target oral dose of 120 mg sotalol hydrochloride.

Another implementation of a method of the invention is shown in FIG. 3, which exemplifies a method relating to initiation of a patient on sotalol hydrochloride of a target oral dose of 120 mg. As shown in FIG. 3, a subject's creatinine clearance and start time for infusion can be input or prompted to be input, read and/or received 51. Inputs also include whether the subject is being initiated on or escalated to a higher target oral dose of the drug and the amount of the target oral dose 54. For initiation of a subject on a 120 mg target oral dose, the amount of the IV loading dose is determined based on the subject's creatinine clearance and is outputted 55. For sotalol hydrochloride, for example, if the inputted creatinine clearance exceeds 90 mL/min, then an IV loading dose of 90 mg is outputted 56. If the inputted creatinine clearance is within the range of 60 to 90 mL/min, then an IV loading dose of 125 mg is outputted 57. If the inputted creatinine clearance is within the range of 10 to 60 mL/min, then an IV loading dose of 112.5 mg is outputted 58, or a choice of an IV loading dose of 112.5 mg or 125 mg is outputted.

Figure 4:
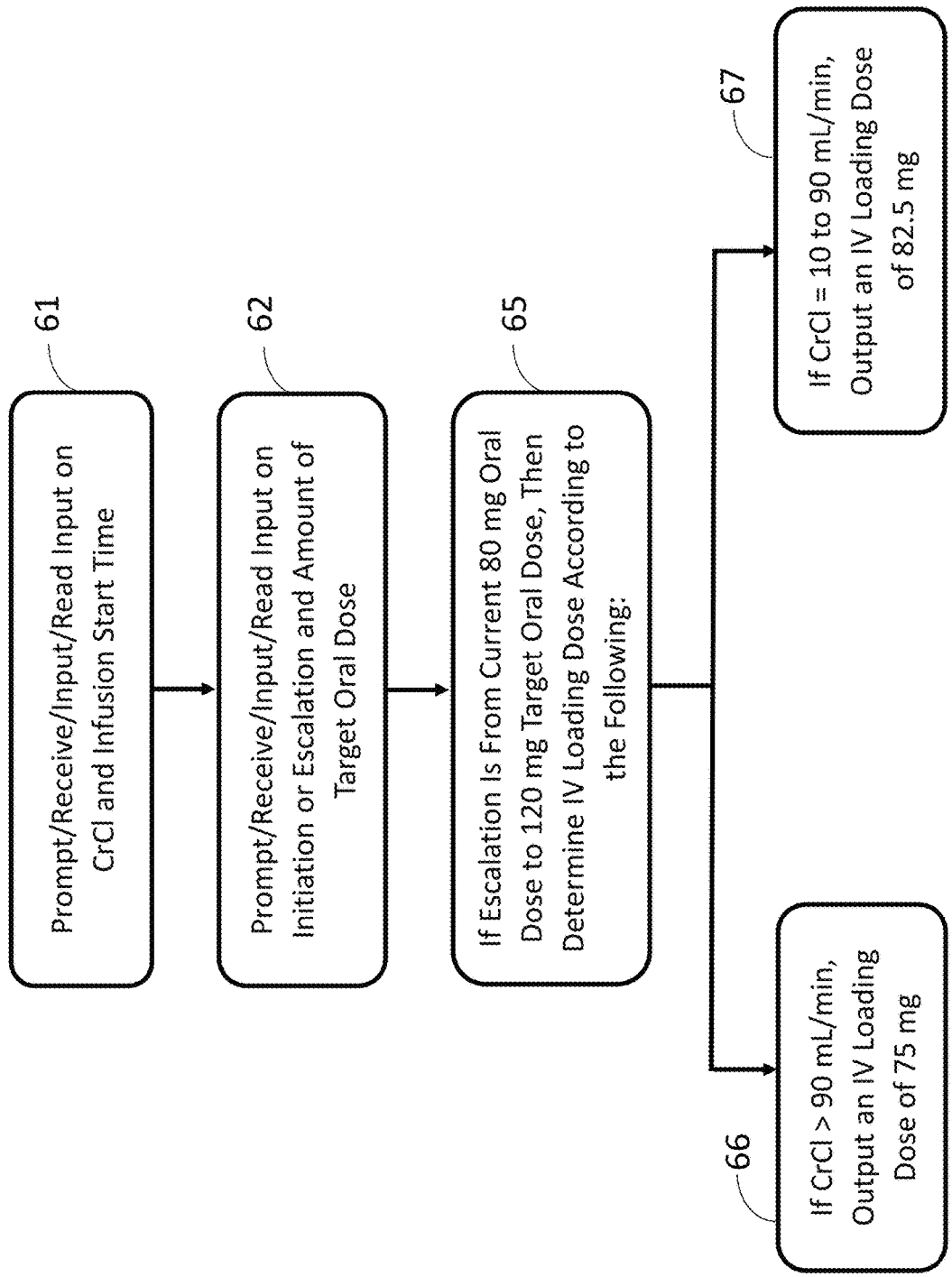
FIG. 4 is a flowchart depicting an exemplary method for determining an IV loading dose for escalation of an 80 mg dose of sotalol hydrochloride up to a target oral dose of 120 mg.

Another implementation of a method of the invention is shown in FIG. 4, which exemplifies a method relating to escalation of a dose of sotalol hydrochloride to a higher target oral dose. As shown in FIG. 4, a subject's creatinine clearance and start time for infusion can be input or prompted to be input, read and/or received 61. Inputs also include whether the subject is being initiated on or escalated to a higher target oral dose of the drug and the amount of the target oral dose 62. For escalation of a subject from a current oral dose of 80 mg to a higher oral dose of 120 mg, the amount of the IV loading dose is determined based on the subject's creatinine clearance and is outputted 65. If the inputted creatinine clearance exceeds 90 mL/min, then an IV loading dose of 75 mg is outputted 66. If the inputted creatinine clearance is within the range of 10 to 90 mL/min, then an IV loading dose of 82.5 mg is outputted 67.

Figure 5:
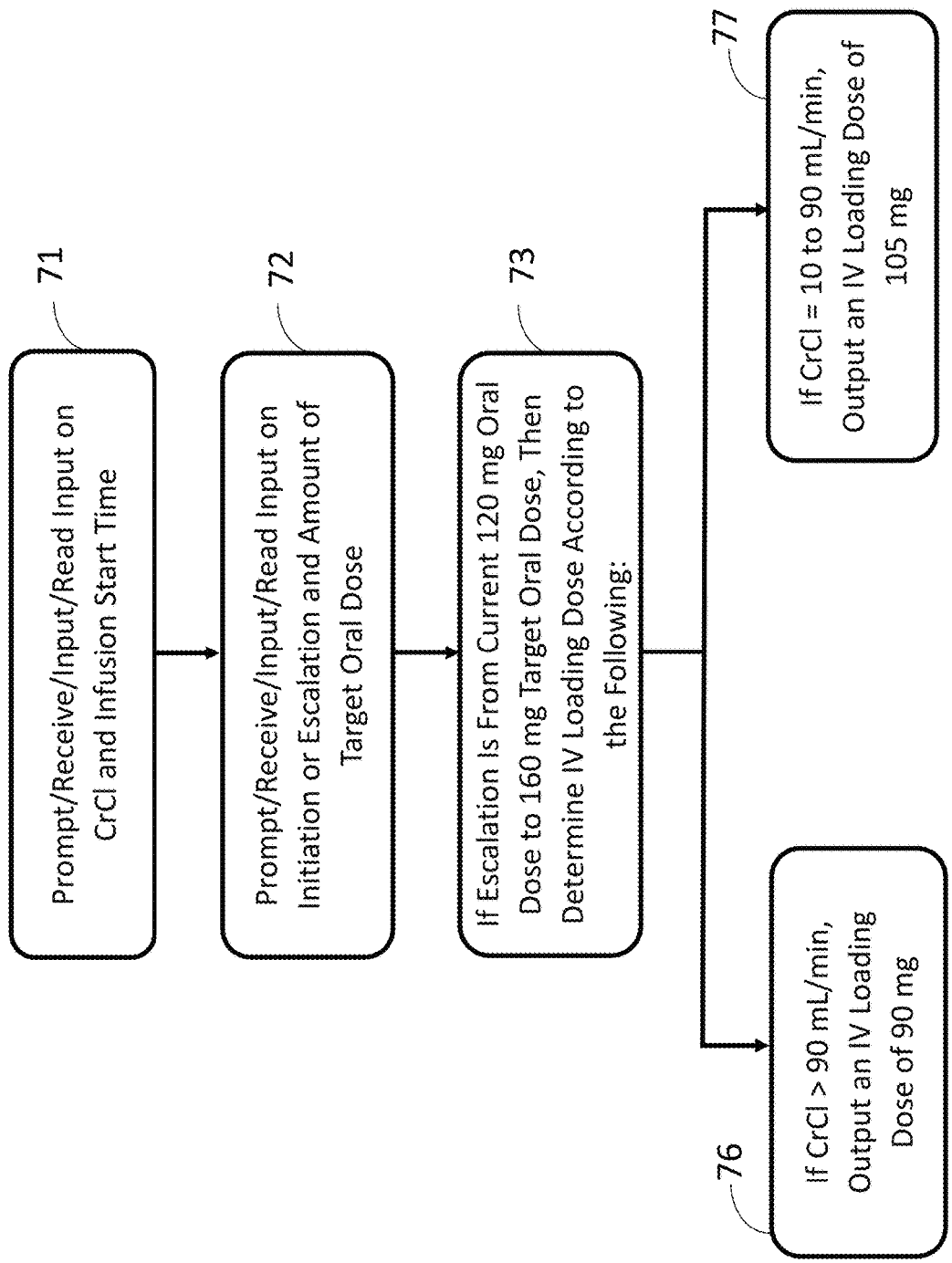
FIG. 5 is a flowchart depicting an exemplary method for determining an IV loading dose for escalation of a 120 mg dose of sotalol hydrochloride up to a target oral dose of 160 mg.

Another implementation of a method of the invention is shown in FIG. 5, which exemplifies a method relating to escalation of a dose of sotalol hydrochloride to a higher target oral dose. As shown in FIG. 5, a subject's creatinine clearance and start time for infusion can be input or prompted to be input, read and/or received 71. Inputs also include whether the subject is being initiated on or escalated to a higher target oral dose of the drug and the amount of the target oral dose 72. For escalation of a subject from a current oral dose of 120 mg to a higher oral dose of 160 mg, the amount of the IV loading dose is determined based on the subject's creatinine clearance and is outputted 73. If the inputted creatinine clearance exceeds 90 mL/min, then an IV loading dose of 90 mg is outputted 76. If the inputted creatinine clearance is within the range of 10 to 90 mL/min, then an IV loading dose of 105 mg is outputted 77.

Figure 6:
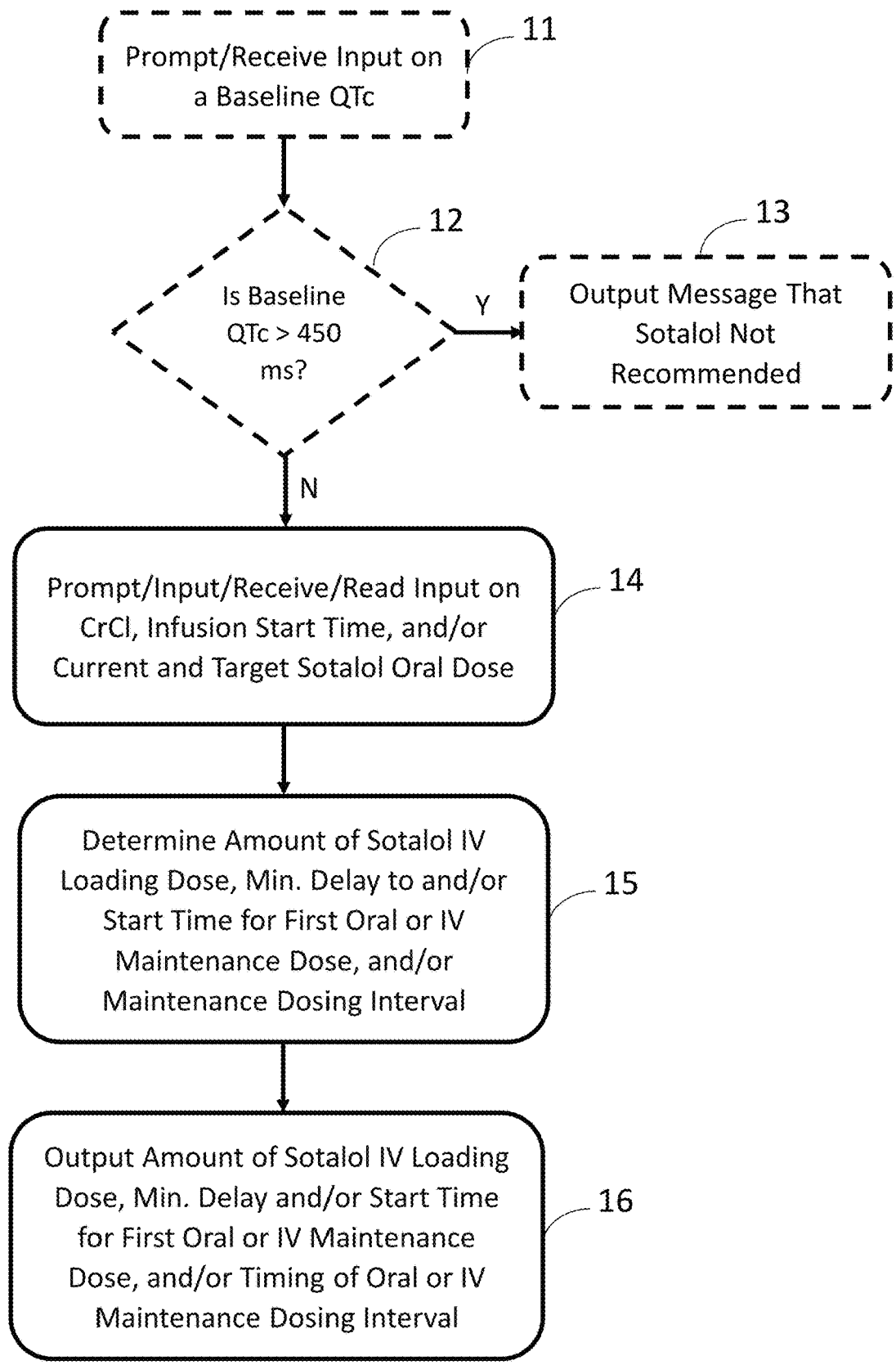
FIG. 6 is a flowchart of an exemplary method for determining an IV loading dose, the minimum delay to a first oral dose and/or a time for maintenance dosing to begin, and the maintenance dosing interval for sotalol hydrochloride.

Another implementation of a method for determining dosing and/or administration of an antiarrhythmic drug is shown in FIG. 6. As shown, a subject's creatinine clearance, start time for infusion and/or current and target oral dose amount can be input or prompted to be input, read and/or received 14. Based on the input of the patient's creatinine clearance or liver clearance, current maintenance oral or IV dose, and target maintenance oral or IV dose, an amount of the IV loading dose, the start time of minimum delay (if any) to the first maintenance dose (e.g., oral or IV dose) and/or the oral or IV dosing interval are determined 15. The determined amount for the IV loading dose, the start time for oral dosing or minimum delay (if any) to first oral dose, and/or the maintenance oral or IV dosing interval are then outputted 16.

Figure 7:
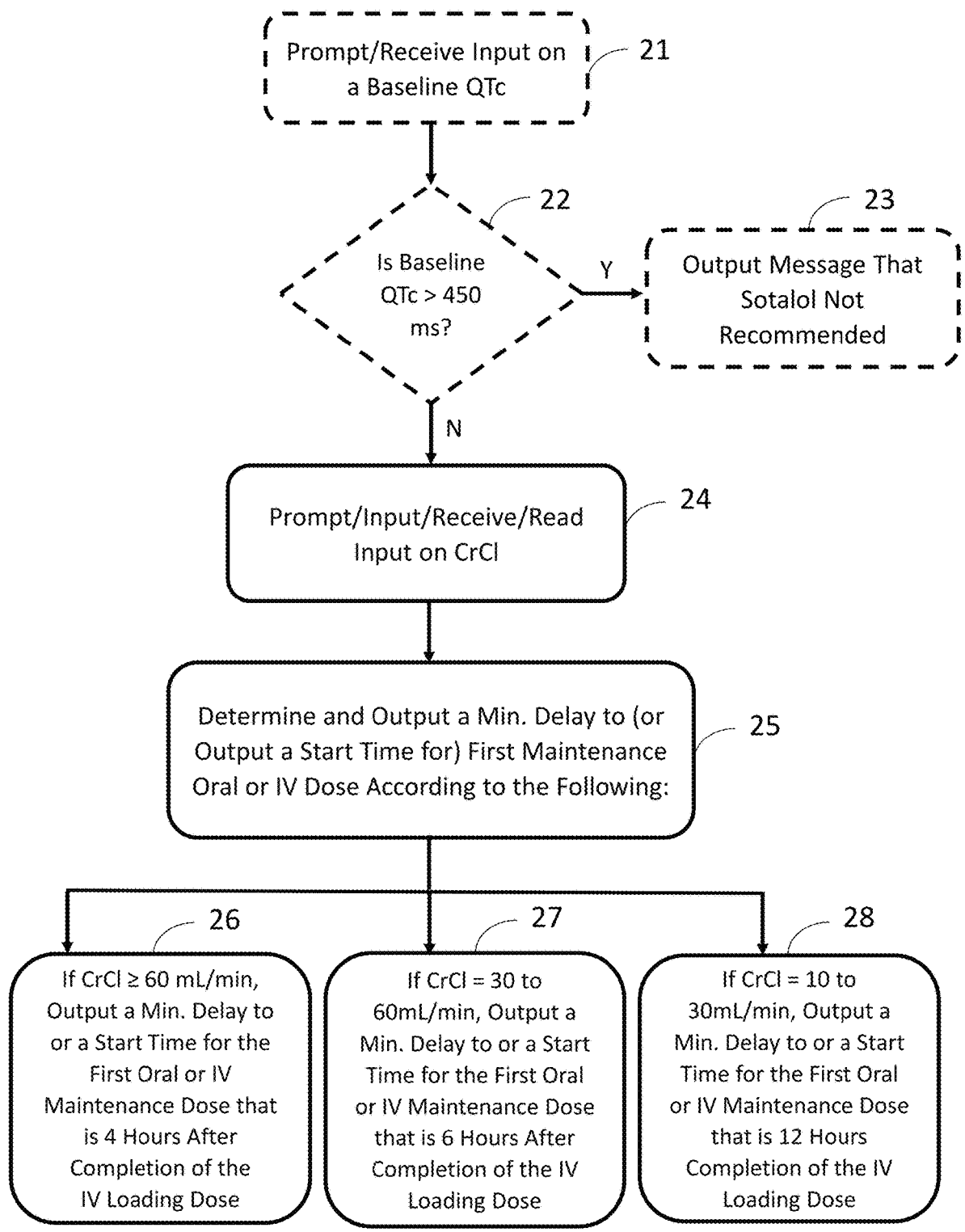
FIG. 7 is a flowchart of an exemplary method for determining when maintenance dosing for sotalol hydrochloride begins relative to an IV loading dose for sotalol hydrochloride based on renal clearance ability of a subject.

Another implementation of a method is shown in FIG. 7. The method can start with prompting/inputting/receiving/reading an input relating to the patient's kidney and/or liver clearance ability 24 (such as a creatinine clearance). Based on the input of the patient's creatinine clearance and/or liver clearance, the timing of and/or a minimum delay to first oral or IV maintenance dose is determined, and the timing of and/or minimum delay is outputted 25. For sotalol hydrochloride, for example, if the inputted creatinine clearance is 60 mL/min or more, then a minimum delay of 4 hours is outputted 26 (i.e., the practitioner is prompted and/or receives an output that the first oral dose should be administered at least 4 hours or more after completion of the IV, or a start time for the first maintenance dose can be outputted/provided). If the inputted creatinine clearance is within the range of 30 to 60 mL/min, then a minimum delay of 6 hours is outputted 27 (i.e., the first oral dose is instructed to be administered at least 6 hours after completion of the IV and/or a corresponding start time for maintenance dosing can be provided/outputted), or if more than one option applies, a choice of administration times and/or minimum delay to first oral dose can be provided. If the inputted creatinine clearance is within the range of 10 to 30 mL/min, then a minimum of 12 hours is outputted 28 (i.e., the timing of the first oral dose is determined/output as starting at least 12 hours after completion of the IV dose), or a choice of options can be provided. Creatinine clearance and/or liver clearance thresholds for other antiarrhythmics can be found in the labeling information provided in the product labels referenced herein and the corresponding thresholds for those drugs can be used instead if initiating, continuing or administering other antiarrhythmic drugs.

Figure 8:
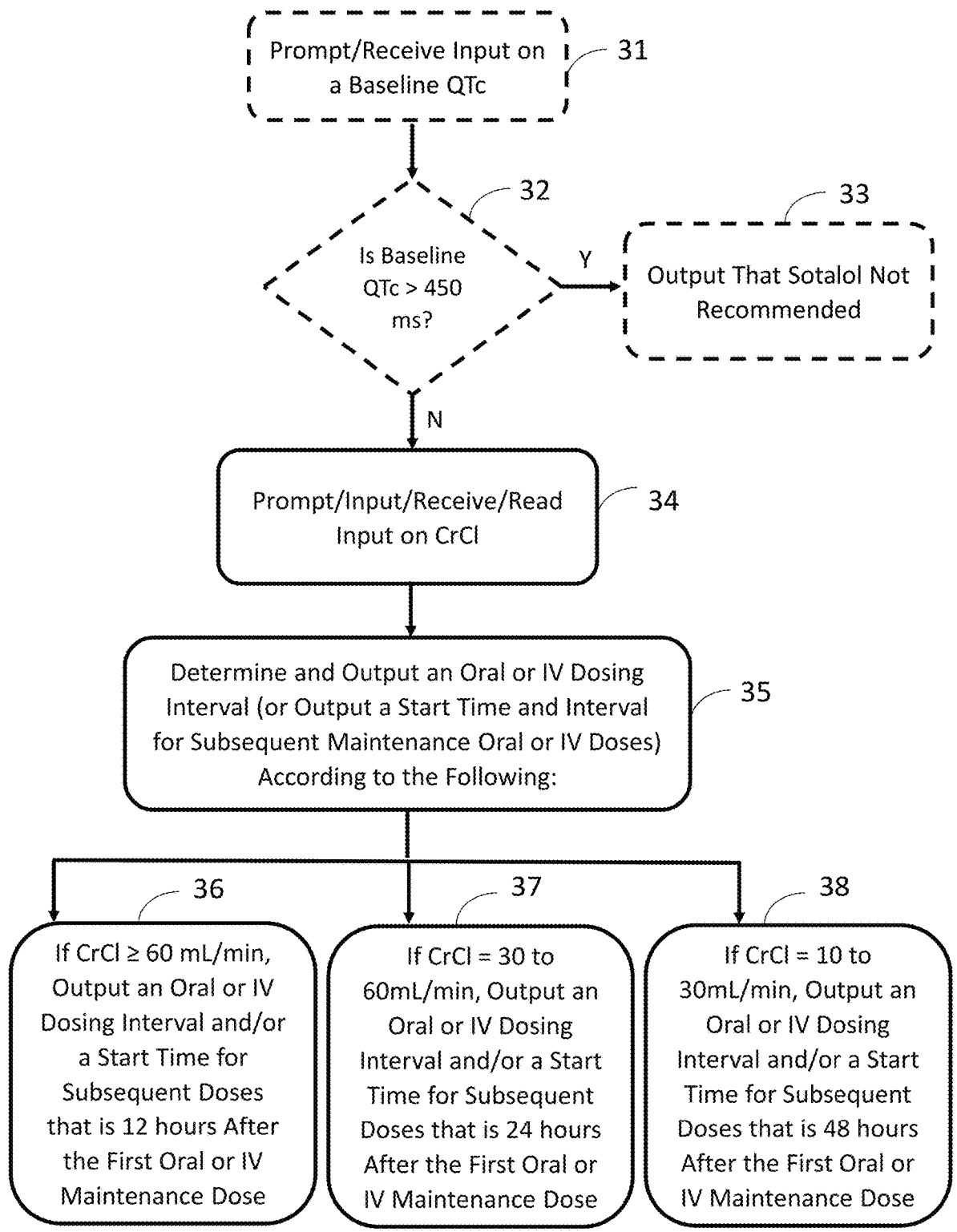
FIG. 8 is a flowchart of an exemplary method for determining a maintenance dosing interval for sotalol hydrochloride.

Another implementation of a method is shown in FIG. 8. The method can start with prompting or receiving input of a patient's creatinine clearance 34. For antiarrhythmic drugs where liver clearance is an issue, the health professional can instead or in addition be prompted to enter a value relating to the patient's liver clearance ability or the creatinine clearance can be presented by the user interface by way of a drop down list to be selected. Based on the input of the patient's creatinine clearance or liver clearance capability, an oral or IV dosing interval is determined, and the oral or IV dosing interval is outputted 35. For antiarrhythmic drugs that are administered intravenously, an IV dosing schedule/interval will be outputted (e.g., ibutilide or procainamide). If the inputted creatinine clearance is 60 mL/min or more, then for sotalol hydrochloride a dosing interval of 12 hours is outputted 36 (e.g., administration of subsequent oral and/or IV doses is indicated to be at 12 hour intervals from the first maintenance dose, such as from the first oral dose). For a creatinine clearance input of within the range of 30 to 60 mL/min, then a dosing interval for sotalol of 24 hours is outputted 37 (e.g., administration of subsequent oral and/or IV doses is indicated to be at 24 hour intervals from the first maintenance dose, such as from the first oral dose), or a choice of dosing intervals can be provided if more than one option applies. For a creatinine clearance input of within the range of 10 to 30 mL/min, then a dosing interval for sotalol of 48 hours is outputted 38 (e.g., administration of subsequent oral and/or IV doses is indicated to be at 48 hour intervals from the first maintenance dose, such as from the first oral dose), or a choice of interval options is presented. Maintenance dosing intervals, such as oral dosing intervals, and creatinine clearance or liver clearance thresholds for other antiarrhythmics are provided in the product labels referenced herein and can be substituted in place of those for sotalol if initiating, continuing or administering another antiarrhythmic drug.

Figure 9:
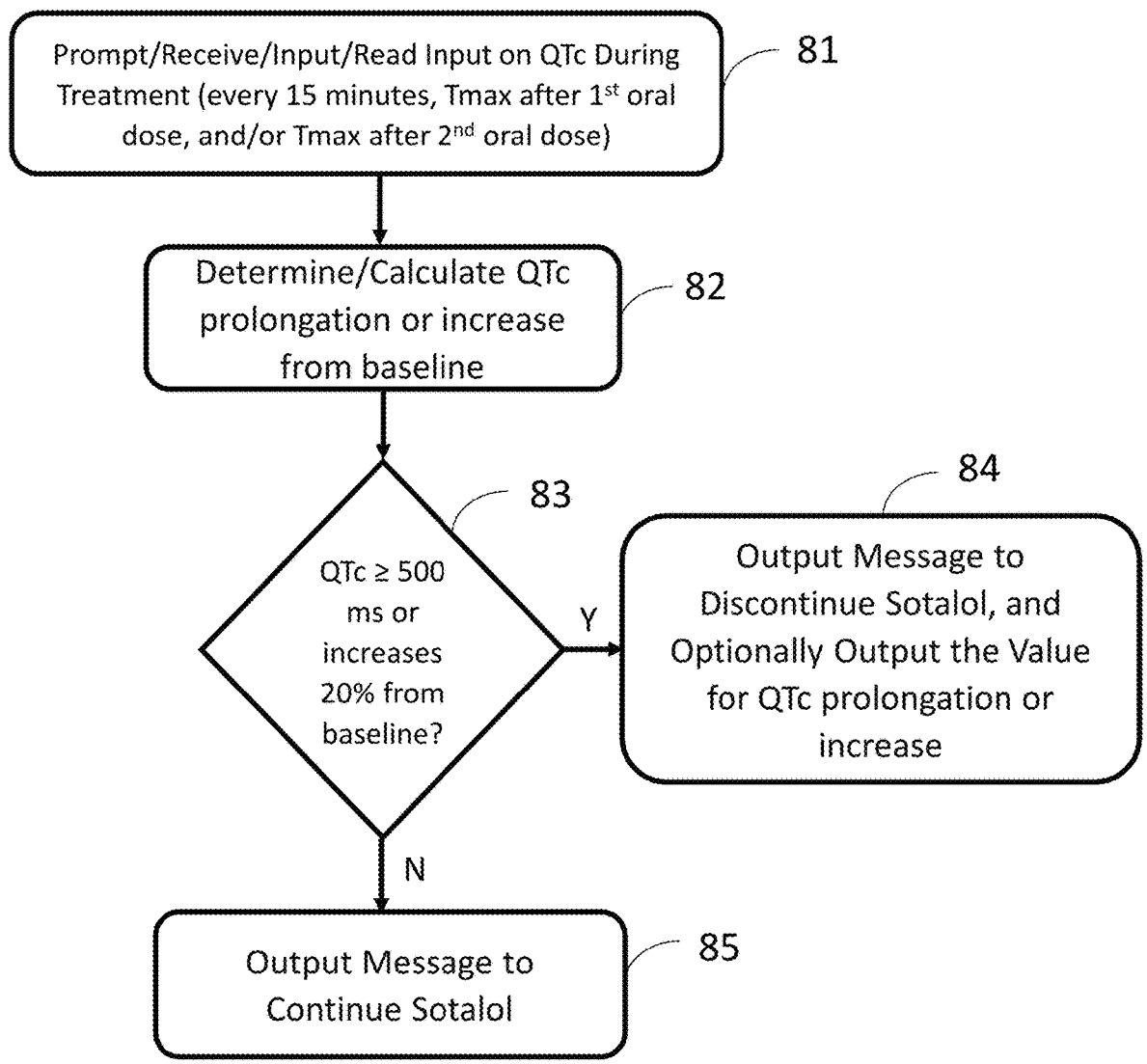
FIG. 9 is a flowchart depicting a method for monitoring QTc of a subject to determine whether to continue with dosing sotalol hydrochloride or lower the dose.

Another implementation of a method is shown in FIG. 9. The method can be implemented for patients having a current sotalol oral dose of 0 mg and a target sotalol oral dose of 80 mg (e.g., initiation), and such values can be inputted along with one or more health characteristics of the patient in steps described for other methods provided herein. Appropriate current and target oral and/or IV doses for other antiarrhythmic drugs can be found in the product labels referenced herein. For sotalol, as an example, a health professional is first prompted to input patient QTc during sotalol treatment 81. The QTc can be measured and then inputted at 15 minute intervals, at or around $T_{max}$ after a $1^{st}$ oral dose, and/or at or around $T_{max}$ after a $2^{nd}$ oral dose. Then, QTc prolongation or increase from baseline are determined or calculated based on the inputted QTc 82. Then, a determination is made as to whether QTc is equal to or exceeds 500 ms or increases 20% from baseline 83. If QTc is equal to or exceeds 500 ms or increases 20% from baseline, then a message to discontinue sotalol is outputted 84; the QTc value and/or percentage increase from baseline value may also be optionally outputted. If QTc does not equal or exceed 500 ms or increase 20% from baseline, then a message to continue sotalol is outputted 85. Corresponding threshold values for QTc prolongation or increase from baseline can be found in the product labels referenced herein for other antiarrhythmic drugs.

Figure 10:
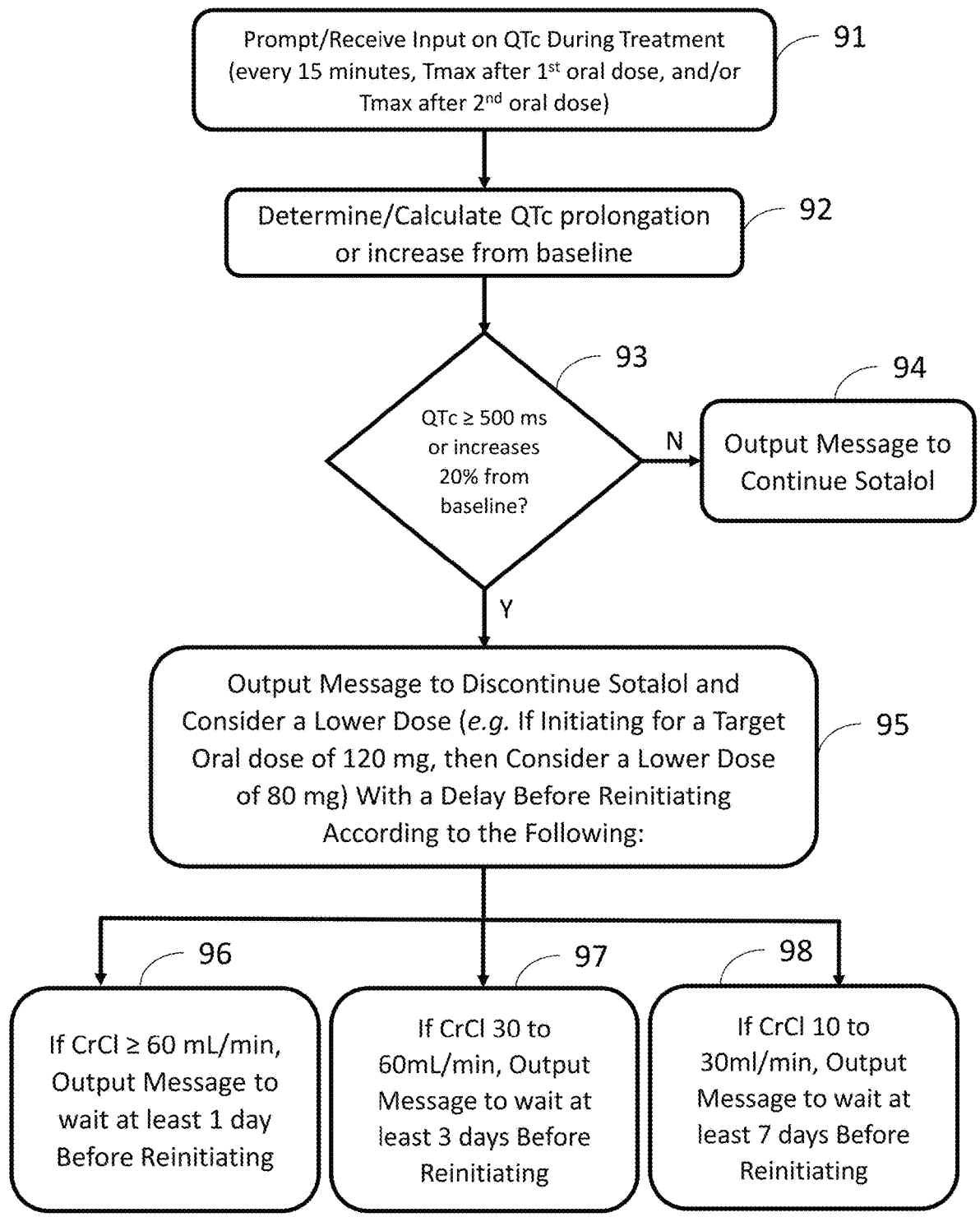
FIG. 10 is a flowchart depicting a method for monitoring QTc of a subject to determine whether to continue with dosing sotalol hydrochloride or lower the dose, based on a subject's CrCl.

Another implementation of a method is shown in FIG. 10. The method can be implemented for patients having a current sotalol oral dose of 0 mg and a target sotalol oral dose of 120 mg, and such values can be inputted along with one or more health characteristics of the patient in steps described for previous methods. A health professional is first prompted to input a QTc during sotalol treatment 91. The QTc can be measured and then inputted at 15-minute intervals, at or around $T_{max}$ after a first oral dose, and/or at or around $T_{max}$ after a second oral dose. Then, QTc prolongation or increase from baseline are determined or calculated based on the inputted QTc 92. Then, a determination is made as to whether QTc equals or exceeds 500 ms or increases 20% from baseline 93. If QTc does not equal or exceed 500 ms or increase 20% from baseline, then a message to continue sotalol is outputted 94. If QTc equals or exceeds 500 ms or increases 20% from baseline, then a message to discontinue sotalol and consider a lower dose (e.g. 80 mg) with a delay before reinitiating is outputted 95; the QTc value and/or percentage increase from baseline value may also be optionally outputted. If the patient's inputted creatinine clearance is greater than or equal to 60 mL/min, then a message is outputted to wait at least 1 day before reinitiating 96. If the patient's creatinine clearance is within the range of greater than or equal to 30 to less than 60 mL/min, then a message is outputted to wait at least 3 days before reinitiating 97. If the patient's creatinine clearance is within the range of ≥10 to <30 mL/min, then a message is outputted to wait at least 7 days before reinitiating 98.

In embodiments, a health care professional can input one or more health characteristics of a patient and one or more oral or IV dosing characteristics of the patient (relating to any one or more of sotalol, dofetilide, amiodarone, ibutilide, dronedarone, procainamide, flecainide, or propafenone). The one or more health characteristics of the patient can include information that can affect one or more pharmacokinetic characteristics or behaviors of sotalol etc. in the patient, such as renal or liver clearance, half-life, bioavailability, absorption, $C_{max}$, $T_{max}$, and Area under the Curve (AUC). Such health characteristics can include renal function, as indicated by patient creatinine clearance, or liver function, or concomitant medications. The one or more health characteristics can also include information indicating a potential risk of an adverse effect. The adverse effect can include proarrhythmia (e.g. Torsade de Pointes (TdP)), bradycardia, sinus pauses or sinus arrest, hypotension, heart failure, negative inotropy, dyspnea, and/or fatigue, or any other adverse effect available from sotalol pre-marketing or post-marketing studies or reports. Adverse effects for various antiarrhythmics such as sotalol, dofetilide, amiodarone, ibutilide, dronedarone, procainamide, flecainide, or propafenone, can be found in the product labels referenced herein. The information indicating a potential risk can include patient QT interval or QTc or concomitant medications, or any other information relevant to the appropriateness of initiation, escalation or continuation of the antiarrhythmic to be administered. The one or more oral or IV dosing characteristics can include information such as current oral or IV dose of the drug and target oral or IV dose of the drug, such as whether the patient/subject is being initiated on the drug or escalated to a higher oral dose of the drug or switched to another drug. The dosing characteristics can include drug information for an antiarrhythmic drug a patient is currently taking (such as dofetilide) and drug information for a target drug the patient is expected to be switched to (such as sotalol), or vice versa. Then, a determination is made regarding appropriateness of the antiarrhythmic drug for the patient, IV loading dose, or IV or oral dosing protocol characteristics such as minimum delay to first oral or IV maintenance dose, and/or oral or IV dosing interval, based on the input(s). Then, a message is outputted regarding appropriateness of the drug for the patient, IV loading dose, minimum delay to first oral or IV dose, and/or oral or IV maintenance dosing interval, based on the determination(s) made.

In any embodiment, for example those disclosed in FIGS. 1-10, additional steps can optionally include steps relating to a subject's fitness for a particular antiarrhythmic drug based on QTc measurements. Optionally, a baseline QTc of a patient can be input or prompted to be input, read or received for determining antiarrhythmic drug dosing. For sotalol hydrochloride, a determination can be made as to whether the baseline QTc exceeds a threshold of 450 ms. Other antiarrhythmic drugs may have a different threshold for QTc and can be found in the product labels referenced herein. If the baseline QTc exceeds a threshold of 450 ms, sotalol (or other antiarrhythmic) is not recommended and a corresponding alarm, alert or message can be outputted. If the baseline QTc does not exceed the threshold of 450 ms, additional steps as outlined in any of FIGS. 1-10 can be taken to determine the appropriate dosing for the subject. Exemplary steps relating to measuring QTc are shown by way of the dotted-line portions of FIG. 6 (see 11, 12, 13), FIG. 7 (see 21, 22, 23) and FIG. 8 (see 31, 32, 33). When referring to QTc or a QT interval, either can be used in the embodiments or figures herein and either can be input into the medical device, systems or apps herein and substituted accordingly.

Figure 11:
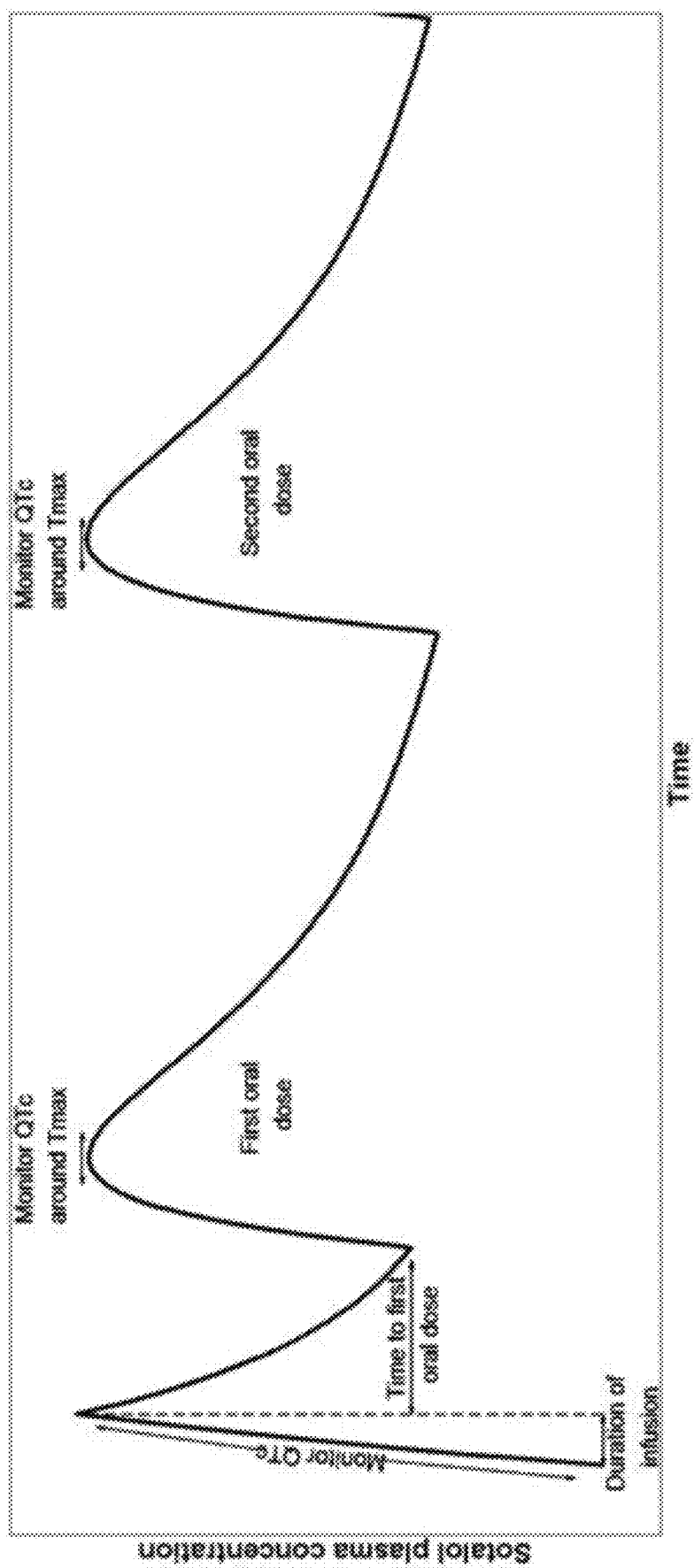
FIG. 11 is an illustration of a pharmacokinetic profile for an intravenous sotalol loading dose followed by subsequent sotalol oral doses in a typical patient.

FIG. 11 illustrates implementation of various features of the method implementations in the context of a pharmacokinetic profile of a typical patient. In particular, FIG. 11 illustrates patient QTc monitoring occurs at stages within the pharmacokinetic profile in which the patient is most vulnerable to concentration-dependent adverse effects (e.g. ventricular arrhythmias).

Steps involving measurement of a QTc baseline of a patient or QTc at specified intervals, or measurement of QTc at specific times, are subject to implementation or modification by a qualified physician according to their professional judgment. For example, the QTc baseline can be measured within hours (e.g. 12, 8, 6, 5, 4, 3, 2, 1) or minutes (e.g. 45, 30, 20, 15, 10, 5) prior to initiating a procedure prompted by the method implementations, such as administering a loading dose. The QTc baseline measurements can be taken at multiple times and averaged, or be taken at a single time. Specific intervals for measuring QTc during infusion of the loading dose can include 5, 10, 15, or 20 minutes. Measuring QTc around $T_{max}$ after a first and/or second oral dose can include measuring QTc at 2 to 4 hours, 1 to 3 hours, or 2.5 to 5 hours after the first and/or second oral dose, and/or adjusting the time of QTc measurement according to the patient's creatinine clearance or other variable potentially affecting sotalol $T_{max}$ values, such as concomitant medications, and/or adjusting the time of QTc measurement according to sotalol pharmacokinetic data obtained from a clinical population of patients.

Steps involving "prompting", "inputting", "calculating", "determining", and "outputting" depicted in the preceding figures can be implemented in a variety of ways known in the computer science and engineering arts.

Prompting and inputting steps can be performed through one or more input-output (I/O) interface on the computer or computing device. Inputting can be provided manually from a user and/or provided automatically from any one or more devices or systems for obtaining patient information, such as creatinine clearance, QT interval or QTc. Prompting steps can be performed as visual or auditory cues for the health professional to enter specific patient characteristics. Visual prompting can take the form of a message and/or input field provided to the health professional on a display. The input field can be provided as part of a graphical user interface provided on the display of the computing device which provides one or more data entry fields, check boxes, or pull-downs which allow the health professional to input data. Auditory prompting can take the form of speech or a recording broadcast from a speaker which prompts the health professional to enter the patient characteristics. Inputting steps can be performed through traditional inputting means such as a physical keyboard or a keyboard projected on a display, such as a touchscreen. The keyboard can be a QWERTY keyboard or a condensed keyboard commonly used in electronic devices such as cell phones. Inputting can also be performed through the health professional providing speech which is inputted through a microphone of the computer or computing device and recognized by speech recognition algorithms programmed on the computer or computing device. Inputting can also be performed automatically through another medical device or system that is in operable connection/communication with the inventive device or system, such as an EKG, a database with stored patient data and/or one or more medical monitoring or measuring devices or systems, such as for obtaining a patient creatinine clearance rate.

Calculating and determining steps can be performed by way of a processor coupled with a memory which has patient health characteristic data and sotalol dosing data stored within or accessible to it. Calculating steps can be performed through mathematical operations programmed on the computer or computing device such as multiplication, addition, subtraction, division, logarithmic functions, exponential functions, algorithmic functions, and so on. Determining steps can be performed by retrieving antiarrhythmic drug dosing data stored in a database within the memory of the computer or computing device based on patient characteristics inputted by the health professional or medical monitoring/measuring device(s). For example, the database can store sotalol (or other antiarrhythmic drug) dosing data, such as sotalol/antiarrhythmic IV loading dose, time for administration of or minimum delay (if any) to first oral or IV maintenance dose, and/or oral or IV maintenance dosing interval as arranged in Table 1 (sotalol) below, such as they are stratified according to tiers of creatinine clearance ranges, and/or or sotalol initiation or escalation values. Specific dosing for other antiarrhythmic drugs can be found in the product labels referenced herein and used instead if administering another antiarrhythmic drug. The determining steps can be performed by retrieving sotalol/antiarrhythmic IV loading dose, administration time of or minimum delay (if any) to first oral or IV dose, and/or oral or IV dosing interval stored in the database within the memory of the computer or computing device based on one or more of the patient health characteristics or sotalol/antiarrhythmic dosing characteristics inputted by the health professional or other monitoring/measuring equipment. The retrieving can include matching one or more inputted patient health characteristics or sotalol/antiarrhythmic dosing characteristics with the values or ranges used to stratify sotalol/antiarrhythmic IV loading dose, administration time of or minimum delay (if any) to first oral or IV dose, and/or oral or IV dosing interval values, so that the appropriate sotalol dosing data is retrieved, provided, accepted and/or inputted.

TABLE 1

| | Recommended Loading Dose | | | | | |
|---|---|---|---|---|---|---|
| | Intravenous loading dose [mg] to be administered over 1 hour when the oral dose is going from... | | | | Minimum delay | Oral dosing |
| Creatinine Clearance* [mL/min] | Setalol Initiation | | Setalol Escalation | | to first oral dose [hours] | interval [hours] |
| | 0 to 80 mg** | 0 to 120 mg | 80 to 120 mg | 120 to 168 mg | | |
| >90 | 60 | 90 | 75 | 90 | 4 | 12 |
| 60-90 | 82.5 | 125 | 82.5 | 105 | 4 | 12 |
| 30-60 | 75 | 112.5 | 82.5 | 105 | 6 | 24 |
| 10-30 | 75 | 112.5 | 82.5 | 105 | 12 | 48 |

*Calculated using Cockcroft Gault formula
**Recommended starting dose

The sotalol/antiarrhythmic dosing data (e.g. intravenous loading doses, minimum delay to first oral dose, and oral dosing interval) in Table 1 (e.g., sotalol) can be determined from computer-based simulations incorporating sotalol dose-exposure-QTc relationships, and can be modified according to additional computer-based simulations. The computer-based simulations can be based upon mathematical functions, equations, or algorithms which represent the sotalol dose-exposure-QTc relationships, which can be based on theoretical considerations and/or determined empirically.

Outputting steps can be formed through a visual output device such as a display on the computer or computing device, an auditory output device such as a speaker, and/or through other output such as one or more lights (e.g. LEDs). The output can be in the form of text, images and/or video providing instructions on the display to the health professional, and/or through audio messages broadcast on the computer or computing device's audio output device providing such instructions.

The computer-executable code or instructions can be implemented as software or an application capable of being run on a computer or computing device such as a desktop computer or a portable computer/computing device, such as a tablet, laptop, PDA, or smartphone. The computer-executable code or instructions can be installed on the computer or computing device during manufacture as software, or implemented as firmware or hardware (e.g. circuitry), or some combination of these. The computer-executable code or instructions can be configured to be downloadable onto the memory of the computer or computing device from a cloud storage source available on the internet, such as an application retail source (e.g. "app store") capable of being accessed from a mobile phone, tablet, desktop computer, or other programmable device having components or features capable of performing the method steps described above. Examples of suitable internet-accessible sources include the Apple Store, Google Play, and other sites that make software applications and other downloads available for purchase or license.

The computer-readable code, computer-readable instructions, computer-executable instructions, or "software" can be organized into routines, subroutines, procedures, objects, methods, functions, or any other organization of computer-executable instructions that is known or becomes known to a skilled artisan in light of this disclosure, and can be programmed in any suitable programming language, including JavaScript, C, C#, C++, Java, Python, Perl, Ruby, Swift, Visual Basic, and Objective C. By such programming, the computer-readable code, computer-readable instructions, computer-executable instructions, or "software" instruct a processor of the computer or computing device to carry out the operations and commands of the application. Inputted patient health characteristic data, sotalol dosing data, and computer-executable instructions can be stored in the computer or computing device's memory. The memory can be implemented through non-transitory computer-readable storage media such as RAM. As used in the context of this specification, a "non-transitory computer-readable storage medium (or media)" may include any kind of computer memory, including magnetic storage media, optical storage media, nonvolatile memory storage media, and volatile memory. Non-limiting examples of non-transitory computer-readable storage media include floppy disks, magnetic tape, conventional hard disks, CD-ROM, DVD-ROM, BLU-RAY, Flash ROM, memory cards, optical drives, solid state drives, flash drives, erasable programmable read only memory (EPROM), electrically erasable programmable read-only memory (EEPROM), non-volatile ROM, and RAM.

Additional implementations include a computer, computing device, medical device, or system capable of carrying out the method implementations. The computer, computing device, medical device, or system can include one or more processors capable of executing the computer-readable code, computer-readable instructions, computer-executable instructions, or "software", one or more interface capable of providing input or output, one or more databases and a set of instructions (e.g. software) stored in a memory of the computer, computing device, medical device, or system for carrying out the method implementations. The computer, computing device, medical device or system can include a stand-alone computer, such as a desktop computer, a portable computer, such as a tablet, laptop, PDA, watch, or smartphone, or a set of computers or devices connected through a network including a client-server configuration and one or more database servers. The network can use any suitable network protocol, including IP, UDP, or ICMP, and may be any suitable wired or wireless network including any local area network, wide area network, Internet network, telecommunications network, Wi-Fi enabled network, or Bluetooth enabled network. In this way, one or more steps of the method implementations can be distributed across the system, or performed directly on a smartphone, computer, computing device, or medical device, according to specific applications or designs.

In another implementation, the system includes 1) one or more computer that is located off-site from a health care environment and 2) one or more computing device located within a health care environment. The off-site computer can be a fixed position computer, and the computing device within the health care environment can be of the desktop variety, or mobile, portable, handheld or worn by a user. The off-site computer can be connected to the internet and can have an internal database capable of housing data, such as patient health characteristic data inputted from the mobile or portable computing device as well as sotalol dosing data, which database is stored in the memory of the off-site computer. The database can be a standard relational database that communicates by way of a database server with the mobile computing device. The off-site computer can include a set of computer-executable instructions stored in memory which can be used to perform the calculating and determining steps off-site. The off-site computer can then communicate to the portable computing device or smartphone the results of such calculating and determining steps as well as messages to be outputted on the portable computing device.

Embodiments include a medical device, such as an electronic device (e.g., handheld electronic device), and/or a medical device comprising software with a graphical user interface and/or software that is accessed through hardware that provides for user interface through screen display(s). In embodiments, the medical device is a software based calculator that uses an algorithm to determine/calculate a loading dose of an antiarrhythmic drug (such as from a table), such as sotalol hydrochloride IV (e.g., using Table 1), using inputted/retrieved data, for example inputted data relating to a creatinine clearance of a subject (which can be inputted manually by a user and/or inputted automatically from another medical device/system), and current and/or target use of the drug for the subject (such as a whether the subject is being initiated on or escalated to a higher oral dose of the drug) and/or the target oral maintenance amount of the drug. In embodiments, the medical device is a quick response code (QR code) contained in a product label, such as labeling for sotalol hydrochloride IV (or any of the product labels referenced herein), which QR code provides digital access (e.g., by scanning the QR code with a mobile device/phone) to a dosing calculator for healthcare professionals, which is intended to recommend dosing parameters for administering IV and/or oral sotalol hydrochloride to a patient. Such medical devices can comprise software stored on an electronic device configured to (i) read, prompt input of and/or accept as inputs: a projected start time for sotalol hydrochloride infusion; creatinine clearance (CrCl) of a subject; whether the subject is being initiated on or escalated to a higher oral dose of the sotalol hydrochloride; and an amount of an oral target dosage of sotalol hydrochloride for the subject; and (ii) execute computer executable instructions to derive from a set of rules (e.g., rules based on criteria set forth in Table 1) a sotalol hydrochloride dosing protocol for the subject based on one or more of the inputs, the dosing protocol comprising: at least an amount of the sotalol hydrochloride for infusion as a loading dose; and optionally a time for a first oral dose of sotalol hydrochloride and/or a time for a second oral dose of sotalol hydrochloride, or oral dosing interval; and (iii) output the sotalol hydrochloride dosing protocol, for example to a healthcare professional.

Figure 12:
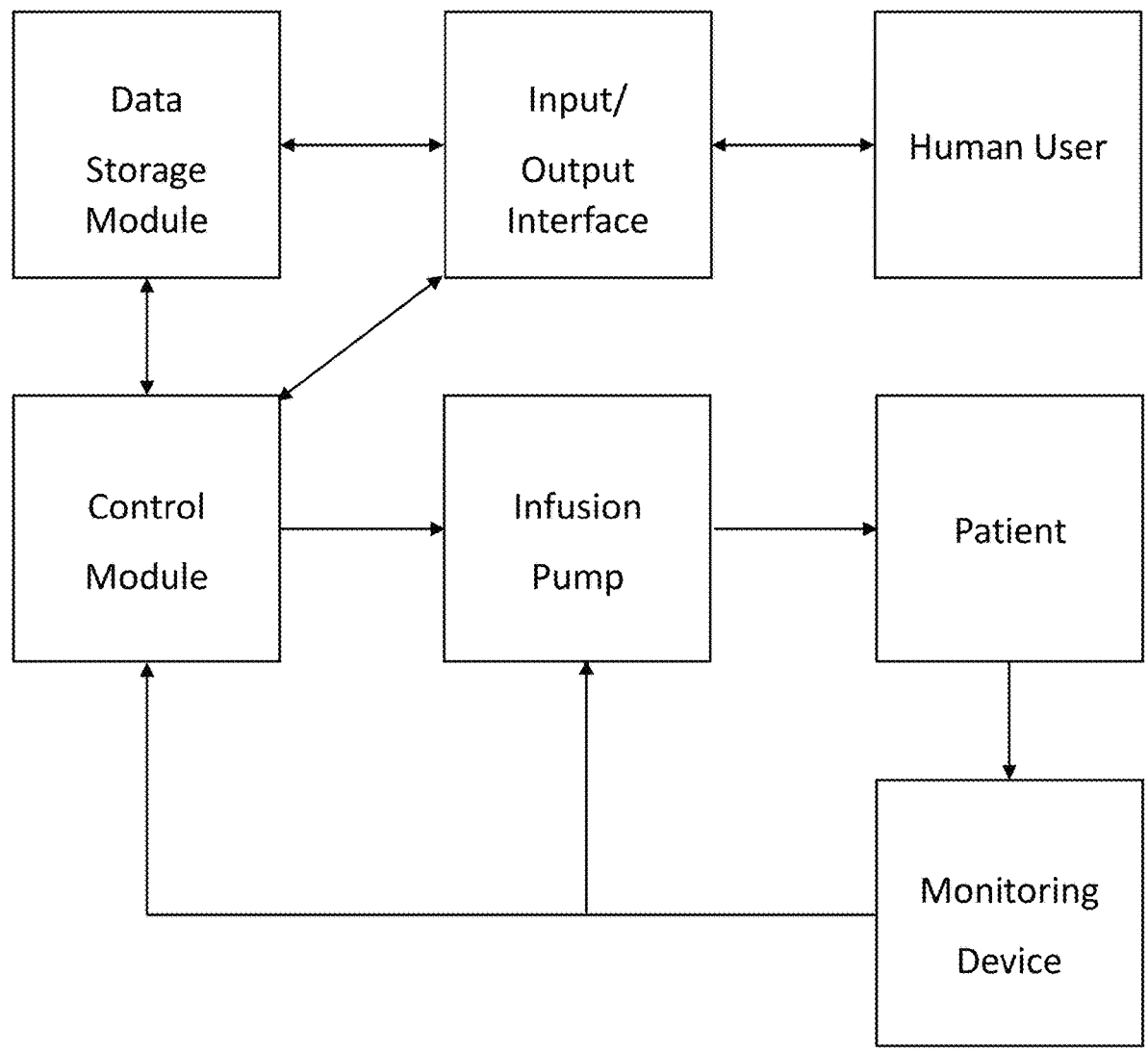
FIG. 12 is an exemplary system and medical device for determining dosing and optionally administering one or more antiarrhythmic drug, such as sotalol, dofetilide, amiodarone, ibutilide, dronedarone, procainamide, flecainide, and/or propafenone to a subject.

An exemplary system is provided in FIG. 12, which illustrates a medical device and system for determining dosing and optionally administering one or more antiarrhythmic drug, such as sotalol (e.g., sotalol hydrochloride IV), dofetilide, amiodarone, ibutilide, dronedarone, procainamide, flecainide, and/or propafenone to a subject. In embodiments, the system can comprise a dosing calculator comprising a standalone medical device, such as a handheld electronic device, comprising i) an input/output graphical user interface; ii) a memory configured to store dosing criteria for sotalol hydrochloride (e.g., Table 1), store data relating to a subject's current and/or target antiarrhythmic drug dosing amounts, such as sotalol hydrochloride dosing amounts, and store computer-executable instructions for analyzing the subject's dosing related data according to the dosing criteria; iii) a computer processor operatively connected to the memory configured to analyze the data relating to the patient and to identify one or more acceptable IV dose of an antiarrhythmic drug, such as sotalol hydrochloride. Such dosing and administering can be employed for treating one or more cardiovascular condition of a patient, such as atrial fibrillation, atrial flutter, ventricular tachycardia, hemodynamically stable or unstable ventricular tachycardia, ventricular fibrillation, paroxysmal supraventricular tachycardia, paroxysmal atrial fibrillation, heart failure, coronary artery disease, or pulmonary artery hypertension; maintenance of normal sinus rhythm (delay in time to recurrence of atrial fibrillation or atrial flutter (AFIB/AFL)) for example in patients with symptomatic AFIB/AFL and/or who are currently in sinus rhythm, and/or indicated for the treatment of life-threatening ventricular tachycardia; and/or treating people, such as hospitalized people, with atrial fibrillation cardioverted to normal sinus rhythm, without ventricular arrhythmias or various forms of blocks, in patients with normal kidney function; treating life-threatening recurrent VF or life-threatening recurrent hemodynamically unstable VT; treating paroxysmal or persistent atrial fibrillation or atrial flutter, such as with patients who have experienced a recent AFIB/AFL episode who are in sinus rhythm or who will be cardioverted; and/or treating Wolff-Parkinson-White syndrome and/or paroxysmal supraventricular tachycardia. In embodiments, the dosing protocol, such as the IV dose of sotalol hydrochloride, can be input into a control module from the dosing calculator, optionally operably connected with the medical device dosing calculator, for controlling an infusion pump, also optionally operably connected with the control module, according to the dosing protocol to administer the IV sotalol to a patient. Feedback can be provided by a monitoring device, such as an EKG, and input into the control module for adjusting the administering at any point depending on how the subject is responding to the IV treatment, such as IV sotalol treatment.

In implementations, one or more steps of the method implementations can be performed on another medical device, such as an EKG or other medical measuring device. The EKG measuring device can be a 12-lead EKG, or a Holter monitor. The EKG measuring device can include any computer component necessary for performing one or more steps of the method implementations, including one or more processor, a memory, and any component capable of providing input or output. The EKG measuring device can include any computer-readable code, computer-readable instructions, computer-executable instructions, or "software" for performing one or more steps of the method implementations described or depicted herein. In some implementations, the EKG measuring device bypasses the prompting/receiving QTc input steps of the method implementations, such as steps 11, 21, 31, 41, 51, 61, 71, 81, 91, so that these steps are not performed, and instead provides the QTc values or determinations directly for subsequent steps, such as determining whether QTc exceeds a threshold (e.g. 450 ms), such as steps 12, 22, etc. and/or increases from baseline QTc over a percentage threshold, such as steps 83 and 93. The determinations performed on the EKG measuring device can include operations such as comparison to a stored QTc value, multiplication, addition, subtraction, division, logarithmic functions, exponential functions, algorithmic functions, and so on. In some implementations, one or more additional steps of the method implementations are performed on the EKG measuring device, such as those involving outputting a message to continue or discontinue sotalol (e.g. steps 84, 84, 94, 95), or a message to recommend or not recommend sotalol (e.g. steps 13, 23, 33, and so on). The EKG device can also be equipped with a wired (e.g. USB) or wireless (e.g. WiFi, BLUETOOTH®) connection capable of communicating information or data (e.g. QTc values or determinations) with a computer or computing device that is equipped to perform subsequent steps of the method implementation based on the communicated information or data. In some implementations, all of the steps of one or more of the method implementations depicted in FIGS. 1-10 are performed on the EKG measuring device.

Computers, computing devices, or medical devices described herein can include a variety of components known in the art, including one or more processor, a volatile memory, a non-volatile memory, standard I/O interfaces such as a universal serial bus (USB) port, an HDMI or HDMI ARC port, an optical port, an ethernet port, and/or a serial port, a hard drive, a disk drive, a CD-ROM drive, a motherboard, a printed circuit board (PCB), circuitry for enabling a wireless connection or communication to another device, such as a BLUETOOTH® board, a WiFi board, or a transmitter-receiver for mobile telecommunications, a data bus, an address bus, a control bus, and/or one or more user interface devices including a display, keyboard, keypad, trackpad, mouse, control panel, touch screen display, speaker, camera, and/or microphone. The computers, computing devices, or medical devices can be equipped with an operating system implemented as software or firmware. As can be appreciated, the computers, computing devices, or medical devices may differ in their inclusion, exclusion, or configuration of components according to their individual applications or designs.

The sotalol/antiarrhythmic dosing methods, devices, and systems described herein can be used as follows. A patient presents to a health care facility with a condition suitable for treatment with sotalol, such as symptomatic AFIB/AFL. A health care professional, such as a physician, determines that the patient may be a candidate for sotalol/antiarrhythmic treatment based on a clinical evaluation of the patient's symptoms, consideration of possible contraindications, and other patient health information. The health care professional uses a computing device, such as a smartphone or tablet, loaded with a software application capable of performing one or more of the methods described herein, to determine sotalol/antiarrhythmic suitability, to determine suitable choices of antiarrhythmic for the particular patient, and/or to determine an appropriate IV loading dose, and/or determine an appropriate oral or IV dosing protocol, by following the prompting of the application and entering appropriate information. In embodiments, some or all of the health characteristics or patient measurements (such as vitals) can be entered automatically from other medical devices monitoring or assessing the patient. The output of the application informs the health care professional of such suitability, appropriate IV loading dose, and/or appropriate oral or IV maintenance dosing protocol.

Implementations and features of the sotalol/antiarrhythmic dosing methods, devices, and systems are provided below, as well as guidelines and procedures informing their use or application. All values provided in Table 1 and FIGS. 1-10 are subject to modification according to the following.

AFIB is atrial fibrillation.
AFL is atrial flutter.
AFIB/AFL=atrial fibrillation and/or atrial flutter.
IV is intravenous.
PO means "per os" and refers to an oral dosing regimen.
BID means "bis in die" and means twice a day.
QD means "quaque die" and means once a day.
QID means "quater in die" and means four times a day.
Patient (or subject) refers to a human patient.
BP is blood pressure.
HR is heart rate.
Renally impaired refers to patients having creatine clearance rates of <60 mL/min.
Sotalol and sotalol hydrochloride (used interchangeably herein) refer to d,l-sotalol hydrochloride which has been approved by the FDA for intravenous administration over 5 hours or oral administration (e.g., 80 mg, 120 mg, and 160 mg tablets).
In an example, sotalol injection is supplied in 10 mL single-dose vials, each containing 150 mg of sotalol hydrochloride as a clear solution (15 mg/mL).

Sotalol hydrochloride is contraindicated in patients with:
Sinus bradycardia (<50 bpm), sick sinus syndrome or second or third degree AV block without a pacemaker
Congenital or acquired long QT syndromes, QT interval >450 ms
Cardiogenic shock, decompensated heart failure
Serum potassium <4 mEq/L
Bronchial asthma or related bronchospastic conditions
Known hypersensitivity to sotalol
Sotalol Indications:
Delay in Recurrence of Atrial Fibrillation or Atrial Flutter:
Sotalol is indicated for the maintenance of normal sinus rhythm (delay in time to recurrence of atrial fibrillation or atrial flutter (AFIB/AFL)) in patients with symptomatic AFIB/AFL who are currently in sinus rhythm.
Life-Threatening Ventricular Arrhythmia:
Sotalol is also indicated for the treatment of life-threatening ventricular tachycardia.
For either indication, intravenous sotalol, when used as a loading dose, achieves steady state concentration faster compared to the conventional oral dosing (e.g., typically 3-days for a non-renally impaired patient).

Typically, IV sotalol is diluted for infusion. For example, IV sotalol can be diluted in saline, 5% dextrose in water (D5W), or Ringer's lactate. The dilution volume chosen is one that is convenient for administration and consistent with fluid restriction. A volumetric infusion pump can be used to administer the IV sotalol.

Typically, other antiarrhythmic therapy is withdrawn prior to starting sotalol, but in some cases may be administered simultaneously with sotalol, or combinations of other antiarrhythmics can also be contemplated. In some cases, switching from one antiarrhythmic drug to another may also be contemplated, for example, switching a patient from dronedarone therapy to amiodarone therapy or vice versa, or from ibutilide to sotalol or vice versa.

In embodiments, a system for controlling administration of one or more antiarrhythmic drug to a patient is provided comprising:

i) an input/output interface configured to accept and display patient data obtained from user input and/or one or more monitoring device configured to monitor one or more physiological measurement of a patient, such as creatinine clearance, QT interval or QTc;

ii) a data storage module configured to store the patient data, the one or more physiological measurement of the patient and one or more dosing criteria for administering one or more antiarrhythmic drug to the patient; and iii) one or more control module comprising one or more processor for executing computer-readable instructions for:

a) determining an intravenous dose of the antiarrhythmic drug based on one or more of the patient data, one or more of the physiological measurement of the patient, and the dosing criteria; and b) providing instructions for controlling and/or controlling an infusion pump to administer the intravenous dose to the patient.

In embodiments, the dosing criteria for the software applications and systems described herein can be provided from labeling instructions for any antiarrhythmic drug, including but not limited to those provided in the product labels referenced herein for sotalol, dofetilide, amiodarone, ibutilide, dronedarone, procainamide, flecainide, or propafenone.

Dosing Criteria

In embodiments, the IV loading dose for the dosing criteria depends on the target oral or IV dose and creatinine clearance of the patient indicated for oral sotalol. The dosing interval for oral or IV administration of sotalol and/or the administration time or the minimum delay (if any) between the end of the loading infusion and the first oral or IV dose also depend on renal function. For other antiarrhythmics creatinine clearance and/or liver clearance may need to be accounted for when determining the IV loading dose. Although specific examples are provided herein relating to sotalol, depending on the particular antiarrhythmic selected (including additionally dofetilide, amiodarone, ibutilide, dronedarone, procainamide, flecainide, or propafenone, or any antiarrhythmic drug), the dosing can be adjusted up or down to be commensurate with the pharmacokinetics of the drug being administered and reference can be made to the product labels referenced herein for criteria for other specific antiarrhythmic drugs.

Thus, in an example, one implementation provides a software application for performing a method of initiating or escalating sotalol therapy, comprising: administering to a patient in need thereof (a patient for whom sotalol is indicated) an IV and oral sotalol dosage (or other antiarrhythmic drug) based on the patient's creatine clearance (CrCl mL/min), such as wherein the dosages and timing are selected from Table 1.

The Cockcroft-Gault formulas for creatine clearance (CrCl) are:

CrCl (male)=((140−age)×weight in kg)/(serum creatinine×72)

CrCl (female)=CrCl (male)×0.85

Recommended starting dose (80 mg) is the FDA recommended dosage. A physician can select to start a patient on a higher dosage (e.g., 120 mg), if deemed appropriate.

Minimum delay to first oral or IV dose is the time from the end of the loading IV infusion to the first oral or IV dose, which can be referred to as an oral or IV maintenance dose.

Oral or IV dosing interval refers to the time between oral or IV dosages. 12 h is B.I.D. (or BID). 24 h is Q.D. (or QD). 48 hr is according to a 2-day or every other day interval. Appropriate oral or IV dosing intervals for other antiarrhythmics can be found in the product labels referenced herein and can be substituted accordingly.

The IV loading dose for the dosing criteria, as shown in Table 1 (e.g., sotalol), is typically administered (infused) over 1 hour. Additional examples include 50-70 minutes. Further examples include 50, 51, 52, 53, 54, 55, 56, 57, 58, 59, 60, 61, 62, 63, 64, 65, 66, 67, 68, 69, and 70 minutes. For other antiarrhythmic drugs (e.g., dofetilide, amiodarone, ibutilide, dronedarone, procainamide, flecainide, or propafenone, or any antiarrhythmic drug), the duration of the IV administration can be adjusted up or down to be commensurate with the pharmacokinetics of the particular drug being administered. For example, infusion rates for the loading dose for other antiarrhythmics can be found in the product labels referenced herein.

Table 1 shows that the IV loading dose for initiation of a target dose of 80 mg are 60 mg (>90 mL/min CrCl), 82.5 mg (60-90 mL/min CrCl), and 75 mg (30-60 mL/min CrCl and 10-30 mL/min CrCl). Additional examples of the IV loading dose for a target oral dose of 80 mg include in the range of 55-85 mg. Further examples include 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, and 85 mg.

Table 1 shows that the IV loading dose for initiation of a target dose of 120 mg are 90 mg (>90 mL/min CrCl), 125 mg (60-90 mL/min CrCl), and 112.5 mg (30-60 mL/min CrCl and 10-30 mL/min CrCl). Other examples of the IV loading dose for a target dose of 120 mg include 75-135 mg. Further examples include 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, and 135 mg.

Table 1 shows that the IV loading dose for escalation from 80 mg to 120 mg are 75 mg (for >90 mL/min CrCl), and 82.5 (for 60-90 mL/min CrCl, 30-60 mL/min CrCl, and 10-30 mL/min CrCl). Additional examples of the IV loading dose for escalation to 120 mg include 65-90 mg. Further examples include 65, 66, 67, 68, 69, 70, 71, 72, 73, 74, 75, 76, 77, 78, 79, 80, 81, 82, 83, 84, 85, 86, 87, 88, 89, and 90 mg.

Table 1 shows that the IV loading dose for escalation from 120 to 160 mg are 90 mg (>90 CrCl), and 105 (60-90 CrCl, 30-60 CrCl, and 10-30 CrCl). Additional examples of the IV loading dose for escalation to 160 mg include 80-120 mg. Further examples include 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, and 120 mg.

As can be seen in Table 1 (for sotalol), the time of when oral dosing (or IV dosing, if applicable) begins depends on the CrCl of the patient. With respect to some drugs for which liver clearance is alternatively or in addition a factor to consider, threshold liver clearance values can be provided by the dosing criteria of the system. Oral dosing for CrCl of >90 mL/min and 60-90 mL/min typically begins 4 h after IV infusion (e.g., 5 hours after the start of a 1 h IV). Oral dosing for CrCl of 30-60 mL/min typically begins 6 h after IV infusion (e.g., 7 h after the start of a 1 h IV). Oral dosing for CrCl of 10-30 mL/min typically begins 12 h after IV infusion (e.g., 13 h after the start of a 1 h IV). Such minimum delays can also be applicable to starting on an IV maintenance dose after the IV loading dose. For other antiarrhythmic drugs, depending on the particular antiarrhythmic drug (e.g., dofetilide, amiodarone, ibutilide, dronedarone, procainamide, flecainide, or propafenone) to be administered, the timing of administration of the oral or IV dose relative to the IV loading dose can be adjusted up or down to be commensurate with the pharmacokinetics of the drug being administered.

Additional examples of when the oral or IV dosing begins for a CrCl of >90 include 2-6 h after completion of infusion. Further examples include 2, 3, 4, 5, to 6 h or longer such as at least 2 hours, at least 3 hours, at least 4 hours, at least 5 hours, at least 6 hours, at least 7 hours, at least 8 hours, at least 9 hours, at least 10 hours, at least 11 hours or at least 12 hours.

Additional examples of when the oral or IV dosing begins for a CrCl of 60-90 include 2-6 h after completion of infusion. Further examples include 2, 3, 4, 5, to 6 h or longer such as at least 2 hours, at least 3 hours, at least 4 hours, at least 5 hours, at least 6 hours, at least 7 hours, at least 8 hours, at least 9 hours, at least 10 hours, at least 11 hours or at least 12 hours.

Additional examples of when the oral or IV dosing begins for a CrCl of 30-60 include 4-8 h after completion of infusion. Further examples include 4, 5, 6, 7, to 8 h or longer such as at least 4 hours, at least 5 hours, at least 6 hours, at least 7 hours, at least 8 hours, at least 9 hours, at least 10 hours, at least 11 hours or at least 12 hours.

Additional examples of when the oral or IV dosing begins for a CrCl of 10-30 include 10-14 h after completion of infusion. Further examples include 10, 11, 12, 13, to 14 h or longer such as at least 10 hours, at least 11 hours, at least 12 hours, at least 13 hours or at least 14 hours.

As can be seen in Table 1, the oral dosing interval depends on the CrCl of the patient. Oral dosing for CrCl of >90 and 60-90 is typically at 12 h intervals (BID). Oral dosing for CrCl of 30-60 is typically at a 24 H interval (QD). Oral dosing for CrCl of 10-30 is typically at a 48 h interval. For other antiarrhythmic drugs, depending on the particular antiarrhythmic drug (e.g., dofetilide, amiodarone, ibutilide, dronedarone, procainamide, flecainide, or propafenone) to be administered, the dosing interval for subsequent oral or IV doses can be adjusted up or down to be commensurate with the pharmacokinetics of the drug being administered.

Also, Table 1 shows that the amount of sotalol hydrochloride appropriate for a subject with a CrCl of 10-30 mL/min or 30-60 mL/min is, surprisingly, higher than is appropriate for a subject with a CrCl of >90 mL/min.

Additional examples of the oral dosing interval for a CrCl of >90 include 8-16 h after completion of infusion. Further examples include 8, 9, 10, 11, 12, 13, 14, 15, to 16 h.

Additional examples of the oral dosing interval for a CrCl of 60-90 include 8-16 h after completion of infusion. Further examples include 8, 9, 10, 11, 12, 13, 14, 15, to 16 h.

Additional examples of the oral dosing interval for a CrCl of 30-60 include 20-28 h after completion of infusion. Further examples include 20, 21, 22, 23, 24, 25, 26, 27, to 28 h.

Additional examples of when the oral dosing begins for a CrCl of 10-30 include 40-56 h after completion of infusion. Further examples include 40, 41, 42, 43, 44, 45, 46, 47, 48, 49, 50, 51, 52, 53, 54, 55, to 56 h.

In another example, one implementation provides a method of initiating or escalating sotalol therapy, comprising: administering to a patient in need thereof an IV and oral dosage of sotalol selected by a physician, wherein the patient's physician selects the IV and oral dosages based on the patient's CrCl as defined in Table 1.

In another example, one implementation provides a method of initiating or escalating oral sotalol therapy, comprising:

A intravenously (IV) administering sotalol hydrochloride over a period of 1 hour, to a patient in need thereof, wherein the IV dosage of the dosing criteria is selected from dosages I(a)-IV(d):

I for patients having a creatinine clearance (CrCl) of >90 mL/min;
  (a) 60 mg for a patient naïve to sotalol and having a target of 80 mg;
  (b) 90 mg for a patient naïve to sotalol and having a target of 120 mg;
  (c) 75 mg for a patient previously receiving 80 mg of sotalol;
  (d) 90 mg for a patient previously receiving 120 mg of sotalol;
II for patients having a creatinine clearance (CrCl) of 60-90 mL/min;
  (a) 82.5 mg for a patient naïve to sotalol and having a target of 80 mg;
  (b) 125 mg for a patient naïve to sotalol and having a target of 120 mg;
  (c) 82.5 mg for a patient previously receiving 80 mg of sotalol;
  (d) 105 mg for a patient previously receiving 120 mg of sotalol;
III for patients having a creatinine clearance (CrCl) of 30-60 mL/min;
  (a) 75 mg for a patient naïve to sotalol and having a target of 80 mg;
  (b) 112.5 mg for a patient naïve to sotalol and having a target of 120 mg;
  (c) 82.5 mg for a patient previously receiving 80 mg of sotalol;
  (d) 105 mg for a patient previously receiving 120 mg of sotalol;
IV for patients having a creatinine clearance (CrCl) of 10-30 mL/min;
  (a) 75 mg for a patient naïve to sotalol and having a target of 80 mg;
  (b) 112.5 mg for a patient naïve to sotalol and having a target of 120 mg;
  (c) 82.5 mg for a patient previously receiving 80 mg of sotalol; and,
  (d) 105 mg for a patient previously receiving 120 mg of sotalol; and,
B orally administering sotalol hydrochloride to the patient at a dosage and interval selected from (I)-(IX):
  I 80 mg BID, starting 4 hours after completion of IV doses I(a) and II(a);
  II 120 mg BID, starting 4 hours after completion of IV doses I(b), I(c), II(b), and II(c);
  III 160 mg BID, starting 4 hours after completion of IV doses I(d) and II(d);
  IV 80 mg QD, starting 6 hours after completion of IV dose III(a);
  V 120 mg QD, starting 6 hours after completion of IV doses III(b) and III(c);
  VI 160 mg QD, starting 6 hours after completion of IV dose III(d);
  VII 80 mg at a 48 h interval, starting 12 hours after completion of IV dose IV(a);
  VIII 120 mg at a 48 h interval, starting 12 hours after completion of IV doses IV(b) and IV(c); and,
  IX 160 mg at a 48 h interval, starting 12 hours after completion of IV dose IV(d).

In another example, one implementation provides a method of initiating or escalating oral sotalol therapy, comprising:

A intravenously (IV) administering sotalol hydrochloride over a period of 1 hour, to a patient in need thereof, wherein the IV dosage is selected from dosages I(a)-IV(d):

I for patients having a creatinine clearance (CrCl) of >90 mL/min;
  (a) 60 mg for a patient naïve to sotalol and having a target of 80 mg;
  (b) 90 mg for a patient naïve to sotalol and having a target of 120 mg;
  (c) 75 mg for a patient previously receiving 80 mg of sotalol;
  (d) 90 mg for a patient previously receiving 120 mg of sotalol;
II for patients having a creatinine clearance (CrCl) of 60-90 mL/min;
  (a) 82.5 mg for a patient naïve to sotalol and having a target of 80 mg;
  (b) 125 mg for a patient naïve to sotalol and having a target of 120 mg;
  (c) 82.5 mg for a patient previously receiving 80 mg of sotalol;
  (d) 105 mg for a patient previously receiving 120 mg of sotalol;
III for patients having a creatinine clearance (CrCl) of 30-60 mL/min;
  (a) 75 mg for a patient naïve to sotalol and having a target of 80 mg;
  (b) 112.5 mg for a patient naïve to sotalol and having a target of 120 mg;
  (c) 82.5 mg for a patient previously receiving 80 mg of sotalol;
  (d) 105 mg for a patient previously receiving 120 mg of sotalol;
IV for patients having a creatinine clearance (CrCl) of 10-30 mL/min;
  (a) 75 mg for a patient naïve to sotalol and having a target of 80 mg;
  (b) 112.5 mg for a patient naïve to sotalol and having a target of 120 mg;
  (c) 82.5 mg for a patient previously receiving 80 mg of sotalol; and,
  (d) 105 mg for a patient previously receiving 120 mg of sotalol; and,
B orally administering sotalol hydrochloride to the patient at a dosage and interval selected from (I)-(IX):
  I 80 mg BID, starting 3-5 hours after completion of IV doses I(a) and II(a), such as 4 hours after;
  II 120 mg BID, starting 3-5 hours after completion of IV doses I(b), I(c), II(b), and II(c), such as 4 hours after;
  III 160 mg BID, starting 3-5 hours after completion of IV doses I(d) and II(d), such as 4 hours after;
  IV 80 mg QD, starting 5-7 hours after completion of IV dose III(a), such as 6 hours after;
  V 120 mg QD, starting 5-7 hours after completion of IV doses III(b) and III(c), such as 6 hours after;
  VI 160 mg QD, starting 5-7 hours after completion of IV dose III(d), such as 6 hours after;
  VII 80 mg at a 48 h interval, starting 10-14 hours after completion of IV dose IV(a), such as 12 hours after;

VIII 120 mg at a 48 h interval, starting 10-14 hours after completion of IV doses IV(b) and IV(c), such as 12 hours after; and, IX 160 mg at a 48 h interval, starting 10-14 hours after completion of IV dose IV(d), such as 12 hours after.

In another example, one implementation provides a novel method of initiating or escalating oral sotalol therapy, comprising:

A intravenously (IV) administering sotalol hydrochloride over a period of 1 hour, to a patient in need thereof, wherein the IV dosage is selected from dosages I(a)-IV(d):

I for patients having a creatinine clearance (CrCl) of >90 mL/min;
(a) 50-70 mg for a patient naïve to sotalol and having a target of 80 mg;
(b) 80-100 mg for a patient naïve to sotalol and having a target of 120 mg;
(c) 65-85 mg for a patient previously receiving 80 mg of sotalol;
(d) 80-100 mg for a patient previously receiving 120 mg of sotalol;

II for patients having a creatinine clearance (CrCl) of 60-90 mL/min;
(a) 72.5-92.5 mg for a patient naïve to sotalol and having a target of 80 mg;
(b) 115-135 mg for a patient naïve to sotalol and having a target of 120 mg;
(c) 72.5-92.5 mg for a patient previously receiving 80 mg of sotalol;
(d) 95-115 mg for a patient previously receiving 120 mg of sotalol;

III for patients having a creatinine clearance (CrCl) of 30-60 mL/min;
(a) 65-85 mg for a patient naïve to sotalol and having a target of 80 mg;
(b) 102.5-122.5 mg for a patient naïve to sotalol and having a target of 120 mg;
(c) 72.5-92.5 mg for a patient previously receiving 80 mg of sotalol;
(d) 95-115 mg for a patient previously receiving 120 mg of sotalol;

IV for patients having a creatinine clearance (CrCl) of 10-30 mL/min;
(a) 65-85 mg for a patient naïve to sotalol and having a target of 80 mg;
(b) 102.5-122.5 mg for a patient naïve to sotalol and having a target of 120 mg;
(c) 72.5-92.5 mg for a patient previously receiving 80 mg of sotalol; and,
(d) 95-115 mg for a patient previously receiving 120 mg of sotalol; and, B orally administering sotalol hydrochloride to the patient at a dosage and interval selected from (I)-(IX):

I 80 mg BID, starting 4 hours after completion of IV doses I(a) and II(a);
II 120 mg BID, starting 4 hours after completion of IV doses I(b), I(c), II(b), and II(c);
III 160 mg BID, starting 4 hours after completion of IV doses I(d) and II(d);
IV 80 mg QD, starting 6 hours after completion of IV dose III(a);
V 120 mg QD, starting 6 hours after completion of IV doses III(b) and III(c);
VI 160 mg QD, starting 6 hours after completion of IV dose III(d);
VII 80 mg at a 48 h interval, starting 12 hours after completion of IV dose IV(a);

VIII 120 mg at a 48 h interval, starting 12 hours after completion of IV doses IV(b) and IV(c); and, IX 160 mg at a 48 h interval, starting 12 hours after completion of IV dose IV(d).

In another example, one implementation provides a novel method of initiating or escalating oral sotalol therapy, comprising:

A intravenously (IV) administering sotalol hydrochloride over a period of 40-80 minutes, to a patient in need thereof, wherein the IV dosage is selected from dosages I(a)-IV(d):

I for patients having a creatinine clearance (CrCl) of >90 mL/min;
(a) 50-70 mg for a patient naïve to sotalol and having a target of 80 mg;
(b) 80-100 mg for a patient naïve to sotalol and having a target of 120 mg;
(c) 65-85 mg for a patient previously receiving 80 mg of sotalol;
(d) 80-100 mg for a patient previously receiving 120 mg of sotalol;

II for patients having a creatinine clearance (CrCl) of 60-90 mL/min;
(a) 72.5-92.5 mg for a patient naïve to sotalol and having a target of 80 mg;
(b) 115-135 mg for a patient naïve to sotalol and having a target of 120 mg;
(c) 72.5-92.5 mg for a patient previously receiving 80 mg of sotalol;
(d) 95-115 mg for a patient previously receiving 120 mg of sotalol;

III for patients having a creatinine clearance (CrCl) of 30-60 mL/min;
(a) 65-85 mg for a patient naïve to sotalol and having a target of 80 mg;
(b) 102.5-122.5 mg for a patient naïve to sotalol and having a target of 120 mg;
(c) 72.5-92.5 mg for a patient previously receiving 80 mg of sotalol;
(d) 95-115 mg for a patient previously receiving 120 mg of sotalol;

IV for patients having a creatinine clearance (CrCl) of 10-30 mL/min;
(a) 65-85 mg for a patient naïve to sotalol and having a target of 80 mg;
(b) 102.5-122.5 mg for a patient naïve to sotalol and having a target of 120 mg;
(c) 72.5-92.5 mg for a patient previously receiving 80 mg of sotalol; and,
(d) 95-115 mg for a patient previously receiving 120 mg of sotalol; and, B orally administering sotalol hydrochloride to the patient at a dosage and interval selected from (I)-(IX):

I 80 mg BID, starting 3-5 hours after completion of IV doses I(a) and II(a);
II 120 mg BID, starting 3-5 hours after completion of IV doses I(b), I(c), II(b), and II(c);
III 160 mg BID, starting 3-5 hours after completion of IV doses I(d) and II(d);
IV 80 mg QD, starting 5-7 hours after completion of IV dose III(a);
V 120 mg QD, starting 5-7 hours after completion of IV doses III(b) and III(c);
VI 160 mg QD, starting 5-7 hours after completion of IV dose III(d);
VII 80 mg at a 48 h interval, starting 10-14 hours after completion of IV dose IV(a);

VIII 120 mg at a 48 h interval, starting 10-14 hours after completion of IV doses IV(b) and IV(c); and, IX 160 mg at a 48 h interval, starting 10-14 hours after completion of IV dose IV(d).

In another example, the patient is indicated for chronic, but not acute sotalol therapy.

In another example, the patient is under ECG (a.k.a. EKG) monitoring.

In another example, the patient is in a hospital and/or under QTc monitoring for at least the IV loading portion of the protocol, or for the IV loading protocol and at least 1 oral dose, or for the IV loading protocol and at least 2 oral dosages, or for the IV loading and at least 3 oral dosages.

In another example, the patient is exposed to amounts and frequency of sotalol which are expected to cause the patient to experience 3 sotalol steady state $C_{max}$ in less than 24 hours, which allows for a QTc of the subject that corresponds to the full concentration effect of sotalol to be assessed in less than 24 hours (as opposed to the typical ~72 hours required for oral only initiation and/or escalation).

In another example, the patient is considered to have been initiated/escalated on oral sotalol after having experienced 3 sotalol steady state $C_{max}$.

In a patient having a CrCl of >60 mL, at least 5-6 doses of oral sotalol (BID) are recommended before the patient is able to be discharged. In a patient having a CrCl of 40-60 mL, at least 5-6 doses of oral sotalol (QD) are recommended before the patient is able to be discharged.

In another example, the patient is considered to have been initiated/escalated on oral sotalol after having received at least at least 1, 2, 3, or 4 oral dosages.

In another example, the patient is considered to have been initiated/escalated on oral sotalol after having received at least 1 oral dose or at least 2 oral dosages and the patient's CrCl is >90 mL/min. In another example, the patient received 3 oral dosages. In another example, the patient received 4 oral dosages.

In another example, the patient is considered to have been initiated/escalated on oral sotalol after having received at least 1 oral dose or at least 2 oral dosages and the patient's CrCl is 60-90 mL/min. In another example, the patient received 3 oral dosages. In another example, the patient received 4 oral dosages.

In another example, the patient is considered to have been initiated/escalated on oral sotalol after having received at least 1 oral dose or at least 2 oral dosages and the patient's CrCl is 30-60 mL/min. In another example, the patient received 3 oral dosages. In another example, the patient received 4 oral dosages.

In another example, the patient is considered to have been initiated/escalated on oral sotalol after having received at least 1 oral dose or at least 2 oral dosages and the patient's CrCl is 10-30 mL/min. In another example, the patient received 3 oral dosages. In another example, the patient received 4 oral dosages.

In another example, the method of initiating or escalating oral sotalol therapy, further comprises: prior to IV loading, measuring the patient's serum creatine level and calculating the patient's Creatine Clearance (CrCl) using the Cockcroft-Gault formula.

In another example, the patient's baseline QTc is measured prior to initiation or escalation.

In another example, only patients having a QTc <450 ms are initiated or escalated.

In another example, the patient's QTc is measured at 15 minute intervals during

IV infusion.

In another example, the patient's QTc is measured for 2-4 hours after the first oral dosage.

In another example, the patient's QTc is measured for 2-4 hours after the second oral dosage for patients having a CrCl of >60 mL/min.

In another example, if the patient's QTc is ≥500 ms or if the ΔQTc is 20% when initiating an 80 mg oral dosage, the method is discontinued.

In another example, one implementation provides a method of treating AFIB/AFL, comprising: initiating or escalating sotalol hydrochloride as described herein in a patient in need thereof (e.g., see Table 1).

In another example, the method reduces the overall time of hospitalization of the patient (compared to a patient initiated or escalated with only oral sotalol).

In another example, the patient being initiated/escalated on sotalol and having a CrCl of ≥60 mL/min is able to be discharged from the hospital in less than the standard 72 hours typically required for only oral sotalol initiation/escalation. For example, the patent is able to be discharged (or is discharged) from 18-48 hours after completion of IV initiation, such as within 1 day. Additional examples include from 18-36 hours, from 18-24 hours, and from 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, to 48 hours after completion of IV initiation.

In another example, the patient being initiated/escalated on sotalol and having a CrCl of from 10-60 mL/min is able to be discharged from the hospital in less than the standard 5-6 days (5-6 dosages QD) typically required for only oral sotalol initiation/escalation and having a CrCl of 40-60 mL/min. For example, the patent is able to be discharged (or is discharged) from 24-96 hours after IV initiation, such as within 1 day. Additional examples include from 24-72 hours, from 36-48 hours, and from 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, to 72 hours after IV initiation.

In another example, the oral therapy is maintained at the patient's physician's discretion. For example, the oral therapy can be continued for days, weeks, or months.

In another example, the patient's QTc is monitored via electrocardiography.

In another example, the patient's QTc is measured at baseline (prior to sotalol administration) and then measured periodically thereafter (e.g., at 15 or 30 minute intervals during loading). The QTc can be measured at other intervals if more (shorter time period) or less data (longer time periods) data is desired.

In another example, the HR and BP the patient is monitored at 15 minute intervals (or 30 minute intervals) during IV administration. If a BP below 90 mmHg and HR <50 bpm are observed, then the IV is discontinued. The HR and BP are also typically monitored for 15-30 minutes after completion of the IV administration.

In another example, one implementation provides sotalol hydrochloride as an aqueous formulation in single-dose vials at a concentration suitable for intravenous use and subsequent dilution in saline, 5% dextrose in water (D5W), or Ringer's lactate. A volume is chosen by a health professional which is convenient for administration and consistent with fluid restriction.

In another example, one implementation provides a novel pharmaceutical composition, comprising: a syringe, comprising: from 60-125 mg of sotalol. In another example, the syringe consists essentially of 60-125 mg of sotalol and at least one diluent selected from: saline, 5% dextrose in water (D5W), and Ringer's lactate.

In another example, the syringe, comprises: 60 mg of sotalol. In another example, the syringe consists essentially of 60 mg of sotalol and at least one diluent selected from: saline, 5% dextrose in water (D5W), and Ringer's lactate.

In another example, the syringe, comprises: 75 mg of sotalol. In another example, the syringe consists essentially of 75 mg of sotalol and at least one diluent selected from: saline, 5% dextrose in water (D5W), and Ringer's lactate.

In another example, the syringe, comprises: 82.5 mg of sotalol. In another example, the syringe consists essentially of 82.5 mg of sotalol and at least one diluent selected from: saline, 5% dextrose in water (D5W), and Ringer's lactate.

In another example, the syringe, comprises: 90 mg of sotalol. In another example, the syringe consists essentially of 90 mg of sotalol and at least one diluent selected from: saline, 5% dextrose in water (D5W), and Ringer's lactate.

In another example, the syringe, comprises: 105 mg of sotalol. In another example, the syringe consists essentially of 105 mg of sotalol and at least one diluent selected from: saline, 5% dextrose in water (D5W), and Ringer's lactate.

In another example, the syringe, comprises: 112.5 mg of sotalol. In another example, the syringe consists essentially of 112.5 mg of sotalol and at least one diluent selected from: saline, 5% dextrose in water (D5W), and Ringer's lactate.

In another example, the syringe, comprises: 125 mg of sotalol. In another example, the syringe consists essentially of 125 mg of sotalol and at least one diluent selected from: saline, 5% dextrose in water (D5W), and Ringer's lactate.

In another example, the volume of liquid in the syringe is from 5, 6, 7, 8, 9, to 10 mL.

In another example, the syringe is filled from a vial of 15 mg/mL of sotalol and further diluted to a final volume of 10 mL, wherein the diluent is selected from. saline, 5% dextrose in water (D5W), and Ringer's lactate.

EXAMPLE 1

Antiarrhythmic Drug Administration System

A patient in need of antiarrhythmic drug treatment or therapy, for example sotalol hydrochloride, is admitted for initiation or escalation of the drug while under QTc monitoring. Patient data are inputted into the medical device for determining dosing of the antiarrhythmic drug, including a creatinine clearance or creatinine level of the patient, optionally a start time for the infusion to begin, whether the patient is being initiated or escalated on the drug, and the target oral dose for the patient. For example, for initiating a patient on an antiarrhythmic drug, the target oral or IV dose is input into the medical device. For escalating a patient from one current oral or IV dose to a second higher oral or IV dose, escalation is indicated as well as the target oral dose. For example, if escalation is indicated with a target oral dose of 120 mg of sotalol hydrochloride, then the current oral dose would be understood to be 80 mg. Likewise, if escalation is indicated with a target oral dose of 160 mg, then the current oral dose would be understood to be 120 mg. In embodiments, the patient is optionally connected to a patient monitoring device configured to obtain at least heart rate and/or QT interval and/or QTc data and/or creatinine clearance. In embodiments, the patient monitor is connected with the medical device for determining dosing, such that the heart rate and/or QT interval and/or QTc data, and/or patient creatinine clearance, can be automatically input, or a health professional can input the information into the medical device manually from any one or more patient monitoring device or database if desired. Based on the inputted infusion start time, whether the patient is being escalated or initiated, the patient's creatinine clearance, the target oral dose, and optionally heart rate and/or QT interval and/or QTc data, the medical device for determining dosing of the antiarrhythmic drug determines a treatment plan based on stored dosage criteria/protocols. In embodiments, the stored dosage criteria or storage of any patient/subject data or storage of software, the app, or computer-executable instructions can be stored in a different location (than on the medical device) and made available or accessible to the medical device (such as through networking and/or cloud computing). The treatment plan can be approved by a physician remotely or on a system interface, such as from a smartphone. A first IV loading dose of antiarrhythmic drug is administered to the patient based on the treatment plan determined by the medical device for determining the dosing of the antiarrhythmic drug. The administering can be performed/controlled directly or indirectly by an administration system, for example, by controlling an infusion pump to deliver the antiarrhythmic drug to the patient. The device/system can also be configured to provide instructions to a health professional regarding the treatment plan such that the health professional can control the infusion pump to administer the antiarrhythmic drug to the patient according to the treatment plan. Included in the outputs of the treatment plan are the amount of the IV dose, the time of the first oral dose and the oral dosing interval or time or subsequent oral dose(s) if any. The dose amount and administration time are provided by the treatment plan and are based on creatine clearance or liver clearance capability. In the case of sotalol hydrochloride, the treatment plan is based on the patient's creatinine clearance or creatinine level, whether the patient is being initiated or escalated on the drug, the target oral dose, and the projected start time for the protocol to begin, i.e., the start time for IV infusion. The time for oral dosing to begin is based on the patient's creatinine clearance and the start time of the infusion. The oral dosing interval is based on the patient's creatinine clearance or creatinine level, and a start time for oral doses subsequent to the first oral dose is based on the start time of the first oral dose. If a different start time than the initially projected start time for infusion is needed, then the dosing protocol can be recalculated based on a new input of an actual start time for infusion and/or a new projected start time for infusion. If more than one IV dosing option is appropriate, then a choice of IV dosing options can be presented/outputted.

In embodiments, the patient monitor can obtain heart rate and/or QT intervals either continuously or at time periods established by the treatment plan according to the dosing protocol. Based on the QT interval response to the antiarrhythmic drug being administered, additional IV doses of antiarrhythmic drug are administered and/or oral doses of antiarrhythmic drug are administered/instructed by the system. Based on the QT interval response, the IV and/or oral dosages are adjusted accordingly, for example, the dosage amount can be decreased, increased or halted. In embodiments, the administration system is configured to halt treatment, or provide instructions for halting treatment, and notify a system user, for example by way of an alarm or alert such as a text alert, if the patient's heart rate or QT interval deviate from predetermined accepted values. The administration system is additionally configured to update the treatment plan based on the QT interval response during and after administration of each dose of antiarrhythmic drug. If the treatment plan is updated by the system, the system can prompt a user for approval prior to further administration of antiarrhythmic drug.

EXAMPLE 2

Example Sotalol Protocol

Dosing criteria for the device and/or system of Example 1 above can include criteria for infusing a loading dose of sotalol for a period of one hour, as well as criteria for monitoring a patient's QTc at 15 minute intervals during the infusion. If the baseline QTc is >450 ms (JT >330 ms if QRS over 100 ms), sotalol is not recommended.

Monitoring of QTc is continued around $T_{max}$ (2 to 4 hours post-dose) following the first oral dose (in all patients) and second oral dose (in patients with CrCl ≥60 mL/min).

If the QTc prolongs to ≥500 ms or increases 20% from baseline when initiating for an oral dose of 80 mg, the dosing criteria involves discontinuing the drug; if initiating for an oral dose of 120 mg the dosing criteria involves discontinuing the drug and considering a lower dose. If re-initiation at a lower dose of 80 mg is desired, the dosing criteria involves waiting at least 1 day (in patients with CrCl ≥60 mL/min), or at least 3 days (in patients with CrCl ≥30 to <60 mL/min), or 7 days (in patients with CrCl ≥10 to <30 mL/min).

The dosing criteria of the administration system comprises amounts of various intravenous loading doses, the dosing interval(s) for oral or IV maintenance administration, and the minimum delay (if any) between the end of the infusion and the first oral or IV maintenance dose, which depend on the target oral or IV dose and creatinine clearance; see Table 1.

EXAMPLE 3

Example Formulations

Intravenous sotalol injection is supplied as a sterile, clear solution in a 10 mL single-dose vial, for intravenous administration after dilution. Each vial contains 150 mg racemic sotalol hydrochloride (equivalent to 132.8 mg racemic sotalol) in sodium acetate buffer. The sotalol hydrochloride concentration of the formulation is 15 mg/mL. Each mL contains 2.9 mg glacial acetic acid in water for injection as an inactive ingredient. The pH of the injection is adjusted with sodium hydroxide to be between 6.0 and 7.0.

Exemplary formulations for other antiarrhythmic drugs, including dofetilide, amiodarone, ibutilide, dronedarone, procainamide, flecainide, or propafenone can be found in the product labels referenced herein.

EXAMPLE 4

Sotalol Administration System

A specific example of a medical device and/or system employing the particular features of Examples 1-3 is provided as follows. A patient is identified for whom initiation or escalation of sotalol is desired while under QTc monitoring. For initiating a patient on sotalol, the target oral sotalol dose is input into the administration system. For escalating a patient from a current/previous oral sotalol dose (e.g., 80 mg or 120 mg) to a second higher oral sotalol dose (e.g., respectively 120 mg or 160 mg), escalation is input into the administration system along with the target oral sotalol dose. Based on the inputted patient data, the medical device for determining dosing of the antiarrhythmic drug determines a treatment plan based on dosage criteria/protocols.

The dosage criteria/protocols comprise the following rules relating to determining the appropriate IV loading dose for a particular patient:

Dosing based on administering a loading dose of sotalol hydrochloride over a period of 1 hour, wherein the IV loading dosage criteria is selected from dosages I(a)-IV(d):

I for patients having a creatinine clearance (CrCl) of >90 mL/min;
  (a) 60 mg for a patient naïve to sotalol and having a target of 80 mg;
  (b) 90 mg for a patient naïve to sotalol and having a target of 120 mg;
  (c) 75 mg for a patient previously receiving 80 mg of sotalol;
  (d) 90 mg for a patient previously receiving 120 mg of sotalol;

II for patients having a creatinine clearance (CrCl) of 60 to 90 mL/min;
  (a) 82.5 mg for a patient naïve to sotalol and having a target of 80 mg;
  (b) 125 mg for a patient naïve to sotalol and having a target of 120 mg;
  (c) 82.5 mg for a patient previously receiving 80 mg of sotalol;
  (d) 105 mg for a patient previously receiving 120 mg of sotalol;

III for patients having a creatinine clearance (CrCl) of 30 to 60 mL/min;
  (a) 75 mg for a patient naïve to sotalol and having a target of 80 mg;
  (b) 112.5 mg for a patient naïve to sotalol and having a target of 120 mg;
  (c) 82.5 mg for a patient previously receiving 80 mg of sotalol;
  (d) 105 mg for a patient previously receiving 120 mg of sotalol;

IV for patients having a creatinine clearance (CrCl) of 10 to 30 mL/min;
  (a) 75 mg for a patient naïve to sotalol and having a target of 80 mg;
  (b) 112.5 mg for a patient naïve to sotalol and having a target of 120 mg;
  (c) 82.5 mg for a patient previously receiving 80 mg of sotalol;
  (d) 105 mg for a patient previously receiving 120 mg of sotalol.

A first IV loading dose of sotalol is administered to the patient based on the above dosing criteria applicable to the patient. For example, the IV loading dose according to protocol I(a) would be determined by the device or system as an appropriate loading dose for a patient who is naïve to sotalol, with a target oral dose of 80 mg and having a creatinine clearance in the range of >90 mL/min. The administering can be performed/controlled directly or indirectly by any component of the administration system, for example, by controlling an infusion pump to deliver the antiarrhythmic drug to the patient. The system can also be configured to provide instructions to a health professional regarding the treatment plan such that the health professional can control the infusion pump to administer the antiarrhythmic drug to the patient according to the treatment plan.

In embodiments, optionally the patient monitor continues to obtain heart rate and/or QT intervals either continuously or at time periods established by the treatment plan according to the dosing protocol. If the QTc prolongs to ≥500 ms or increases 20% from baseline when initiating for an oral dose of 80 mg, the dosing criteria involves discontinuing the drug; if initiating for an oral dose of 120 mg the dosing criteria involves discontinuing the drug and considering a lower dose. If re-initiation at a lower dose of 80 mg is desired, the dosing criteria involves waiting at least 1 day (in patients with CrCl ≥60 mL/min), or at least 3 days (in patients with CrCl ≥30 to <60 mL/min), or 7 days (in patients with CrCl ≥10 to <30 mL/min).

Based on the QT interval response to the antiarrhythmic drug being administered, oral doses of antiarrhythmic drug are administered/instructed by the system according to dosing criteria adhering to the following rules:

Dosing based on orally administering sotalol hydrochloride to the patient, wherein the dosing criteria of the administration system are selected from the following dosage/intervals selected from (I)-(IX):

I 80 mg BID, starting 4 hours after completion of IV doses I(a) or II(a);

II 120 mg BID, starting 4 hours after completion of IV doses I(b), I(c), II(b), or II(c);

III 160 mg BID, starting 4 hours after completion of IV doses I(d) or II(d);

IV 80 mg QD, starting 6 hours after completion of IV dose III(a);

V 120 mg QD, starting 6 hours after completion of IV doses III(b) or III(c);

VI 160 mg QD, starting 6 hours after completion of IV dose III(d);

VII 80 mg at a 48 h interval, starting 12 hours after completion of IV dose IV(a);

VIII 120 mg at a 48 h interval, starting 12 hours after completion of IV doses IV(b) or IV(c);

IX 160 mg at a 48 h interval, starting 12 hours after completion of IV dose IV(d).

Based on the QT interval response, the medical device or system can indicate that IV and/or oral dosages should be adjusted accordingly, for example, the dosage amount can be decreased, increased or halted. In embodiments, the administration system is configured to halt treatment, or provide instructions for halting treatment, and notify a system user, for example by way of an alarm or alert such as a text alert, if the patient's heart rate or QT interval deviate from predetermined accepted values. The administration system can also be configured to update the treatment plan based on the QT interval response during and/or after administration of each dose of antiarrhythmic drug.

The present disclosure has described particular implementations having various features. In light of the disclosure provided herein, it will be apparent to those skilled in the art that various modifications and variations can be made without departing from the scope or spirit of the disclosure. One skilled in the art will recognize that the disclosed features may be used singularly, in any combination, or omitted based on the requirements and specifications of a given application or design. When an implementation refers to "comprising" certain features, it is to be understood that the implementations can alternatively "consist of" or "consist essentially of" any one or more of the features. Other implementations will be apparent to those skilled in the art from consideration of the specification and practice of the disclosure.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the disclosure fall within the scope of the disclosure. Further, all of the references cited in this disclosure including patents, published applications, and non-patent literature are each individually incorporated by reference herein in their entireties and as such are intended to provide an efficient way of supplementing the enabling disclosure as well as provide background detailing the level of ordinary skill in the art.

The invention claimed is:

1. A treatment management application configured to perform a set of operations comprising:
   (i) reading, prompting input of and/or accepting the following as inputs:
      a projected start time for a sotalol hydrochloride 1 hour infusion;
      a creatinine clearance (CrCl) or creatinine level of a subject;
      whether the subject is being initiated or escalated on the sotalol hydrochloride; and
      an amount of an oral target dosage of sotalol hydrochloride for the subject; and
   (ii) executing computer executable instructions to derive from a set of rules a sotalol hydrochloride IV and oral dosing protocol for the subject based on the inputs, the dosing protocol comprising:
      one or more amount of the sotalol hydrochloride for infusion as a loading dose;
      a time for a first oral dose of sotalol hydrochloride; and
      optionally a time for a second oral dose of sotalol hydrochloride; and
   (iii) outputting the sotalol hydrochloride IV and oral dosing protocol.

2. The treatment management application of claim 1, wherein the set of operations further comprises reading, prompting input of and/or accepting as an input an actual start time for the sotalol hydrochloride infusion and outputting a revised dosing protocol with confirmed or updated times for the first oral sotalol hydrochloride dose and optionally the second oral sotalol hydrochloride dose.

3. The treatment management application of claim 1, wherein:
   for the subject who has a CrCl of >90 mL/min and is being initiated on an 80 mg target oral sotalol hydrochloride dose, the dosing protocol comprises:
      60 mg as the amount for the infusion of sotalol hydrochloride as the loading dose;
      a time of at least 4 hours after completion of the loading dose as the time for the first oral dose; and
      a time of 12 hours after the first oral dose as the time for the second oral dose.

4. The treatment management application of claim 1, wherein:
   for the subject who has a CrCl of 60-90 mL/min and is being initiated on an 80 mg target oral sotalol hydrochloride dose, the dosing protocol comprises:
      82.5 mg as the amount for the infusion as the loading dose;
      a time of at least 4 hours after completion of the loading dose as the time for the first oral dose; and
      a time of 12 hours after the first oral dose as the time for the second oral dose.

5. The treatment management application of claim 1, wherein:
for the subject who has a CrCl of 30-60 mL/min and is being initiated on an 80 mg target oral sotalol hydrochloride dose, the dosing protocol comprises:
75 mg as the amount for the infusion as the loading dose;
a time of at least 6 hours after completion of the loading dose as the time for the first oral dose; and
a time of 24 hours after the first oral dose as the time for the second oral dose.

6. The treatment management application of claim 1, wherein:
for the subject who has a CrCl of 10-30 mL/min and is being initiated on an 80 mg target oral sotalol hydrochloride dose, the dosing protocol comprises:
75 mg as the amount for the infusion as the loading dose;
a time of at least 12 hours after completion of the loading dose as the time for the first oral dose; and
a time of 48 hours after the first oral dose as the time for the second oral dose.

7. The treatment management application of claim 1, wherein:
for the subject who has a CrCl of >90 mL/min and is being initiated on an 120 mg target oral sotalol hydrochloride dose, the dosing protocol comprises:
75 mg as the amount for the infusion as the loading dose;
a time of at least 4 hours after completion of the loading dose as the time for the first oral dose; and
a time of 12 hours after the first oral dose as the time for the second oral dose.

8. The treatment management application of claim 1, wherein:
for the subject who has a CrCl of 60-90 mL/min and is being initiated on an 120 mg target oral sotalol hydrochloride dose, the dosing protocol comprises:
82.5 mg as the amount for the infusion as the loading dose;
a time of at least 4 hours after completion of the loading dose as the time for the first oral dose; and
a time of 12 hours after the first oral dose as the time for the second oral dose.

9. The treatment management application of claim 1, wherein:
for the subject who has a CrCl of 30-60 mL/min and is being initiated on an 120 mg target oral sotalol hydrochloride dose, the dosing protocol comprises:
82.5 mg as the amount for the infusion as the loading dose;
a time of at least 6 hours after completion of the loading dose as the time for the first oral dose; and
a time of 24 hours after the first oral dose as the time for the second oral dose.

10. The treatment management application of claim 1, wherein:
for the subject who has a CrCl of 10-30 mL/min and is being initiated on an 120 mg target oral sotalol hydrochloride dose, the dosing protocol comprises:
82.5 mg as the amount for the infusion as the loading dose;
a time of at least 12 hours after completion of the loading dose as the time for the first oral dose; and
a time of 48 hours after the first oral dose as the time for the second oral dose.

11. The treatment management application of claim 1, wherein:
for the subject who has a CrCl of >90 mL/min and is being escalated from an oral dose of 80 mg to a target oral sotalol hydrochloride dose of 120 mg, the dosing protocol comprises:
90 mg as the amount for the infusion as the loading dose;
a time of at least 4 hours after completion of the loading dose as the time for the first oral dose; and
a time of 12 hours after the first oral dose as the time for the second oral dose.

12. The treatment management application of claim 1, wherein:
for the subject who has a CrCl of 60-90 mL/min and is being escalated from an oral dose of 80 mg to a target oral sotalol hydrochloride dose of 120 mg, the dosing protocol comprises:
125 mg as the amount for the infusion as the loading dose;
a time of at least 4 hours after completion of the loading dose as the time for the first oral dose; and
a time of 12 hours after the first oral dose as the time for the second oral dose.

13. The treatment management application of claim 1, wherein:
for the subject who has a CrCl of 30-60 mL/min and is being escalated from an oral dose of 80 mg to a target oral sotalol hydrochloride dose of 120 mg, the dosing protocol comprises:
2 112.5 mg as the amount for the infusion as the loading dose;
a time of at least 6 hours after completion of the loading dose as the time for the first oral dose; and
a time of 24 hours after the first oral dose as the time for the second oral dose.

14. The treatment management application of claim 1, wherein:
for the subject who has a CrCl of 10-30 mL/min and is being escalated from an oral dose of 80 mg to a target oral sotalol hydrochloride dose of 120 mg, the dosing protocol comprises:
112.5 mg as the amount for the infusion as the loading dose;
a time of at least 12 hours after completion of the loading dose as the time for the first oral dose; and
a time of 48 hours after the first oral dose as the time for the second oral dose.

15. The treatment management application of claim 1, wherein:
for the subject who has a CrCl of >90 mL/min and is being escalated from an oral dose of 120 mg to a target oral sotalol hydrochloride dose of 160 mg, the dosing protocol comprises:
90 mg as the amount for the infusion as the loading dose;
a time of at least 4 hours after completion of the loading dose as the time for the first oral dose; and
a time of 12 hours after the first oral dose as the time for the second oral dose.

16. The treatment management application of claim 1, wherein:
for the subject who has a CrCl of 60-90 mL/min and is being escalated from an oral dose of 120 mg to a target oral sotalol hydrochloride dose of 160 mg, the dosing protocol comprises:

105 mg as the amount for the infusion as the loading dose;
a time of at least 4 hours after completion of the loading dose as the time for the first oral dose; and
a time of 12 hours after the first oral dose as the time for the second oral dose.

17. The treatment management application of claim 1, wherein:
for the subject who has a CrCl of 30-60 mL/min and is being escalated from an oral dose of 120 mg to a target oral sotalol hydrochloride dose of 160 mg, the dosing protocol comprises:
105 mg as the amount for the infusion as the loading dose;
a time of at least 6 hours after completion of the loading dose as the time for the first oral dose; and
a time of 24 hours after the first oral dose as the time for the second oral dose.

18. The treatment management application of claim 1, wherein:
for the subject who has a CrCl of 10-30 mL/min and is being escalated from an oral dose of 120 mg to a target oral sotalol hydrochloride dose of 160 mg, the dosing protocol comprises:
105 mg as the amount for the infusion as the loading dose;
a time of at least 12 hours after completion of the loading dose as the time for the first oral dose; and
a time of 48 hours after the first oral dose as the time for the second oral dose.

19. A medical device comprising:
an electronic device, optionally a handheld electronic device;
software stored on or accessible to the electronic device and operably configured to:
(i) read, prompt input of and/or accept as inputs: a creatinine clearance (CrCl) of a subject; whether the subject is being initiated or escalated on sotalol hydrochloride; an amount of an oral target dosage of sotalol hydrochloride for the subject; and a projected or actual start time for sotalol hydrochloride infusion; and
(ii) execute computer executable instructions to derive from a set of rules an IV and oral sotalol hydrochloride dosing protocol for the subject based on one or more of or all of the inputs, the dosing protocol comprising at least one or more amount of the sotalol hydrochloride for infusion as a loading dose and a time for a first oral dose of sotalol hydrochloride based on the projected or actual start time; and
(iii) output the sotalol hydrochloride dosing protocol; and
a display capable of displaying the output of the dosing protocol to a user.

20. A method of treating a subject comprising:
administering sotalol hydrochloride to a subject based on outputs from a treatment management application configured to perform a set of operations comprising:
(i) reading, prompting input of and/or accepting the following as inputs:
a projected start time for a sotalol hydrochloride 1 hour infusion;
a creatinine clearance (CrCl) or creatinine level of a subject;
whether the subject is being initiated or escalated on the sotalol hydrochloride; and
an amount of an oral target dosage of sotalol hydrochloride for the subject; and
(ii) executing computer executable instructions to derive from a set of rules an IV and oral sotalol hydrochloride dosing protocol for the subject based on the inputs, the dosing protocol comprising:
one or more amount of the sotalol hydrochloride for infusion as a loading dose;
a time for a first oral dose of sotalol hydrochloride; and
optionally a time for a second oral dose of sotalol hydrochloride; and
(iii) outputting the sotalol hydrochloride dosing protocol; and
optionally administering the sotalol hydrochloride in a manner for providing for maintenance of normal sinus rhythm in patients with symptomatic atrial fibrillation or atrial flutter and/or who are currently in sinus rhythm.

* * * * *